US006700039B1

(12) United States Patent
Jepson et al.

(10) Patent No.: US 6,700,039 B1
(45) Date of Patent: Mar. 2, 2004

(54) GENETIC METHOD FOR CONTROLLING SPROUTING

(75) Inventors: Ian Jepson, Bracknell (GB); Marcus Ebneth, Gatersleben (DE); Uwe Sonnewald, Gatersleben (DE)

(73) Assignee: Syngenta Limited, Surrey (GB)

( * ) Notice: Subject to any disclaimer, the term of this patent is extended or adjusted under 35 U.S.C. 154(b) by 0 days.

(21) Appl. No.: 09/463,239

(22) PCT Filed: Jul. 10, 1998

(86) PCT No.: PCT/GB98/02023

§ 371 (c)(1), (2), (4) Date: Jan. 21, 2000

(87) PCT Pub. No.: WO99/06578

PCT Pub. Date: Feb. 11, 1999

(30) Foreign Application Priority Data

Jul. 30, 1997 (EP) .......................................... 97113118

(51) Int. Cl.[7] .......................... A01H 1/00; C12N 15/82; C12N 15/87

(52) U.S. Cl. ....................... 800/278; 800/284; 800/286; 800/287; 800/285; 800/288

(58) Field of Search ................................ 800/278, 284, 800/285, 286, 287, 288

(56) References Cited

FOREIGN PATENT DOCUMENTS

| | | | |
|---|---|---|---|
| DE | 42 13 444 A1 | * | 10/1993 |
| WO | WO 94/03619 | * | 2/1994 |

OTHER PUBLICATIONS

Salisbury, F. B et al., "Plant Physiology", Wadsworth Publishing Company, p. 234, 236 and 243 (1985).*

Eckes, P., et al., Mol Gen Genet, vol. 205, pps 14–22, 1986.

Angell, S.M., et al., The EMBO Journal, vol. 16, No. 12, pps 3675–3684, 1997.

Lehming, N., et al., The EMBO Journal, vol. 6, No. 10, pps 3145–3153, 1987.

* cited by examiner

*Primary Examiner*—Kenneth R. Horlick
*Assistant Examiner*—Teresa Strzelecka
(74) *Attorney, Agent, or Firm*—Bruce Vrana

(57) ABSTRACT

This invention relates to a method of controlling sprout formation in plants and parts thereof including vegetative storage organs. The method involves the use of target and organ specific promoters to control expression of DNA sequences to inhibit sprouting. Sprouting is restored by switching on expression of DNA sequences using inducible promoter regions where sprouting may be controlled by, for example, application of an external chemical stimulus.

9 Claims, 35 Drawing Sheets

Figure 1:
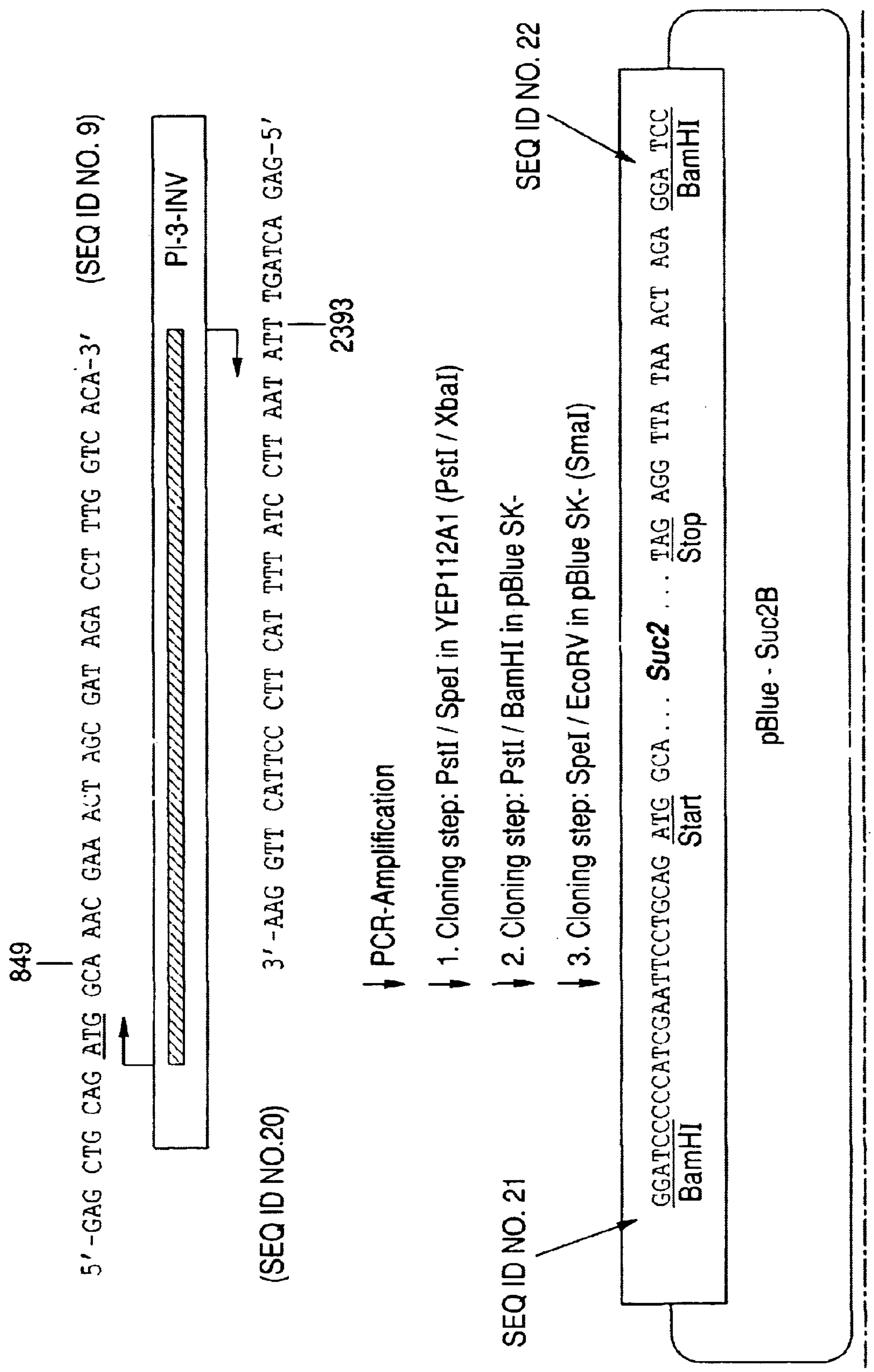
Figure 1:
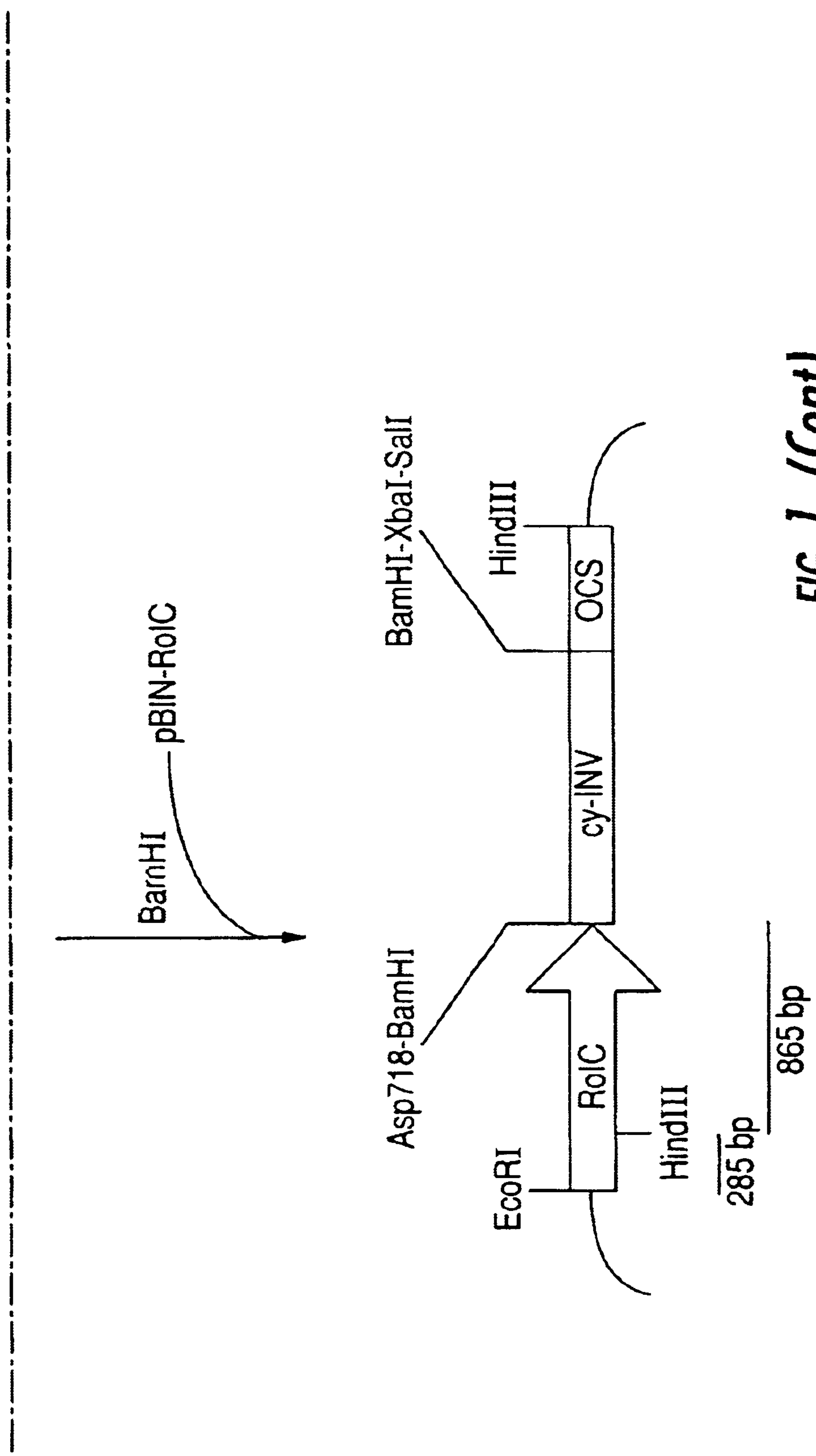

A
B
C
D 1 growing tuber
2 sprout
3 0-0.5 cm
4 0.5-1.0 cm
5 1.0-1.5 cm
6 1.5-2.0 cm
7 2.0-2.5 cm
8 2.5-3.0 cm

FIG. 19 1/4 (SEQ ID NO. 27)

```
                9           18           27           36           45           54
5'CGG CGT CCC ACA CTT CGC ATC TAT AGC TTT CGG TCT CCA TTC CCA TCT CCT GGT
  --- --- --- --- --- --- --- --- --- --- --- --- --- --- --- --- --- ---
   R   R   P   T   L   R   I   Y   S   F   R   S   P   F   P   S   P   G

               63           72           81           90           99          108
  TTC CAG TGA GAT GAA CTC TAA TTC CAA TTG GGC TTA AAC CTT TGA TTC ATT CTA
  --- --- --- --- --- --- --- --- --- --- --- --- --- --- --- --- --- ---
   F   Q   *   D   E   L   *   F   Q   L   G   L   N   L   *   F   I   L

              117          126          135          144          153          162
  TTT TTT TTT TTC TAT TTT TTC CAT TAC CTA ATT CAT ATT CAT TCT TTT TTT AAA
  --- --- --- --- --- --- --- --- --- --- --- --- --- --- --- --- --- ---
   F   F   F   F   Y   F   F   H   Y   L   I   H   I   H   S   F   F   K

              171          180          189          198          207          216
  AAA AGC TTT CGT CTC GAT TCA TTT GGT ATA ATG GGT GTT AAG GGA TTT GTT GAA
  --- --- --- --- --- --- --- --- --- --- --- --- --- --- --- --- --- ---
   K   S   F   R   L   D   S   F   G   I   M   G   V   K   G   F   V   E

              225          234          243          252          261          270
  GGA GGT ATT GCT TCG ATT ATT GCT GGT TGT AGT ACT CAC CCA CTT GAT TTA ATC
  --- --- --- --- --- --- --- --- --- --- --- --- --- --- --- --- --- ---
   G   G   I   A   S   I   I   A   G   C   S   T   H   P   L   D   L   I

              279          288          297          306          315          324
  AAA GTC CGT ATG CAG CTT CAG GGA GAA ACC CCA ATT TCA GCT CCG GCG ACT GTT
  --- --- --- --- --- --- --- --- --- --- --- --- --- --- --- --- --- ---
   K   V   R   M   Q   L   Q   G   E   T   P   I   S   A   P   A   T   V

              333          342          351          360          369          378
  CAC AAT CTC CGT CCA GCA CTT GCT TTT CAC ACT GGT GCT GCT AAT CAT ACT TTT
  --- --- --- --- --- --- --- --- --- --- --- --- --- --- --- --- --- ---
   H   N   L   R   P   A   L   A   F   H   T   G   A   A   N   H   T   F
```

Fig.19. 2/4

```
                387             396             405             414             423             432
TCC ATT CCG GCG CCG TCG GTG GTT GCT CCA CCG CGT GTA GGA CCG GTT TCT GTA
--- --- --- --- --- --- --- --- --- --- --- --- --- --- --- --- --- ---
 S   I   P   A   P   S   V   V   A   P   P   R   V   G   P   V   S   V

                441             450             459             468             477             486
GGT GTT AAG ATT ATT CAA CAA GAA GGA GTT GCT GCT TTG TTC TCC GGT GTA TCA
--- --- --- --- --- --- --- --- --- --- --- --- --- --- --- --- --- ---
 G   V   K   I   I   Q   Q   E   G   V   A   A   L   F   S   G   V   S

                495             504             513             522             531             540
GCT ACT GTT CTC CGG ACA GAC ACT TTA CTC TAC AAC CAG AAT GGG TTT ATA CGA
--- --- --- --- --- --- --- --- --- --- --- --- --- --- --- --- --- ---
 A   T   V   L   R   T   D   T   L   L   Y   N   Q   N   G   F   I   R

                549             558             567             576             585             594
TAT GCT GAA GCA AAA ATG GAC CGA TCC AGA TAC TAC ATC ATG CCT TTG TCG AAG
--- --- --- --- --- --- --- --- --- --- --- --- --- --- --- --- --- ---
 Y   A   E   A   K   M   D   R   S   R   Y   Y   I   M   P   L   S   K

                603             612             621             630             639             648
AAG ATC GTT GCC GGA TTA ATC GCC GGC GGG ATC GGA GCT GCC GTC GGT AAT CCC
--- --- --- --- --- --- --- --- --- --- --- --- --- --- --- --- --- ---
 K   I   V   A   G   L   I   A   G   G   I   G   A   A   V   G   N   P

                657             666             675             684             693             702
GCC GAT GTA GCG ATG GTC CGC ATG CAA GCT GAC GGC CGG CTT CCG ATC TCT CAA
--- --- --- --- --- --- --- --- --- --- --- --- --- --- --- --- --- ---
 A   D   V   A   M   V   R   M   Q   A   D   G   R   L   P   I   S   Q
```

Fig.19. 3/4

```
                711             720             729             738             747             756
CGC CGC AAC TAC AAA AGG GTG ATG GAT GCA ATT TCT CAG ATG AGT AAA AGC GAA
--- --- --- --- --- --- --- --- --- --- --- --- --- --- --- --- --- ---
 R   R   N   Y   K   S   V   I   D   A   I   S   Q   M   S   K   S   E

                765             774             783             792             801             810
GGG GTA ACT AGC CTG TGG CGC GGT TCA TCT CTT ACT GTG AAC CGC GCC ATG CTA
--- --- --- --- --- --- --- --- --- --- --- --- --- --- --- --- --- ---
 G   V   T   S   L   W   R   G   S   S   L   T   V   N   R   A   M   L

                819             828             837             846             855             864
GTT ACC GCA TCG CAG CTA GCA TCG TAC GAT CAG TTC AAA GAG ACT ATC CTC GAG
--- --- --- --- --- --- --- --- --- --- --- --- --- --- --- --- --- ---
 V   T   A   S   Q   L   A   S   Y   D   Q   F   K   E   T   I   L   E

                873             882             891             900             909             918
AAG GGG TTA ATG AAG GAT GGG CTT GGG ACA CAT GTG ACT TCG AGT TTT GCT GCT
--- --- --- --- --- --- --- --- --- --- --- --- --- --- --- --- --- ---
 K   G   L   M   K   D   G   L   G   T   H   V   T   S   S   F   A   A

                927             936             945             954             963             972
GGG TTT GTG GCG GCG GTG GCA TCG AAT CCA GTG GAT GTG ATT AAG ACA CGT GTT
--- --- --- --- --- --- --- --- --- --- --- --- --- --- --- --- --- ---
 G   F   V   A   A   V   A   S   N   P   V   D   V   I   K   T   R   V

                981             990             999            1008            1017            1026
ATG AAC ATG AAG GTC GAG CCG GAA ATG GCC CCA CCG TAT AAT GGG GCC ATT GAT
--- --- --- --- --- --- --- --- --- --- --- --- --- --- --- --- --- ---
 C   A   M   K   T   I   K   A   E   G   P   M   A   L   Y   K   G   F

               1089            1098            1107            1116            1125            1134
ATT CCT ACA ATC TCA AGG CAA GGT CCA TTT ACT GTG GTG CTC TTT GTC ACA CTG
--- --- --- --- --- --- --- --- --- --- --- --- --- --- --- --- --- ---
 I   P   T   I   S   R   Q   G   P   F   T   V   V   L   F   V   T   L
```

Fig.19. 4/4

```
                1143            1152            1161            1170            1179            1188
GAA CAA GTC AGG AAA ATG CTC AAG GAT TTT TAA TGA TGA TGA CGA AGA AAA AAA
--- --- --- --- --- --- --- --- --- --- --- --- --- --- --- --- --- ---
 E   Q   V   R   K   M   L   K   D   F   *   *   *   *   R   R   K   K

                1197            1206            1215            1224            1233            1242
AAA TTA ATG GGA TTT TAG TAT TAA GAA TTT AAA AAA AAG TTA AGT TTA ATT TAT
--- --- --- --- --- --- --- --- --- --- --- --- --- --- --- --- --- ---
 K   L   M   G   F   *   Y   *   E   F   K   K   K   L   S   L   I   Y

                1251            1260            1269            1278            1287            1296
GTT TTT AAG TTT TTA AGT TTG GGA AAA GTG ATA CTA TGT TGT GTT CTA ATA TTA
--- --- --- --- --- --- --- --- --- --- --- --- --- --- --- --- --- ---
 V   F   K   F   L   S   L   G   K   V   I   L   C   C   V   L   I   L

                1305            1314            1323            1332            1341            1350
TTA TTA TTG TTA CTT CTA TAT GAA AAA TGA GTT CTT GTT TGG TGG AAA AAA AAA
--- --- --- --- --- --- --- --- --- --- --- --- --- --- --- --- --- ---
 L   L   L   L   L   L   Y   E   K   *   V   L   V   W   W   K   K   K

AA 3'
--
```

Figure 20:
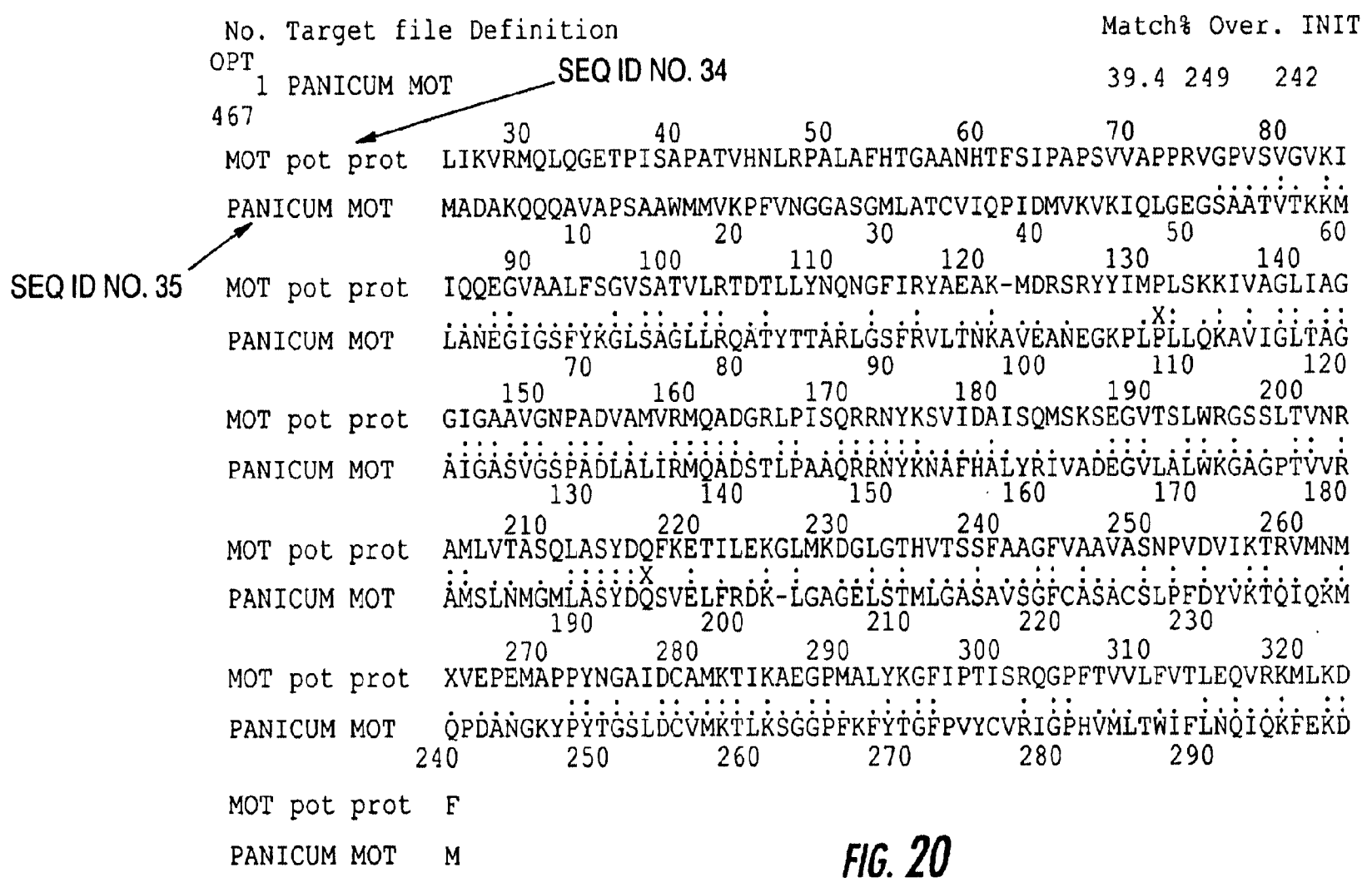

```
No. Target file Definition                                  Match% Over. INIT
OPT
  1 PANICUM MOT                                             39.4 249   242
467
                      30        40        50        60        70        80
MOT pot prot     LIKVRMQLQGETPISAPATVHNLRPALAFHTGAANHTFSIPAPSVVAPPRVGPVSVGVKI

PANICUM MOT      MADAKQQQAVAPSAAWMMVKPFVNGGASGMLATCVIQPIDMVKVKIQLGEGSAATVTKKM
                         10        20        30        40        50        60
                      90       100       110       120       130       140
MOT pot prot     IQQEGVAALFSGVSATVLRTDTLLYNQNGFIRYAEAK-MDRSRYYIMPLSKKIVAGLIAG
                                                                X
PANICUM MOT      LANEGIGSFYKGLSAGLLRQATYTTARLGSFRVLTNKAVEANEGKPLPLLQKAVIGLTAG
                         70        80        90       100       110       120
                     150       160       170       180       190       200
MOT pot prot     GIGAAVGNPADVAMVRMQADGRLPISQRRNYKSVIDAISQMSKSEGVTSLWRGSSLTVNR

PANICUM MOT      AIGASVGSPADLALIRMQADSTLPAAQRRNYKNAFHALYRIVADEGVLALWKGAGPTVVR
                        130       140       150       160       170       180
                     210       220       230       240       250       260
MOT pot prot     AMLVTASQLASYDQFKETILEKGLMKDGLGTHVTSSFAAGFVAAVASNPVDVIKTRVMNM
                              X
PANICUM MOT      AMSLNMGMLASYDQSVELFRDK-LGAGELSTMLGASAVSGFCASACSLPFDYVKTQIQKM
                        190       200       210       220       230
                     270       280       290       300       310       320
MOT pot prot     XVEPEMAPPYNGAIDCAMKTIKAEGPMALYKGFIPTISRQGPFTVVLFVTLEQVRKMLKD

PANICUM MOT      QPDANGKYPYTGSLDCVMKTLKSGGPFKFYTGFPVYCVRIGPHVMLTWIFLNQIQKFEKD
               240       250       260       270       280       290

MOT pot prot     F

PANICUM MOT      M
```

SEQ ID NO. 34

SEQ ID NO. 35

FIG. 20 genomic fragments in Vector pBK-CMV
MCS
ATG
BamHI
oligo2
MCS
oligo1
uni
cloning of the PCR fragments into pGemT
BamHI
XbaI
NotI
SmaI
Asp781
cloning into pBI101
as BamHI/XbaI fragments
GUS
noncoding region
promoter
MOT6P 2813 bp
MOT3P 1032 bp

Fig.25. (1/3)

GGATCCTTTC ACCTCCTAAT ACAAAAGTTT CCATTTTTTT AAGCAGGCAA
TGATAGTTTT TGTTAATGCT AATCTTTGTT ACCATATATG GTCTTTATCA
GAGCCTCCAG ACATCCGGAA CTGGTTCTCT AGCTATGTTT ATGAATCTCC
AAAAGTGGAT ACTATTCAAG ATTCCATACT TCCAGATCAT GAGAAAGAAT
TAGATGACAA AGTGTGTACG AATGGATACA GTGGCGGTGA GGAACCTCAG
AATTTTAGGA ATTCATTAGG AACTCCTTTT ATCCATGATG ACAAGTATGA
GCATCAAACT GCCTCAAAGG TAAACTTAGA ACCTTCAGCT GCATCAAACT
CCTTTCATAC ATCCTCTTGA TCTACATCAA TTCTTTGTGA ACTCATGCTT
TAGATGTTGA TTTATTGAAT GTACACTCAA AGTAAACGTA GAACCTTAAG
CTGTAGATCA ACAAACAGAT GGATTTTATC TTTCTGCGAT TGTACGAACC
TTTTTGGCTG GAGGGATCAG TACCTAGAAT ATACAATAAG ATTACATTGA
GTTACAGTGT TGGATCACAT AGTTGAACAT ATGTACAAAA CAAAGACAGA
AAGAAACATT AAAAGATCTA TTCTGTCTTT AGTTAGTTAG AAACTTAGGT
ATTTTCAGTT GGCTGGTAGC TATGCATATA AACCATCTCA TCTCCGATTC
TGTTAGTTAT ACAATTGTTT CTACCATGCA AAGAAGATAA CTGACACTTC
AGCTACATAA TTGAGGTCTA CCTTACCATA TTGTCATAAG TTCCCTTGAT
GATTTCCTTT GTGTTTGTAT GCTTCGAAGG ATCAGGAGGC TGATGGGACA
AAGAACGCAA GAATATCCAA TGAAATGTCT CATGAGAGAA TTTCTCAACA
GACACTAAAT CACAAGACAA CGGAGAACAC CAATTGTGGT TCACCAAGAT
ACATTGACAT GGTCTTCAAA GAGAGTGATG GAGAACACTT GGAGACCATT
TTTCCTCAAG AAGTTAACTG CAAAGTATCC TGCACCATCA ATCATTCTAG
CTGTGAAGGT GAAAAATTAT ACAGACATCC AATTCACAGG AAGGATTCTG
CAGAGAACAG TTCGAAATCT AAAGATAGTG TTGAACCTGC TGATGATGTG
CAATCTAAAA ATAGGATGGA GATGAGTGTG TTAAGTCAGA AGTTATCCAA
ACGGAAAGCA GCAGAAATCA TCGACAAAGA AAATCACATA AATGACTTTG
GAGAGAATGG TTTTATATCA ACCAGAAAGA GTAGAAATAG TCAAGTGCAG
AACAAAAGTC CTTTGCCAAC GCCAGCTGCA GTTCAGTCTC CTTTAAGTGG
AGTCACTGTT GCATCAAACT GCCACAAGCA GGGTTTGACT AGAAAGGTAC
TCACAGAAAC AACCAACTTG CATCCTAGTG CTTTGGAAAA AACAGGAAAA
TGGCGGTGCC CCCAAAGGAC TAAGCCAAAT ATTGGTCCTC CTCTAAAGCA
GCTTCGACTA GAGCAATGGG TTCGTCGAGC TTAAGTCTAA TACATTCTTA
TGAAGAGAAA ATGGATATCA AGAATGGTAG AATTCAAAAG AGGTTTGTGC
ATGTTAGCTA GTGAAAGATG TGAGAACAAG ACTTGGCACA ATGCTAGAGT
TACTATATCG TGGTTGTCAA TTTACAATGC AAATGAGATC TATTAAATTG

Fig.25. (2/3)

ACAACCACGA TATTTAGATT TTTTTTAATA GGTTTGGCCT TGAGTCTAAT
TTTGTTGGAC ATTCACATGA TCAAATAGAT TGAAGTATTT TTTAATTAGG
AGCGTTTCAA CTCACTTATT AGGTCTATTC GACACAAGTT TAGATTGATT
ATCTTCACTT GTTTCGGACA CCAAGTTATT AAACTGAAAA ATATAAAGGC
GAAATGGTCT GGTGGACCCT CATACTTGTA TGTGTTTGTT TTGTGAATCC
TTCTACTTGT TTCTTTGTCA TCTGAACCCT TGAACTCATC AAAACACAAT
ATTTTAAACA CGTTTTTTAC TACTCAAATG TGTGTGTATT ACAAATGCCT
GACACGTAAT TTTAAAAATA ATTATAAAAT GACACGTATA ATTATAAAAT
GACACATGTA TATATGATCA CTCCATGTCA TTTTTCCTTT TATTATATTT
GATTAATATA CCTACACTTT CTCTTTCCAA TTTTTATTTC TCTTTGTCAT
AGCCATCTGC ATCTGCATTT CCATTCCCAC AATCTCTTTT CAACTTTTTC
TTATCTTCCT TACCCTTTTC CTTTTTCCAA TCTCTTCTAC TCTTTCCATT
CAAGTAAAAA ATGTTGGTAC GATTTCTGAT TGTTCACAAT CTCGTCGAAG
TTCGGAGTTG ATTTTGGGTT CTGTTGGATT GGGATTTTGG TGGTGACCGG
TGGCGCTAAG GAAAAGTGGG GGTCTATTGG GTGGTCTGAT TGTTTCTAGT
TGTTCACAAC TAGCGGCGTT GTGAAAGTCG AGACTTATTG GCAGAGTTAG
TTTGGTGTTT TTGTCTTAGT TGTTGTTGTT GTTGGTTCTC ATTTATAGTT
GTTGGTTGAA GCTTGTCGGA GATGGTGAGA ACGAAGGCAA TTTGGTCGGA
GAAGGTGAGG AGGACGAGAA GAAGGCAATA AGTTTGAGTT TGGTTTGGAA
CTGAAACAAG GGGTCAATGT CAAATATATT TGAGTTTTTT TGTTTGATTT
TCAACTTATC TAGGTAGGTT TTCCAATTTA TTTTCGAATT TATTTGTTGT
TTAGTTTGGA TTTGATCTCT ATTTGTGTCT TTGTTTGATT TTGGGGTTTT
AGTCGATTAC ATTGATTTTG TTGATTTTTT TTGGGGATTT TGTATTTTTG
TGTCTAATGT TAGTGTAAGA TATTTTGGTA GTAGTGTTAT GCCTTCCATG
GCATTTTTCA TAAAAAAAAA AGAAGAGTTG TATAATAACA AGAAACGATA
GAGAAGAAAT TTGGGGGGAA AAGATCAAAA AAGAGGCCAA GAAAAGCTCA
AATTTTGTCC AACAATGGTG TTAGATGCAA ATAGGAAGAT GATGGCTTTA
CAAAGCCCTA ATGTCACTGT TAAACCCTTT TCCAAGGGTC TCACGCTCCT
AATAGGTGTG TGTCACACAC TCTTTGATAT TCACTGCCAC ATAGGATGTC
AAGTCAAAAA TAGTGTTTAA AATATTGTGT TTTGATAAGT TCAGGGGTTC
AGATGACAAA TGGGCAAGTA GAAGGGTTCA CAATACAAAC ATATACAAGT
ATAAGAGTCC ACCAGACCAT TTCSCCAAAT ATAAATAGAT GGGAAGTGTA
GATCTCCTCA AAATTCTTTT AGTAACAGTA AACACTCATA TACAAAAATA
TGTAATATGA AGTTATGTGC AACCAAATAA AATTTTAAAA ATTGAAACTT
TCTTTTTTTG TTTCCCACCC TATATATCAG GGACCACATT GGAGTCTGGA
TTAAATTTGA ATCGTGTATT GTAGGATCA TTTTCCAATA GAATTTTCTC

Fig.25. (3/3)

CATACTCCGG AAAAGTTGAA AACTTGCTCT TTTGATAAAA ATGTTGTTTA

AAAGGGAAAT ATATTTGAAA CAATCAAATG TGTTCCTGGA AAAGTATCTC

GTGTTAATAA CTTGCTAAAT ATTTAGCATT CTAATATACC TTTGAATTTA

AATTCTTCAT CTTGTGGTTT TTTTCAACTT TAAATATTCA AAATACTGGT

AAATTGATTT AGTGATCTAT TACAATTTTA GTTTTAGGT*C* *CAAT*CAAATC

TCTCCAACAT TTTATTTTTT ATTCTTAAAA TATTTCTTT*T* *ATAAAAT*TAT

ATTTTATTTA AATTGTAAAA A[+1] CAAACAAAC AAAAAATGAT AAA[+23]

*GAAAAAT AAGAAGACGA GGGTGCTAGA AAATGATAAA AACCCCCCCA*

*CCATAAAGCC CTTCCCATAA CTATATATAA AGAGGAGAAG GCG*[+113]

UBL1P: 3821 basepairs, 113 basepairs untranslated region

Fig.26.

GGATCCATTA GTTACACATT GTAGACTTTT AACTTTTCAA TGGCATAATT
CCTCACGTAA TCAAATAAAT AATTTTTTCT CTTTTCTATC TAACATTTTC
TCTTGAAAAA TATAAAGTAG TGGTAACTAT TGTCCAATTG TAATTCAAAT
ATGAGGCATC TTTTCATTAT ACAATCGACT TGAAGTAGAA TATTTATAAG
ATTTTATGCC TTATTGAGAA TCTAATTGTT ATAAATAGTT TATAAAAGTC
AATTTCTTTT AAATTTATTA TTCGTATCAG TTAAAAAAAT TATATCCCAA
CATTGTTATT CGTATTGTTA GTAAAAATTA ACTGCATGTC TGGCTTTTCT
TGAACATAGT TGATGATCTA TTGATGCGCG ATCTTCATTC ATTTGTTGAT
CTAATTATGC GTATAAATTA TAATCAAATA AAACGACATG TTTAAGTGGT
TAATTTGTCT ACGTAACAAA AAATTGAGTA TTCATACAAA AACTTAACAA
AAATTGAATC AAAATTATCT AATATAAACA TTTATATATT CAATCAGAAC
ATACCATACT TCAAATATCT AAATAGCTAA AAAATAATAA TACAAATGAA
GTGACCGGAT CAAGATTTTT GAGTTATATT ACACTTTTCA TTTATGGCTG
AGTCAAAATT TTCACTAAAA AATTCAAAAT TAACACGCAA TAAAACAAAA
CAAAATTCAA CACCTAAAAA GAGTCAAATG AATGAAAAAT CCCCTCGATC
CTACTTAACT CCGCCCCCAA CTTCCAACTT CATTATTACA ACCAAAAAAT
ATTTCCATTG ACCAAAGGCT CCTACTTTCC TTCCGCCGCA GAGAAAAGTA
TACTGAAAGA ACCCGCGTTG TATACAAAAC CTAATTTCCC TTTCCTTTCC
TTTCCCTTTC CCTTTTTTCC CTTATAAATT CGTTTCTTCC TCTTCCTTCT
CAACTCACAA TTTTATGTCT CACAGACTCA ACGTT *CCAC ACTTCGCATC*
*TATAGCTTTC GGTCTCCATT CCCATCTCCT GG*

1032 basepairs, 46 basepairs cDNA untranslated region

Fig.27. 1/2

GGATCTCATT TTCTAAACAT GCTTGAAATT TATGGTCTAA AATAAGTCAC
AGATGATTAT GCGGCTATAT AACAATATTT GCTTGAACTC CATTTTCGAA
CTTATCATCC GGAGTTAGGT GAGTCTAATT TGTTACTTCG GATCTTTGAT
AGATATGAAC TATCCTATTA GGCGTGGCAC AAGTCCATGT TTGGTTTGGG
TACCGCTATG TTGGACTTGA TTGAATTTTG ATCGTTGGAT ATCGCTTGAT
GATATATTCC AATGTTTAAA TTGAATTTTG ATTCATATGA ATTTTTAAAA
TCATCAAACA ATACATGACA AAGAACAAGT TCATATGCTA CATAGATGTG
TTTGGGCTTA ATTGACATAG ATTAAAGAAT AAATTTATAA TGCATTGAGT
TCAATGAGCT TAGTAATAAA TGTATGCACA AAGCCAATTG TATAAAAATG
TGCAAATTAC TCAACCAAAT CTAAAAATAA GACGACTTTA GACTAATTTT
ATAACATCTT AATTGACCAA GTCGACATGA TTTTATTTCA AACCACATAT
ATATGCTCTC TTTTTTTTAG AAAGAAAAAA TAAACAAATT TACACCCCAA
AGTTTTACTT GTGGGATAAA GTAGCTTTGG ACTTTCAAAA TTGTTGTTAT
AACCAGATAA ATGCTGATTT TCGTTTTTCA ATTTTGTCTT TATAAAGAAA
TGAATTTGGA TTCTAACTCA ATCATAAAAA TTAGTTAAGA GATGGGAATA
TTGTCTAAAC CATATTAAAG AGATCCCCAC CCCCACCCAC CGACTCGAAA
GCAAGAGGCA AGAGCGCAAC AACTACATGA AAGCCTTATG AGTAAGGTTA
ATCGAAGTCA GAAAAAGTTT ATTGGCAAGA GGGAATCAAA TATTTTAAAA
TATTTGGGTC CTCCACTCAT CAAAATTTAT ATGATATTTT TTCCTTTTTA
GTTCGTTTTA AAAAGAACAG AATCTTCTAT ATTTAGTAAC AACTTAACTT
TAACTTCACA TATTTTAGGT AAGTAAATTT CATATTTTTA CCATTAATAA
GATGATTTAT AGCCGCATAG ATATCTATGA CTTATTTTAA GCTATAAATT
TTAAAAATCT TTCTTTTATT CTTAAACTTC ATGCCGAAGC GAACACCTAA
AGAATAATAG TATTTTATTT AATCACAAAG AACAAGTAAC ACCATGTTAC
GTTAATATAG GAACAATATT ATATCATGCC CACCTCCAAA GGACAACAAA
AAAAGAAAGA AAAAAAAAAG TCAAAATGGC TTCTTAGCCA CCAAAAAAAA
GTTTTATTTA ATTAAAAGCT CTTTTTTAAT TTCACACGTT TAAGGGAGAA
TAATTCTAAG TAGAGTACTT TGACCTAAGA AATTTTGAAA AAGTCATAGT
CAAAACTATA AAAGTCAAAA AGAATTGAAT CCATTTTCAC ATAATTTTCA
ATATCACATT TAGTAATGAT TGATAAATTC AGTACTAAAA TAAATCAAAA
ATTCATAAAT TTAAGTTTGA CTTTGCTTCT CTTTAATAAA ATAATTTAAA
TGGTATGAAA TCATATTAAT CAGATCGATA AATTTAGAAT AGTAAATACA
TAAACAAAAG GTTTTATTTA TGGGATCATA AGTTGTTGCC TAGTAGGTAA
AGGAGCGTGT GCTAGGCACA TGCATAAGGG TCCTACAACT TCTACTACTA

Fig.27. 2/2

GTGAGCCCAT ATAAGTGAAA CTCGAAGATT GTTCTCATTT AATAATATCT
TATTCTTCGT TTATATTATT ATTTGTATTT TTTTTCTTCG ATTATCGTAT
TATATATATT GCTCACTATG TTCAGCATAA CTGCTTCATT GTTGTATTTC
CCTTTTCATA CTTGATTTTA TTATTCTTTA AGCCGAGAGT CTATTGTCCA
ATTGTAATTT AAATATGAGG CCTCTTTTGA TTATACAATT GACATTTTAA
GTAGAATATG TTTTGAGAAT CTAATTGTTA TAAATAGCGT ATAAAAGTCA
ATTTCTTTTA AGTTCATTAT TTGTGTCAGT AAAAAAAAAA AACTATATTT
CAAAATTGTT ATTCGTACTG TTGTTAGTAA AAAATAACTG CATGTCTGGC
TTTTCTTGAA CGGTCTATTG ATGCGCGATC TTCATCCATT TGCTGATCTA
ATTATGCGTA TAAATTATAA TAAAAATAAA ACGACATATT TTAAGTGGTT
AATTTGTCTA CGTAACAAGC AATTGAGTAT TCATACAAAA ACTTAACAAA
ATTTGAATTA AAATTATCTA ATATAAGCAT TTATATCATA TATTTAAGTA
TTCAATCAGA GCATACCATA TTTCAAATAT CTAAATAGCT AAAAAAAAAT
ACAAATGAAG TGACTGGGTC AAGATTTTTG TGTTATATTA CATTTTCCAT
GTGTGGACGT CTGAGTCAAA ATTTTCACTA AACAATCACA AAACACAAAA
CAAAATTCAA CACCTAAAAA GAGTCAAATA AATGAAAAAT CCCCTCGATC
CGACTTAACT CCCCCCCGAC TTCTAACTTC ATTATTACAA CCAAAAAATA
TTTCCATTGA CCAAAGGCCC CCACTTTCCT TCCGCCGCAG AGAAAAGTAT
ACTGAAAGAA CCCGCGTTGT ATACAAAACC TAATTTCCCT TTCCTTTCCT
TTCCCTTCCC TTTTTCCCTT ATAAATTCGC TTCTTCCTCT TCCTTCTCAA
CTCACAATTT ATATGTCTCA CAGACTCAAC GTT *CCACACT TCGCATCTAT*
*AGCTTTCGGT CTCCATTCCC ATCTCCTGGT TTCCAGTGAG ATGAACTCTA*
*ATTCCAATTG GGC*

2813 basepairs, 80 basepairs of the cDNA untranslated region

GENETIC METHOD FOR CONTROLLING SPROUTING

The present invention relates to a method of controlling sprout formation in plants and parts thereof including vegetative storage organs.

Potato tubers are of major economic importance. They represent a carbohydrate resource for many diets and are used as a basis for a variety of processed products. Besides starch, tubers contain high-quality proteins, substantial amounts of vitamins, minerals and trace elements. Continuous production of potato tubers throughout the year is impossible in most regions where potatoes are grown. As a consequence storage of the harvested tubers is required.

One of the potentially most damaging phenomena during storage is premature sprouting. Long term storage involves cooling, forced ventilation and use of chemical sprouting suppressants. The problems directly linked to long term storage are manifold.

Cooling, usually done in Northern Europe by ventilation with air at ambient temperature is one of the methods to inhibit sprouting. Apart from the associated costs, longer term cooling at 4° C. gives rise to the problems of cold sweetening and melanisation (darkening).

Chemical sprouting suppressants are currently the only possibility for inhibiting sprouting in potatoes destined for processing and fresh consumption, since low temperature storage leads to unacceptable accumulation of reducing sugars. However, in recent years, questions have arisen as to the environmental and nutritional impact of chemical suppressants such as chlorinated hydrocarbons. There is therefore a real need for an alternative method of controlling sprouting in vegetative storage organs such as tubers.

An alternative approach to delay sprouting would be the use of transgenic plants with a prolonged quiescence period. Sprouting of potato tubers involves several independent steps which might be targets for genetic engineering. The first step is the mobilisation of reserves, mainly starch. Starch breakdown occurs in amyloplasts and is mediated by starch phosphorylase and/or amylases. In the next step following starch breakdown, the resultant hexoses and/or hexose-phosphates have to be exported from amyloplasts. After transfer into the cytosol the produced hexoses and hexose-phosphates are distributed between glycolysis and sucrose synthesis. The third step is the formation of sucrose in the cytosol. Sucrose synthesis is energy dependent thus glycolysis and respiration are required. The fourth step is the transport of sucrose to the developing sprout. Finally the imported sucrose is utilised in the sprout to support growth and development.

We have now developed a means of controlling sprouting in vegetative storage organs such that sprouting may be turned off and on without any undesirable side effects such as yield loss. This new method involves the targeted expression of genes resulting in the disruption of sprouting in combination with gene switch technology to restore sprouting when required.

According to a first aspect of the present invention there is provided a method for the selective induction or suppression of sprouting in a plant comprising incorporating, preferably stably incorporating, into the genome of said plant by transformation a DNA construct comprising a first polynucleotide sequence comprising at least one DNA sequence operably linked to a tissue or organ selective promoter region and optionally to a transcription terminator region and a second polynucleotide sequence comprising at least one DNA sequence operably linked to and controlled by a controllable promoter region and optionally to a transcription terminator region whereby the DNA sequence(s) in said first polynucleotide sequence is expressed during dormancy of the vegetative organ derived from said transgenic plant resulting in effective suppression of sprouting and the said suppression is neutralised by inducing expression of the DNA sequence(s) in said second polynucleotide sequence from said controllable promoter region by external application of an inducing substance such that restoration of sprouting of said vegetative storage organ is dependent on the application of the inducer.

As used herein the term "tissue or organ selective promoter region" denotes those promoter regions which yield preferential expression of the DNA sequence(s) of interest in the desired tissue or organs.

The DNA sequences in the DNA construct may be endogenous or heterologous with respect to the transformed host.

Examples of DNA sequences which may be used in the method of the present invention to control sprouting include those DNA sequences coding for proteins involved in the mobilisation of reserves during dormancy such as the breakdown of storage compounds e.g starch breakdown, i.e starch phosphorylase, amylase (e.g. $\alpha$ or $\beta$ amylase) and maltase; e.g in glycolysis and subsequent metabolism e.g phosphofructokinase, hexokinase; in sucrose biosynthesis e.g sucrose synthase; in the transport of reserves during dormancy such as in phloem loading e.g ATPase; in long distance phloem transport and in phloem unloading e.g inorganic pyrophosphorylase (iPPase); and in the utilisation of reserves during dormancy such as in assimilate breakdown e.g the breakdown of sucrose in the growing sprout, i.e invertase; and in the utilisation of assimilates e.g utilisation of sucrose-derived metabolites, in the provision of energy required for sprout formation e.g. DNA sequences coding for proteins involved in mitochondrial function such as in respiration, such as mitochondrial enzymes and transport proteins such as translocators e.g. adenine nucleotide translocator (ANT) and malate oxoglutarate translocator (MOT) and inhibitors thereof such as uncoupling proteins. Examples of useful DNA sequences also include any other sequences which are involved in potato sprouting Examples of preferred DNA sequences which may be used in the method of the present invention to control sprouting include those resulting in the production of sense, anti-sense or partial sense sequence(s) to, and/or coding for, proteins involved in the mobilisation and/or utilisation of sucrose, in potato sprouting and in mitochondrial function such as in respiration.

Examples of particularly preferred DNA sequences include those coding for an invertase derived from plant, bacterial or fungal sources e.g. from yeast, a pyrophosphatase derived from plant, bacterial or fungal sources and proteins involved in mitochondrial function such as MOT and ANT derived from plant, bacterial or fungal sources which are described hereinafter.

Suppression of sprouting may be achieved in a variety of ways. The first DNA sequence(s) may be expressed during dormancy of the vegetative storage organ and then down-regulated when sprouting is desired. When sprouting is desired expression of the second DNA sequence(s) is turned on leading to down regulation of the first DNA sequence and consequently restoration of sprouting.

Down regulation of a desired DNA sequence(s) may be achieved using methods well known in the art such as, for example, by use of repressor proteins, sense, anti-sense, partial-sense, and expression of a complementary protein. Examples of suitable operator/repressor systems include for example the lac, tet or lambda 434 systems and mutants thereof such as the Lac IΔ His mutant (Lehming, N., Sartoris, J., Niemoeller, M., Genenger, G., v. Wilcken-Bergman, B. and Muller-Hill, Benno (1987), EMBO J. 6(10) 3145–3153—where the mutant has a change in amino acid 17 of Lac I altering tyrosine for histidine). Alternatively, an Amplicon™ may be used to down-regulate genes (Angell, S. M., Baulcombe, D. C., (1997) 16, 3675–3684). In this regard, the cDNA of replicating potato virus (PVX) RNA which has a transgene inserted therein is used whereby transiently expressed RNA sharing homology with the transgene is suppressed.

Alternatively, expression of the DNA sequence(s) in the first polynucleotide sequence may result in the production of a sense, anti-sense or partial-sense sequence(s) which acts to suppress a gene involved in sprouting or in the expression of an Amplicon™. In this case sprouting is restored by switching on expression of the DNA sequence(s) in the second polynucleotide sequence which results in production of the protein or a corresponding protein to that, the production of which was suppressed by the sense, anti-sense or partial-sense sequence(s) in the first DNA sequence. Sprouting may also be restored by means of a suitable operator/repressor system.

Where either or both of the polynucleotide sequences in the construct comprise more than one DNA sequence it is preferable that they are not identical to avoid any co-suppression effects.

Expression of the DNA sequence(s) in the first polynucleotide sequence is under the control of a tissue or organ selective promoter to ensure targeted expression of the DNA sequence whereby expression is induced in an organ or tissue specific manner. Examples of tissue selective promoters include phloem selective promoters e.g. the rolC promoter, and examples of organ selective promoters include tuber specific promoters, such as the patatin promoter. The use of tissue or organ selective promoters such as the rolC and tuber promoters is particularly preferred.

The DNA sequence(s) in the second polynucleotide sequence of the construct is under the control of a controllable promoter region.

As used herein the term "controllable promoter region" includes promoters which may be induced chemically. The use of a promoter sequence which is controlled by the application of an external chemical stimulus is most especially preferred. The external chemical stimulus is preferably an agriculturally acceptable chemical, the use of which is compatible with agricultural practice and is not detrimental to plants or mammals.

The controllable promoter region most preferably comprises an inducible switch promoter system as such as, for example, a two component system such as the alcA/alcR gene switch promoter system described in our published International Patent Application No. WO 93/21334; the GST promoter as described in our published International Patent Application Nos. WO 90/08826 and WO 93/031294; and the ecdysone switch system as described in our published International Patent Application No. WO 96/37609, the teachings of which are incorporated herein by reference. Such promoter systems are herein referred to "switch promoters". The switch chemicals used in conjunction with the switch promoters are agriculturally acceptable chemicals making this system particularly useful in the method of the present invention. In the case of the alcA/alcR promoter switch system the preferred chemical inducer is ethanol in either liquid or more preferably in the vapour form. One of the main advantages of the use of ethanol vapour is that only small quantities of ethanol are required and that high levels of expression are achieved. Full details of switch chemicals are provided in the patent applications listed immediately above.

Suitable transcription terminators which may be used are also well known in the art and include for example the nopaline synthase terminator and octopine synthase terminators. The promoter is most desirably a late tuber specific promoter which is active late in the dormancy period i.e just before sprouting.

The controllable promoter region for use in the method of the present invention is preferably the GST or alcA/alcR promoter switch system. Restoration of sprouting is preferably achieved using switchable antisense or switchable sense or partial sense methods as is described more fully herein or alternatively by use of an Amplicon™ or by means of a suitable operator/repressor system. Down-regulation of gene activity due to partial sense co-suppression is described in our International Patent Application No. WO 91/08299 the teachings of which are incorporated herein and this may be avoided if necessary by using gene sequences derived from different organisms.

According to a second aspect of the present invention there is provided a DNA construct comprising a first polynucleotide sequence comprising at least one DNA sequence operably linked to a tissue or organ selective promoter region and optionally to a transcription terminator region and a second polynucleotide sequence comprising at least one DNA sequence operably linked to and controlled by a controllable promoter region and a transcription terminator region wherein said first polynucleotide sequence comprises a DNA sequence coding for a protein involved in mobilisation and/or utilisation of sucrose and said second polynucleotide sequence comprises a DNA sequence which is a sense, an anti-sense or partial sense sequence corresponding to said protein or a DNA sequence which is capable of causing suppression of said protein.

According to a third aspect of the present invention there is provided a DNA construct comprising a first polynucleotide sequence comprising at least one DNA sequence operably linked to a tissue or organ selective promoter region and optionally to a transcription terminator region and a second polynucleotide sequence comprising at least one DNA sequence operably linked to and controlled by a controllable promoter region and a transcription terminator region wherein said first polynucleotide sequence comprises a first DNA sequence coding for a protein involved in mobilisation and/or utilisation of sucrose and a further DNA sequence coding for an operator sequence operably linked to the first DNA sequence and the second polynucleotide sequence comprises a DNA sequence coding for a repressor protein capable of binding to said operator sequence.

According to a fourth aspect of the present invention there is provided a DNA construct comprising a first polynucleotide sequence comprising at least one DNA sequence operably linked to a tissue or organ selective promoter region and optionally to a transcription terminator region and a second polynucleotide sequence comprising at least one DNA sequence operably linked to and controlled by a controllable promoter region and a transcription terminator region wherein said first polynucleotide comprises a DNA sequence(s) which is a sense, anti-sense or partial sense sequence corresponding to a protein involved in potato sprouting or a DNA sequence which is capable of causing suppression of a protein involved in potato sprouting and said second polynucleotide sequence comprises a DNA sequence(s) coding for a protein involved in potato sprouting.

According to a fifth aspect of the present invention there is provided a DNA construct comprising a first polynucleotide sequence comprising at least one DNA sequence operably linked to a tissue or organ selective promoter region and optionally to a transcription terminator region and a second polynucleotide sequence comprising at least one DNA sequence operably linked to and controlled by a controllable promoter region and a transcription terminator region wherein said first polynucleotide comprises a first DNA sequence(s) which is a sense, anti-sense or partial sense sequence corresponding to a protein involved in potato sprouting or a DNA sequence which is capable of causing suppression of a protein involved in potato sprouting and a further DNA sequence coding for an operator sequence operably linked to the first DNA sequence and said second polynucleotide sequence comprises a DNA sequence(s) coding for a repressor protein capable of binding to said operator sequence.

According to a sixth aspect of the present invention there is provided a DNA construct comprising a first polynucleotide sequence comprising at least one DNA sequence operably linked to a tissue or organ selective promoter region and optionally to a transcription terminator region and a second polynucleotide sequence comprising at least one DNA sequence operably linked to and controlled by a controllable promoter region and a transcription terminator region wherein said first polynucleotide comprises a DNA sequence(s) which is a sense, anti-sense or partial sense sequence corresponding to a protein involved in mitochondrial function or a DNA sequence which is capable of causing suppression of a protein involved in mitochondrial function and said second polynucleotide sequence comprises a DNA sequence(s) coding for a protein involved in mitochondrial function.

According to a seventh aspect of the present invention there is provided a DNA construct comprising a first polynucleotide sequence comprising at least one DNA sequence operably linked to a tissue or organ selective promoter region and optionally to a transcription terminator region and a second polynucleotide sequence comprising at least one DNA sequence operably linked to and controlled by a controllable promoter region and a transcription terminator region wherein said first polynucleotide comprises a first DNA sequence(s) which is a sense, anti-sense or partial sense sequence corresponding to a protein involved in mitochondrial function or a DNA sequence which is capable of causing suppression of a protein involved in mitochondrial function and a further DNA sequence coding for an operator sequence operably linked to the first DNA sequence and said second polynucleotide sequence comprises a DNA sequence(s) coding for a repressor protein capable of binding to said operator sequence.

We have found the following combination of DNA sequences to be particularly suitable for use in the method of the invention: by placing a DNA sequence coding for an invertase under the control of a phloem selective promoter such as the rolC promoter, it is possible to target expression of the DNA sequence to the phloem and effectively repress sprouting and to then restore sprouting by switching on a DNA sequence coding for invertase anti-sense using the alcA/alcR chemical switch promoter. Sucrose concentration in the phloem from the leaf is so high that the effects of invertase expression are effectively swamped avoiding any unwanted side effects. This contrasts with the situation in the sprout phloem where expression of invertase has a dominant effect with the result that sucrose is broken down and sprouting is effectively inhibited.

A further useful combination is a DNA sequence coding for an inorganic pyrophosphatase (iPPase) under the control of a tuber promoter. Uptake of sucrose and transport in the phloem is an energy requiring process and by inhibiting the provision of energy by expressing the DNA sequence coding for inorganic pyrophosphatase it is possible to inhibit the uptake process. The inhibition can be reversed by using, for example, an alcA/alcR chemically induced switch promoter to switch on a DNA sequence coding for an antisense, sense or partial sense sequence to iPPase and sprouting is restored. Again the use of a tissue or organ selective promoter ensures that the inhibition of sucrose uptake and transport in the phloem does not occur in the whole plant but only in the tuber thereby minimising any deleterious effects in the plant.

In both cases, an alternative means of restoring sprouting is by the use of an Amplicon™ where transiently expressed RNA sharing homology with the transgene is suppressed. Such a transgene could, for example, be a cDNA for an invertase or iPPase. A further alternative means of restoring sprouting is by the use of a suitable operator/repressor system.

We have also found that by selectively inhibiting the provision of energy required for sprout growth and development in the tuber by placing a DNA sequence coding for sense, antisense or partial sense to a DNA sequence coding for a protein involved in mitochondrial function, such as the adenosine nucleotide translocator protein (ANT) or mitochondrial oxoglutarate translocator (MOT), under the control of a tuber selective promoter sprouting may be inhibited without unwanted side effects. Alternatively, a DNA sequence which causes suppression of such proteins may be used. One way in which reversal of the inhibition may be achieved is by switching on expression of a second DNA sequence the product of which is complementary to the first DNA sequence, for example a DNA sequence coding for ANT derived from a different source preferably from Arabidopsis may be used to counteract the effect of the ANT antisense expression. In the case of MOT a suitable complementary sequence may be derived from *Panicum miliaceum* as is described by Taniguchi and Sugiyama in Plant Molec. Biol. 30, 51–64 (1996). Alternatively, a suitable operator/repressor system may be used to reverse inhibition. As above the alcA/alcR chemical switch promoter may be used. The above examples are described more fully herein.

According to some embodiments of the present invention the first polynucleotide sequence comprises a further DNA sequence coding for an operator sequence operably linked to the first DNA sequence and the second polynucleotide sequence comprises a DNA sequence coding for a repressor capable of binding to the operator sequence under the control of a switch promoter such that application of the inducer results in expression of the DNA sequence coding for the repressor which subsequently binds to the operator and expression of the first DNA sequence in the first polynucleotide sequence is switched off. An example of such a system is the lactose operator and repressor protein as is described in published International patent Application No. WO 90/08830. Other examples include the tetracycline and lambda 434 operator/repressor systems.

Plant cells may be transformed with recombinant DNA constructs according to a variety of known methods for example, Agrobacterium Ti plasmids, electroporation, microinjection and by microprojectile gun. The transformed cells may then, in suitable cases, be regenerated into whole plants in which the new nuclear material is incorporated, preferably stably incorporated, into the genome. Both transformed monocotyledonous and dicotyledenous plants may be obtained in this way.

According to an eighth aspect of the present invention, there is provided a plant cell transformed with any one of the DNA constructs defined above.

According to a nineth aspect of the present invention there is also provided a whole plant transformed with a DNA construct according to the above aspects of the present invention wherein said DNA construct is incorporated, preferably stably incorporated, into the genome of said plant.

The invention still further includes, according to a tenth aspect of the present invention, progeny of the plants of the preceding paragraph which progeny comprise a DNA construct according to the above aspects of the present invention incorporated, preferably stably incorporated, into their genome and the seeds and tubers of such plants and such progeny.

The method of the present invention is particularly suitable for controlling sprouting in potato tubers.

In a preferred embodiment the invention provides a method for the selective induction or suppression of sprouting in potatoes comprising stably incorporating into the genome of said potato by transformation a DNA construct comprising a first polynucleotide sequence comprising at least one DNA sequence operably linked to a tissue or organ selective promoter region and optionally to a transcription terminator region and a second polynucleotide sequence comprising at least one DNA sequence operably linked to and controlled by a controllable promoter region and optionally to a transcription terminator region whereby the DNA sequence(s) in said first polynucleotide sequence is expressed during dormancy of the tuber derived from said transgenic potato resulting in effective suppression of sprouting and the said suppression is neutralised by inducing expression of the DNA sequence(s) in said second polynucleotide sequence from said controllable promoter region by external application of an inducing substance such that restoration of sprouting of said tuber is dependent on the application of the inducer.

We have also identified five particularly preferred DNA sequences which we believe may also be especially useful in the method of the present invention. We have identified these DNA sequences as being induced during tuber storage and we have designated these as 16-3 (sequence 2), 16-8 (sequence 3), 10-1 (sequence 4) and AC4 (sequence 5), M-1-1 (MOT) (sequence in FIG. 19) and a MOT variant (sequence 6—having an EMBL Accession number X99853). The DNA sequences and their isolation are described fully in the accompanying examples. The present invention therefore provides, according to a further aspect, the use of all or part of the DNA sequences from clones 16-3, 10-1, AC4, 16-8, M-1-1 and the MOT variant in a method according to the invention to control sprouting in plants.

The DNA sequences of 16-3, 16-8, AC4 and M-1-1 are believed to be new and a twelfth aspect of the present invention extends to polynucleotides comprising nucleotides 1 to 870 in sequence 2 (corresponding to 16-3), nucleotides 1 to 712 in sequence 3 (corresponding to 16-8) or nucleotides 1 to 386 in sequence 5 (corresponding to AC4) or nucleotides 1 to 1351 in sequence FIG. 19 (corresponding to M-1-1 encoding a MOT) and further to the protein products encoded thereby and to those proteins having a substantially similar activity and having an amino acid sequence which is at least 85% similar to the said product. It is preferred that the degree of similarity is at least 90% and it is more preferred that the degree of similarity is 95% and it is most preferred that the degree of similarity is 97%.

A particularly preferred embodiment of the polynucleotides consists of nucleotides 55 to 751 in sequence 2, nucleotides 87 to 473 in sequence 3, and to nucleotides 192 to 164 in FIG. 19 and further to the translation products encoded thereby and to those proteins having a substantially similar activity and having an amino acid sequence which is at least 85% similar to the said product. It is preferred that the degree of similarity is at least 90% and it is more preferred that the degree of similarity is 95% and it is most preferred that the degree of similarity is 97%.

As used herein the term "degree of similarity" is used to denote sequences which when aligned have similar (identical or conservatively replaced) amino acids in like positions or regions, where identical or conservatively replaced amino acids are those which do not alter the activity or function of the protein as compared to the starting protein. For example, two amino acid sequences with at least 85% similarity to each other have at least 85% similar (identical or conservatively replaced amino residues) in a like position when aligned optimally allowing for up to 3 gaps, with the proviso that in respect of the gaps a total of not more than 15 amino acid resides is affected. The degree of similarity may be determined using methods well known in the art (see, for example, Wilbur, W. J. and Lipman, D. J. "Rapid Similarity Searches of Nucleic Acid and Protein Data Banks." Proceedings of the National Academy of Sciences USA 80, 726–730 (1983) and Myers E. and Miller W. "Optimal Alignments in Linear Space". Comput. Appl. Biosci. 4:11–17(1988)). One programme which may be used in determining the degree of similarity is the MegAlign Lipman-Pearson one pair method (using default parameters) which can be obtained from DNAstar Inc, 1228, Selfpark Street, Madison, Wis., 53715, USA as part of the Lasergene system.

According to a thirteenth aspect of the present invention there is provided polynucleotide sequence(s) encoding a protein having a substantially similar activity to that encoded by nucleotides provided in sequences 2, 3 and 5 and FIG. 19, which polynucleotide is complementary to one which still hybridises with the sequence comprised by that provided in sequences 2, 3 or 5 or FIG. 19 when incubated at or between low and high stringency conditions. In general terms, low stringency conditions can be defined as 3×SSC at about ambient temperature to about 65 C. and high stringency conditions as 0.1×SSC at about 65° C. SSC refers to the buffer 0.15M NaCl, 0.015M trisodium citrate and 3×SSC is three times as strong as SSC and 0.1×SSC is one tenth of the strength of SSC.

The invention further provides polynucleotide sequence (s) encoding a protein having a substantially similar activity to that encoded by nucleotides 55 to 751 in sequence 2, nucleotides 87 to 473 in sequence 3, or to nucleotides 192 to 1164 in FIG. 19, which polynucleotide is complementary to one which still hybridises with the sequence comprised by nucleotides 55 to 751 in sequence 2, nucleotides 87 to 473 in sequence 3, or to nucleotides 192 to 1164 in FIG. 19 when incubated at or between low and high stringency conditions. In general terms, low stringency conditions can be defined as 3×SSC at about ambient temperature to about 65 C. and high stringency conditions as 0.1×SSC at about 65° C. SSC refers to the buffer 0.15M Na Cl, 0.015M trisodium citrate and 3×SSC is three times as strong as SSC and 0.1×SSC is one tenth of the strength of SSC.

The polynucleotides according to the present invention depicted in sequences 2, 3 and 5 and FIG. 19 may be operably linked to a promoter region which may be homologous or heterologous to the polynucleotide and the present invention extends to such constructs. The present invention also extends to a DNA construct comprising said polynucleotides further comprising a region encoding a peptide which is capable of targeting the translation products of the polynucleotide to desired cellular or sub-cellular locations. The invention further provides a vector comprising said polynucleotide sequence as described in sequences 2, 3, 5 and FIG. 19 preferably operably linked to a promoter region and optionally to a transcription terminator and or a targeting sequence as described above.

The sequences provided herein for 16-3 (SEQ ID NO. 2), 16-8 (SEQ ID NO. 3), 10-1 (SEQ ID NO. 4), AC-4 (SEQ ID NO. 5), M1-1 (SEQ ID NO. 27) and the MOT variant are cDNA sequences and may, according to a further aspect of the present invention, be used as probes for the isolation and identification from genomic libraries of sequences upstream of the 5' region which contain the natural promoter region. The promoter region may then be identified, isolated and sequenced.

According to a fifteenth aspect of the present invention there is provided a host cell transformed with a DNA construct comprising a polynucleotide sequence as described in sequences 2, 3 and 5 and FIG. 19 or a vector described above comprising said polynucleotide sequence. The host cell is preferably a plant cell as described previously and the present invention extends also to whole plants having incorporated, preferably stably incorporated, into their genome a polynucleotide sequence, DNA construct or vector as described above, and to seeds, tubers and progeny of said plants.

According to a sixteenth aspect of the present invention there is provided a DNA construct comprising a polynucleotide sequence comprising a switch promoter system operably linked to a polynucleotide sequence comprising a sense, antisense or partial sense transcription construct wherein when expression of said polynucleotide sequence is switched on from the switch promoter the resulting expression of said sense, antisense or partial sense sequence leads to down regulation of the expression of a further polynucleotide sequence encoding a transgene.

In a seventeenth aspect the present invention provides a method of controlling the expression of a transgene comprising transforming a host cell with a DNA construct comprising a switch promoter system operably linked to a polynucleotide sequence comprising a sense, antisense or partial sense transcription construct, and a further DNA construct comprising a coding sequence coding for a transgene and controlling expression of the polynucleotide sequence from said switch promoter such that the resulting expression of the said sense, antisense or partial sense construct leads to down regulation of the expression of said transgene.

As used herein the term "transgene" is used to denote a gene which is foreign or heterologous to the transformed host cell.

In a preferred embodiment of the above aspects the present invention provides a DNA construct comprising the alcA/alcR switch promoter operably linked to a polynucleotide sequence comprising a sense, antisense or partial sense transcription construct.

The present invention also extends to a vector comprising said DNA constructs according to the above aspects of the invention.

According to an eighteenth aspect of the present invention there is provided a host cell transformed with a DNA construct comprising a polynucleotide sequence comprising a switch promoter which may be switched on by the application of a chemical stimulus operably linked to a polynucleotide sequence comprising a sense, antisense or partial sense transcription construct wherein when expression of said polynucleotide sequence is switched on from the switch promoter the resulting expression of said sense, antisense or partial sense sequence leads to down regulation of the expression of a further polynucleotide sequence encoding a transgene.

The host cell is preferably a plant cell as described previously and the present invention extends also to whole plants derived therefrom having incorporated, preferably stably incorporated, into their genome a polynucleotide sequence, DNA construct or vector as described above, and to seeds, tubers and progeny of said plants.

The use of switch promoter systems to control expression of the sense, antisense or partial sense construct has many applications. Down-regulation of a gene, the expression of which gives rise to a lethal or inhibitory effect may be controlled using switchable sense, antisense or partial sense to facilitate the identification of suitable herbicide targets. Switchable down regulation using sense, antisense or partial sense sequences may also be used to identify mechanisms of cell ablation.

The present invention therefore provides according to a nineteenth aspect a method of identifying a site which may be a suitable target for interaction with a herbicide comprising the steps of transforming a plant with a polynucleotide sequence comprising a first DNA sequence which is capable of affecting the expression of DNA at said target site wherein expression of said first DNA sequence is under the control of a switch promoter; controlling expression of said DNA sequence from said switch promoter such that the expression of the DNA coding for the herbicide target site is down regulated and determining the effects of said down regulation on the plant viability.

The types of effects which would be monitored include the time period for which down regulation at the target site must be maintained and what level of down regulation is required and on the basis of the results obtained it can be decided whether the target site would be suitable as a target site for a herbicide.

We have most unexpectedly found that the STLS-1 leaf promoter sequence acts as an enhancer of gene expression in tubers and the use of the STLS-1 sequence as an enhancer of gene expression in tubers forms a further aspect of the present invention.

In a twentieth aspect the present invention therefore provides a method of enhancing gene expression in tubers comprising transforming a tuber plant cell with a polynucleotide sequence comprising a DNA sequence coding for all or part of the STLS-1 leaf promoter operably linked to a further promoter region.

The STLS-1 leaf promoter is known in the art (Eckes et al (1986) Mol. Gen. Genet. 205, 14–22) and is described in the accompanying examples. All or part of the DNA sequence coding for the STLS-1 leaf promoter may be used as an enhancer according to the invention. Active fragments of STLS-1 may be identified using techniques well known in the art such as restriction enzyme digestion followed by analysis of enhancement of gene expression of the fragments thus obtained. The STLS-1 promoter sequence may be inserted either upstream i.e. at the 5' end or downstream i.e. at the 3' end of the further promoter region. Insertion of the STLS-1 sequence upstream of the promoter region is especially preferred. In a particularly preferred embodiment of this aspect of the invention the STLS-1 sequence is inserted upstream of the 35S CaMV promoter.

In a twenty-first aspect the present invention provides tubers, which are preferably potato tubers, derived from transgenic plants which do not sprout unless treated with a chemical inducer.

According to a twenty-second aspect of the present invention, there is provided a polynucleotide sequence comprising all or part of at least one of the sequences depicted in FIG. 25, 26 or 27 and polynucleotides having the same function as the sequence which is depicted in FIG. 25, 26 or 27 which polynucleotide is complementary to one which still hybridises with the sequence comprised by that provided in FIG. 25, 26 or 27 when incubated at or between low and high stringency conditions. Such sequences are preferably tuber specific promoters.

According to a twenty-third aspect of the present invention, there is provided a method of controlling gene expression of a plant or a part thereof comprising transforming a plant cell with a chemically inducible plant gene expression cassette comprising a first promoter operatively linked to a regulator sequence derived from the alc R gene and a controllable promoter derived from the alc A gene promoter operatively linked to a target gene, wherein the controllable promoter is activated by the regulator protein in the presence of alcohol vapour thereby causing expression of the target gene.

The present invention will now be described by way of the following non-limiting examples and with reference to the accompanying figures in which:

FIG. 1: (SEQ ID NOS.: 9, 20, 21, and 22, respectively) shows a diagram of the construction of plasmid pBIN-IN8.

Figure 2:
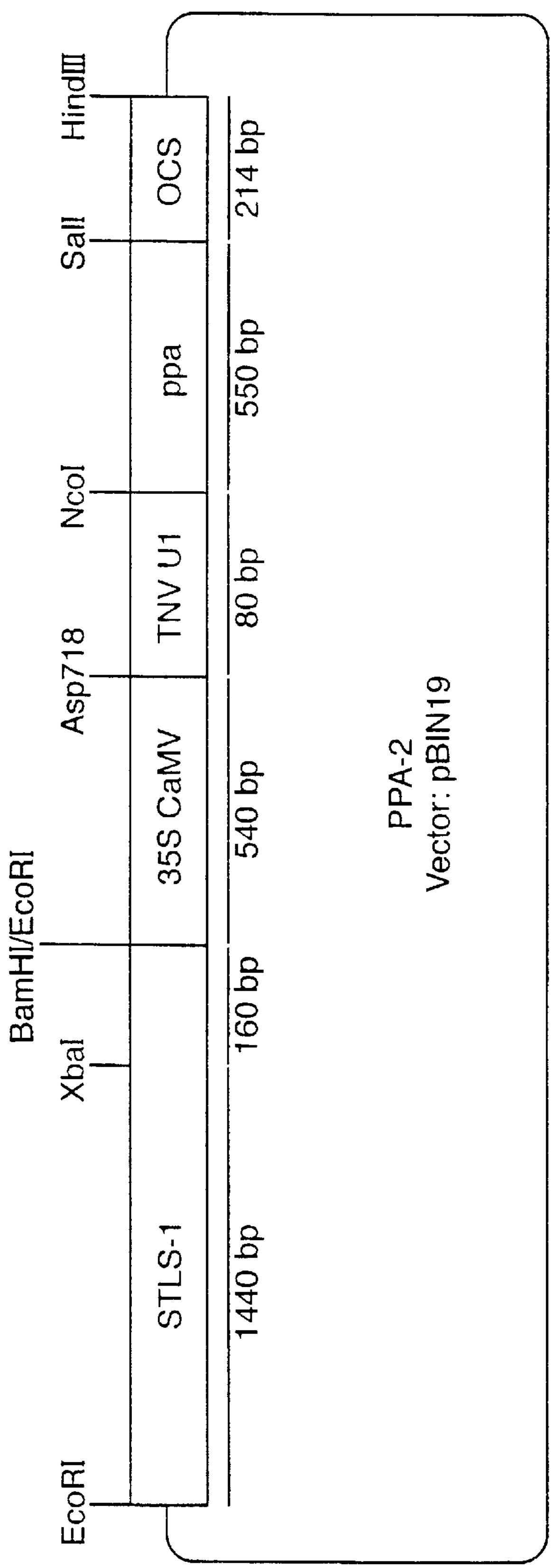

FIG. 2: shows a schematic drawing of plasmid PPA-2.

Figure 3:
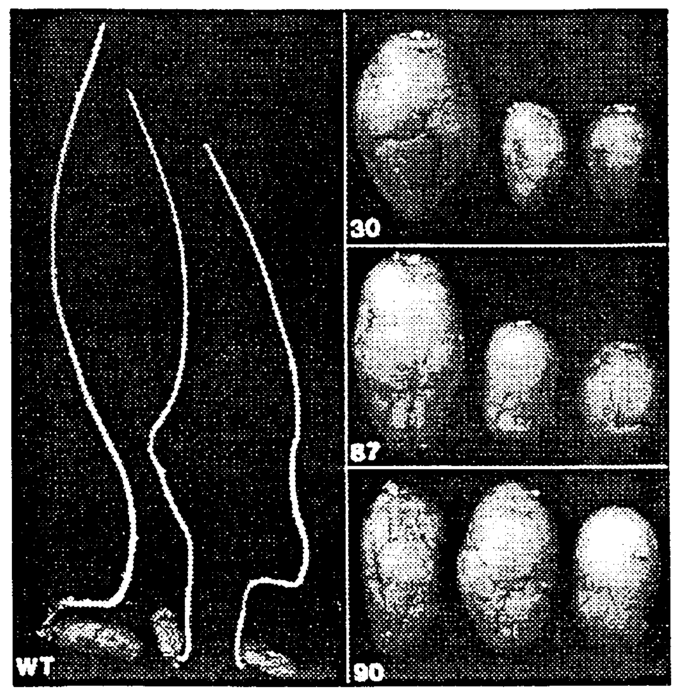

FIG. 3: shows a photograph of wild type (Desiree) and transgenic potato plants containing the phloem specific cytosolic invertase (genotype DIN-87, DIN-90 and DIN-30) following prolonged storage in the dark at room temperature.

Figure 4:
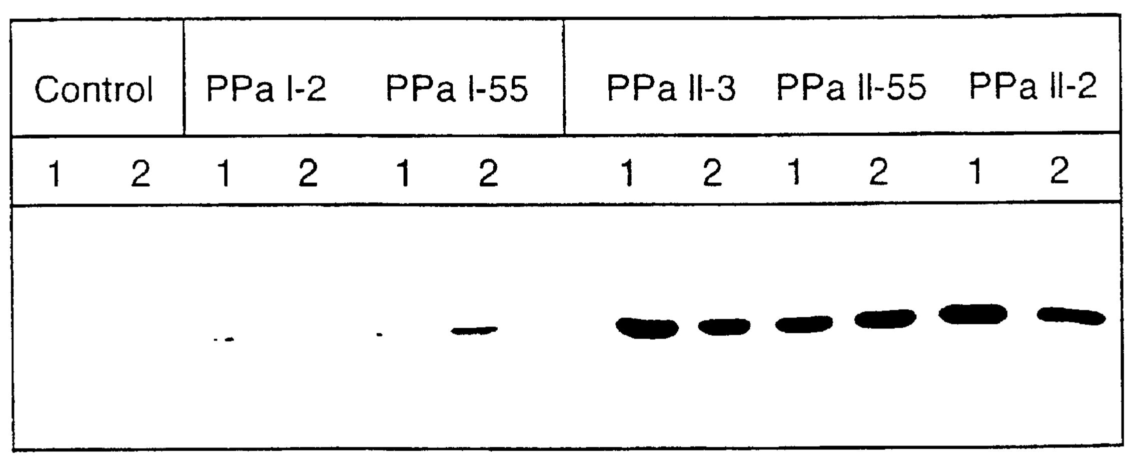

FIG. 4: shows western blot analysis of protein extracts from potato tubers of control plants and PPaII-2, -3, and -5 and PPaI-2 and PPaI-55 with an antibody raised to inorganic pyrophosphatase. Lanes 1 and 2 are samples from two independent tubers.

Figure 5:
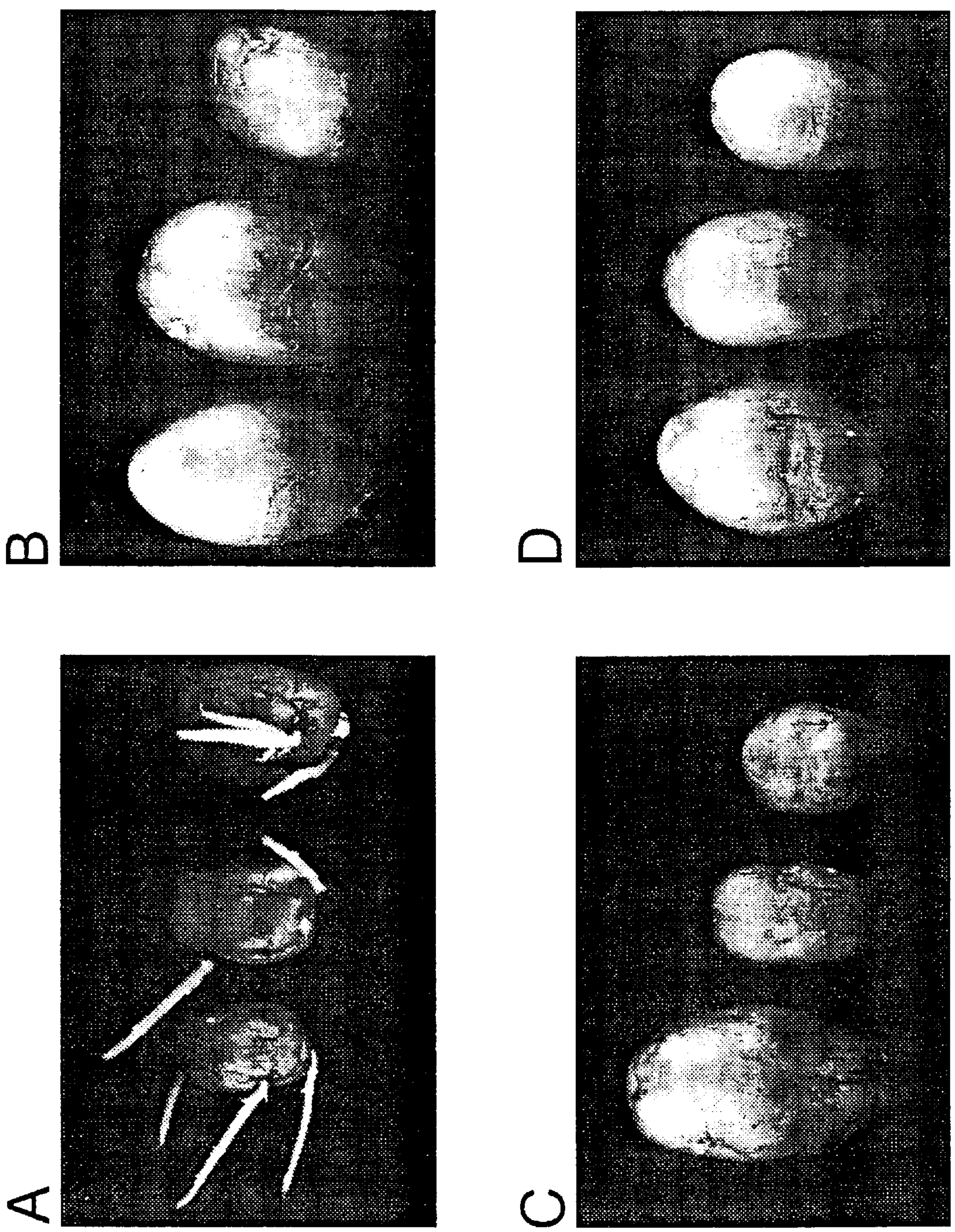

FIG. 5: shows photographs of tubers harvested from wild type and transgenic plants after storage for five months at room temperature and in the dark. A: wild type control (Desiree); B: transgenic plant PPaII-2; C: transgenic plant PPaII-3; D: transgenic plant PPaII-5.

Figure 6:
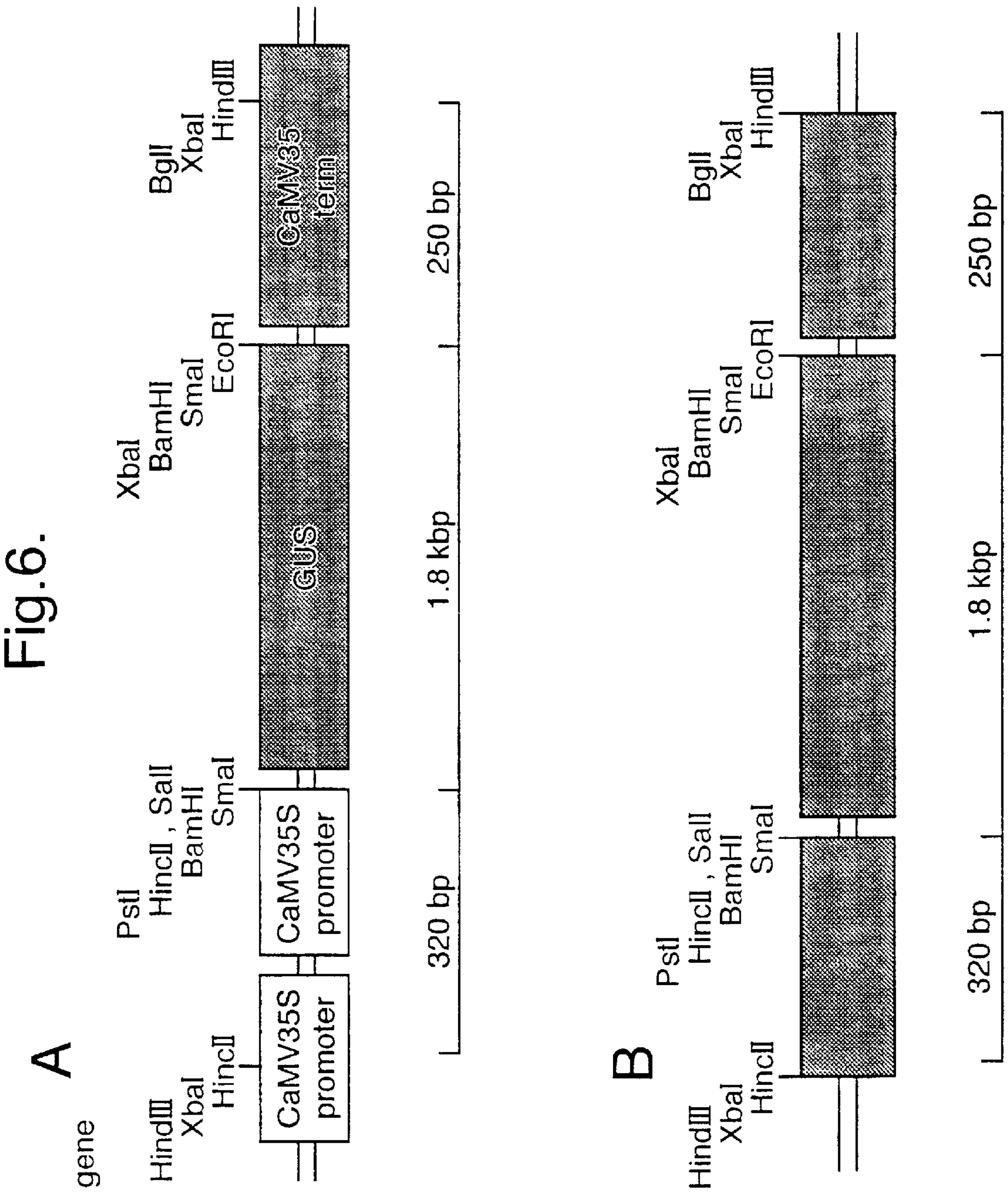
Figure 7:
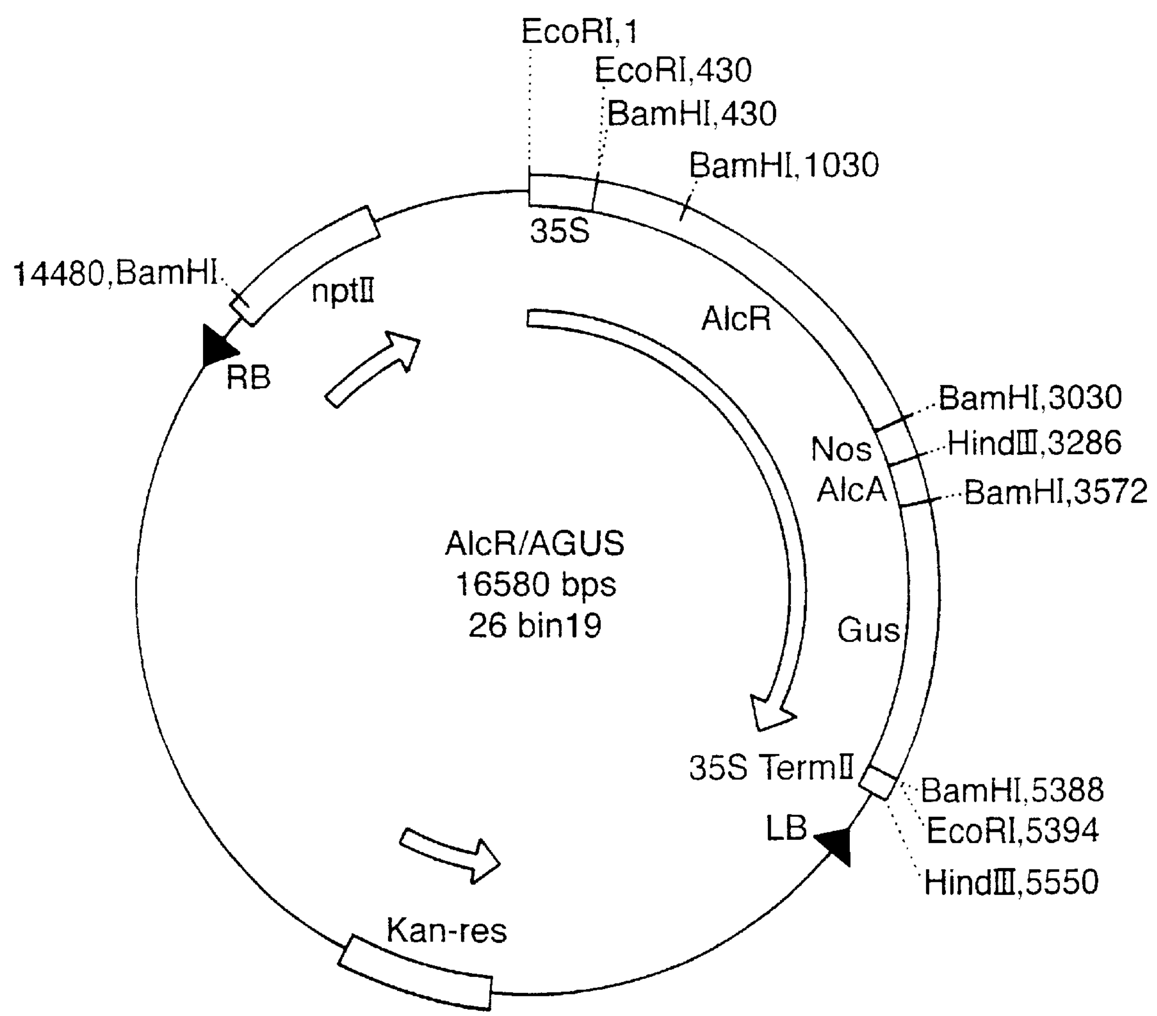

FIG. 6: shows: A: diagram of plasmid pJIT 166 B: diagram of pAGS/pUC GUS reporter gene construct FIG. 7: shows a map of plasmid AlcR/AGUS.

Figure 8:
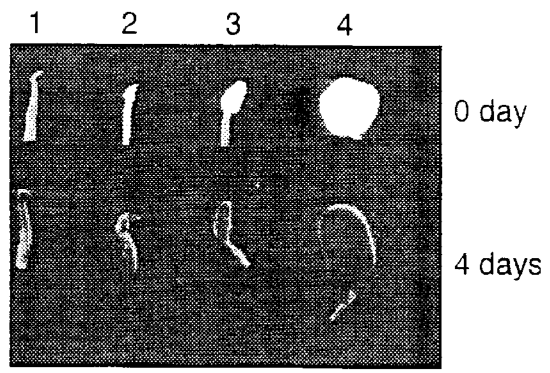

FIG. 8: Tissue culture grown potato plants were transferred into the greenhouse following cultivation for 8 weeks in 2.51 pots. Alc expression was induced via watering the plants three times (day 0, 1 & 2) with 50 ml of a 5% ethanol solution. On day 4 following the initial induction stolons and developing tubers were harvested and GUS activity was visualized using the histochemical staining procedure. 0 day, prior induction; 4 days, 4 days after initial induction shows histochemical detection of alc:GUS activity in stem, roots and stolons.

1: non-induced stolon, 2: swelling tuber, 3: developing tuber and 4: mature tuber.

Figure 9:
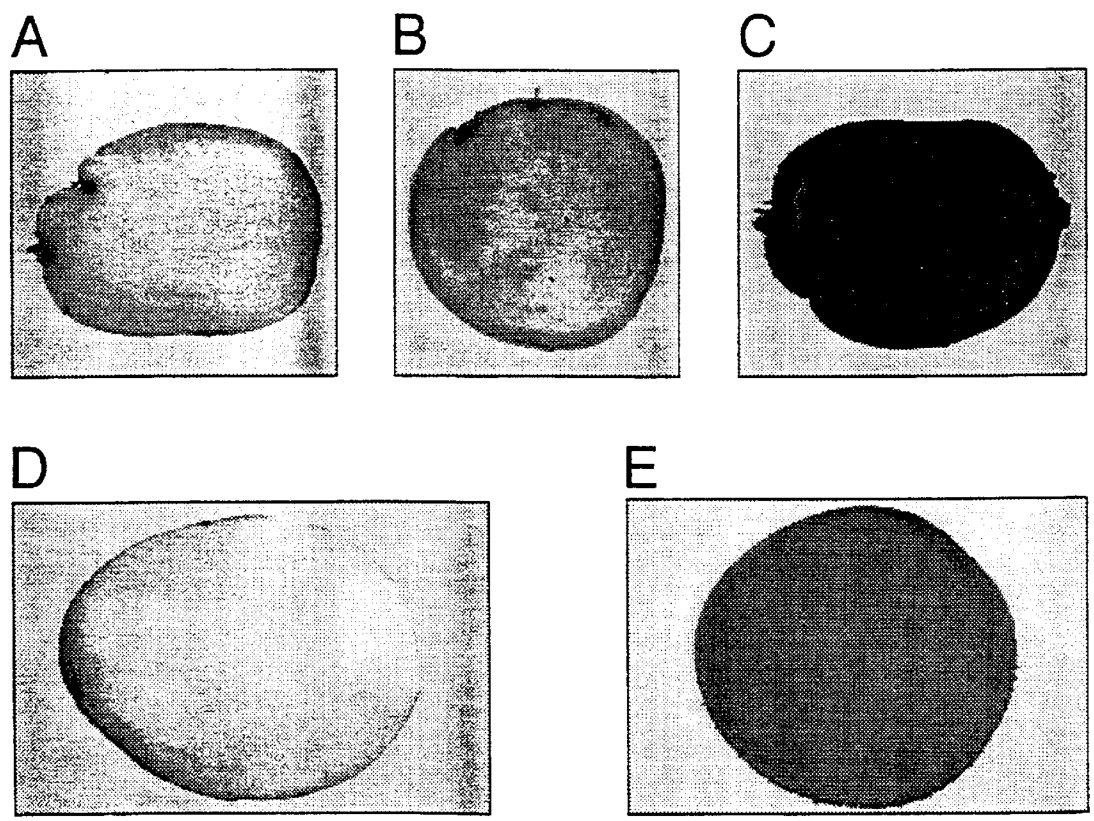

FIG. 9: shows a photograph of potato tubers after histochemical detection of alc:GUS activity following ethanol vapour treatment.

A: 0 days, B: 3 days, C: 7 days, D, untreated control, E, 7 days after treatment.

Figure 10:
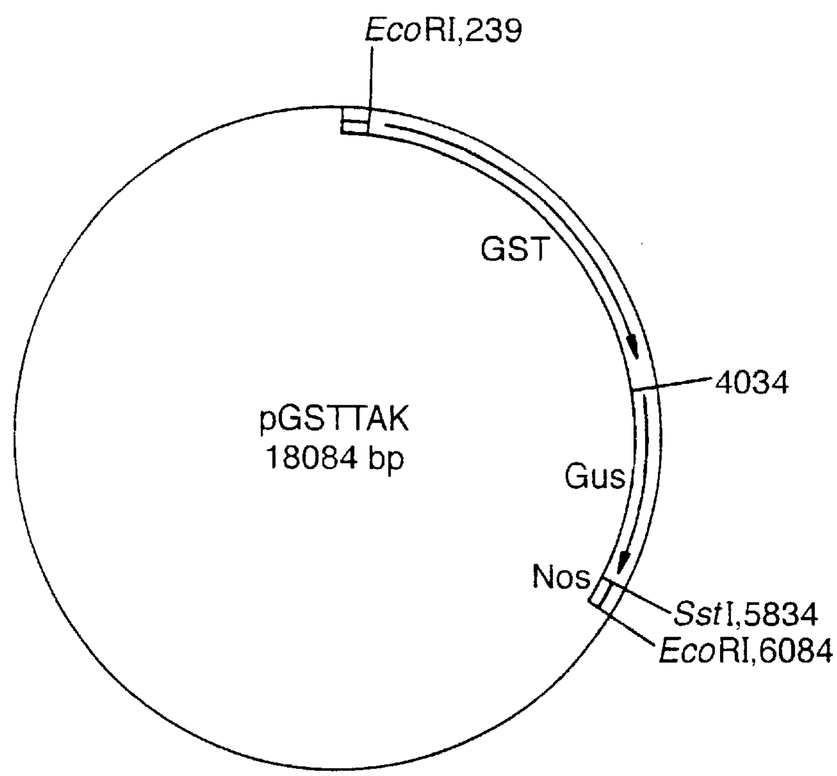

FIG. 10: shows a map of plasmid pGSTTAK.

Figure 11:
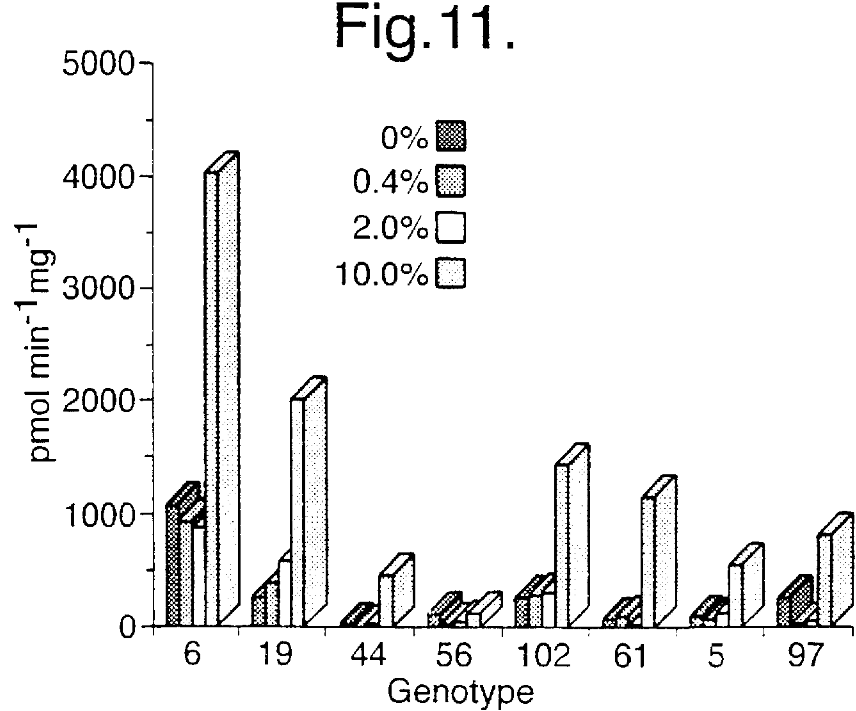

FIG. 11: shows a histogram analysis of GUS activity in fully developed leaves of GST-GUS transformed plants after cultivation for 14 days on MS-medium containing 0% ■ 0.4 ▨2.0% □ and 10% ▩R-25788.

Figure 12:
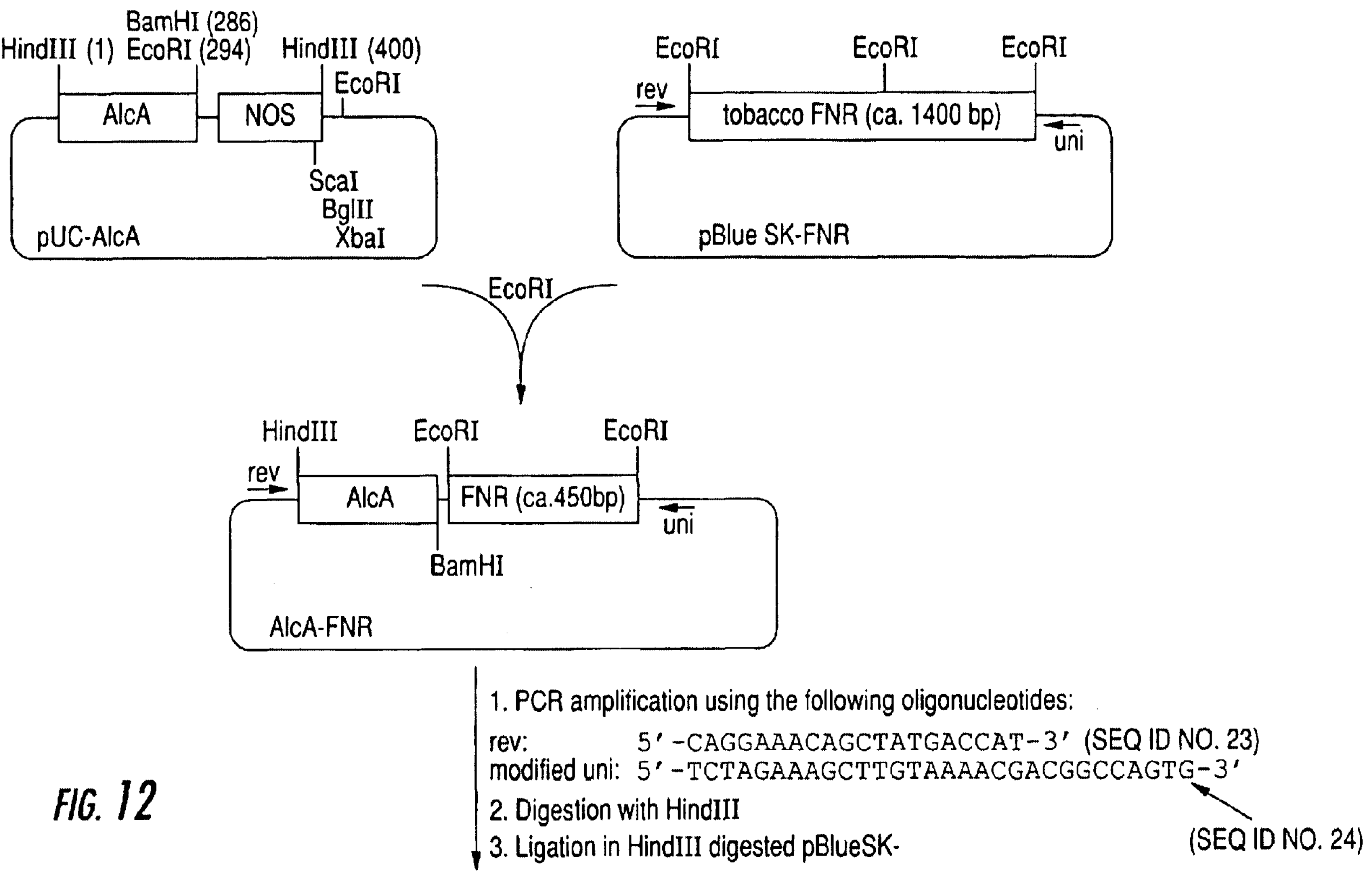
Figure 12:
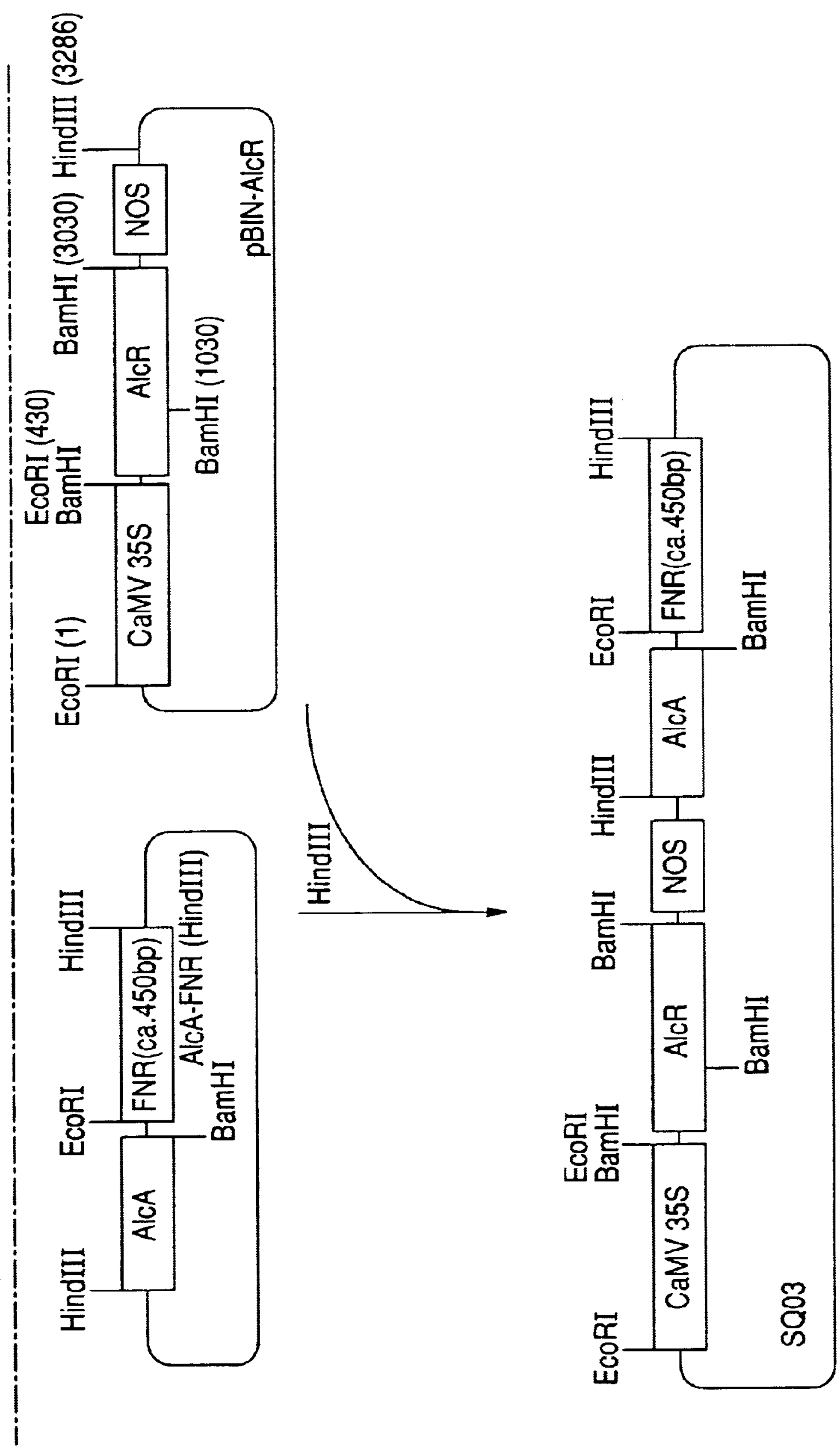

FIG. 12: (SEQ ID NOS.: 23 and 24) shows a diagram of the construction of plasmid SQ03.

Figure 13:
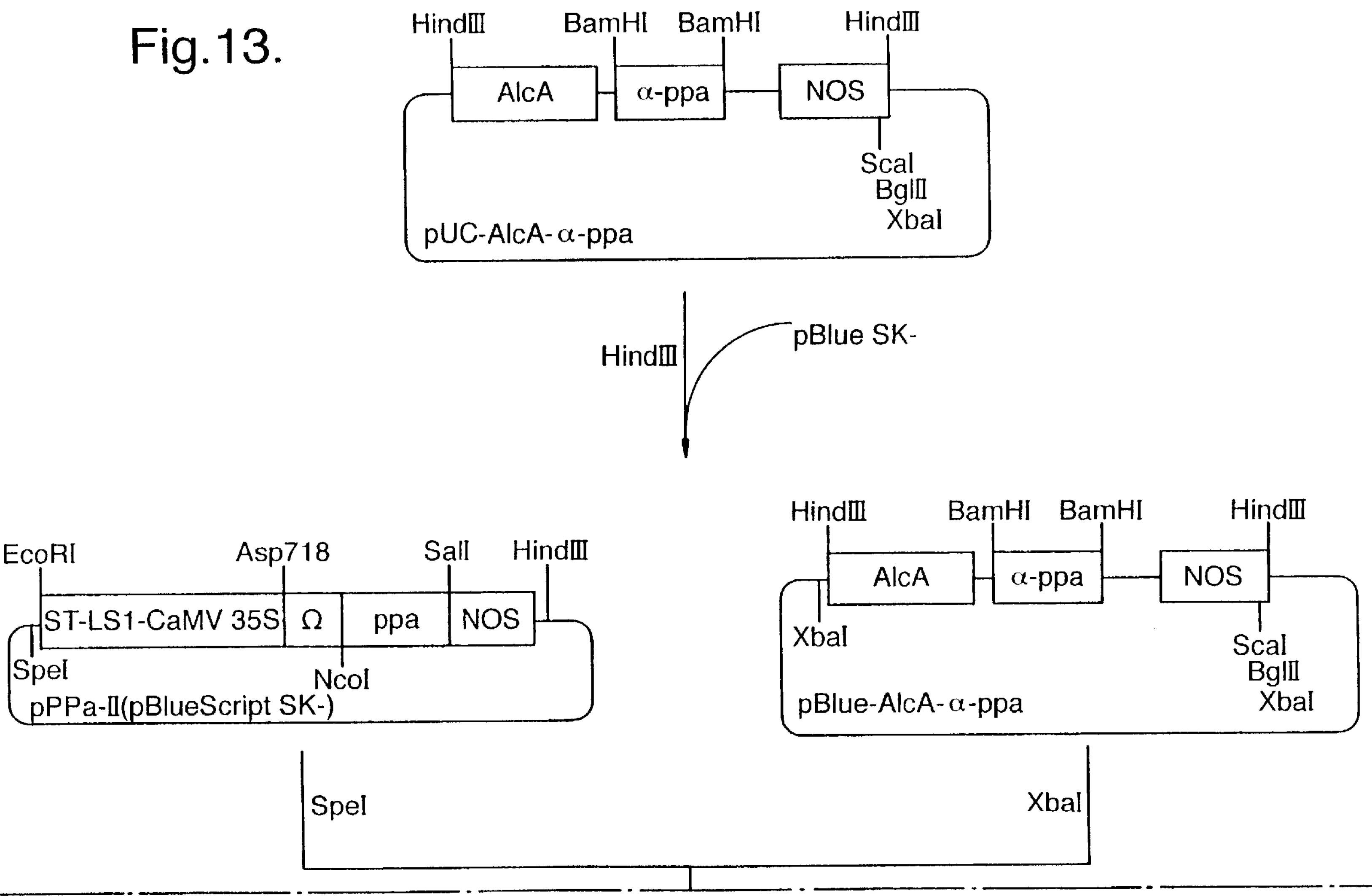
Figure 13:
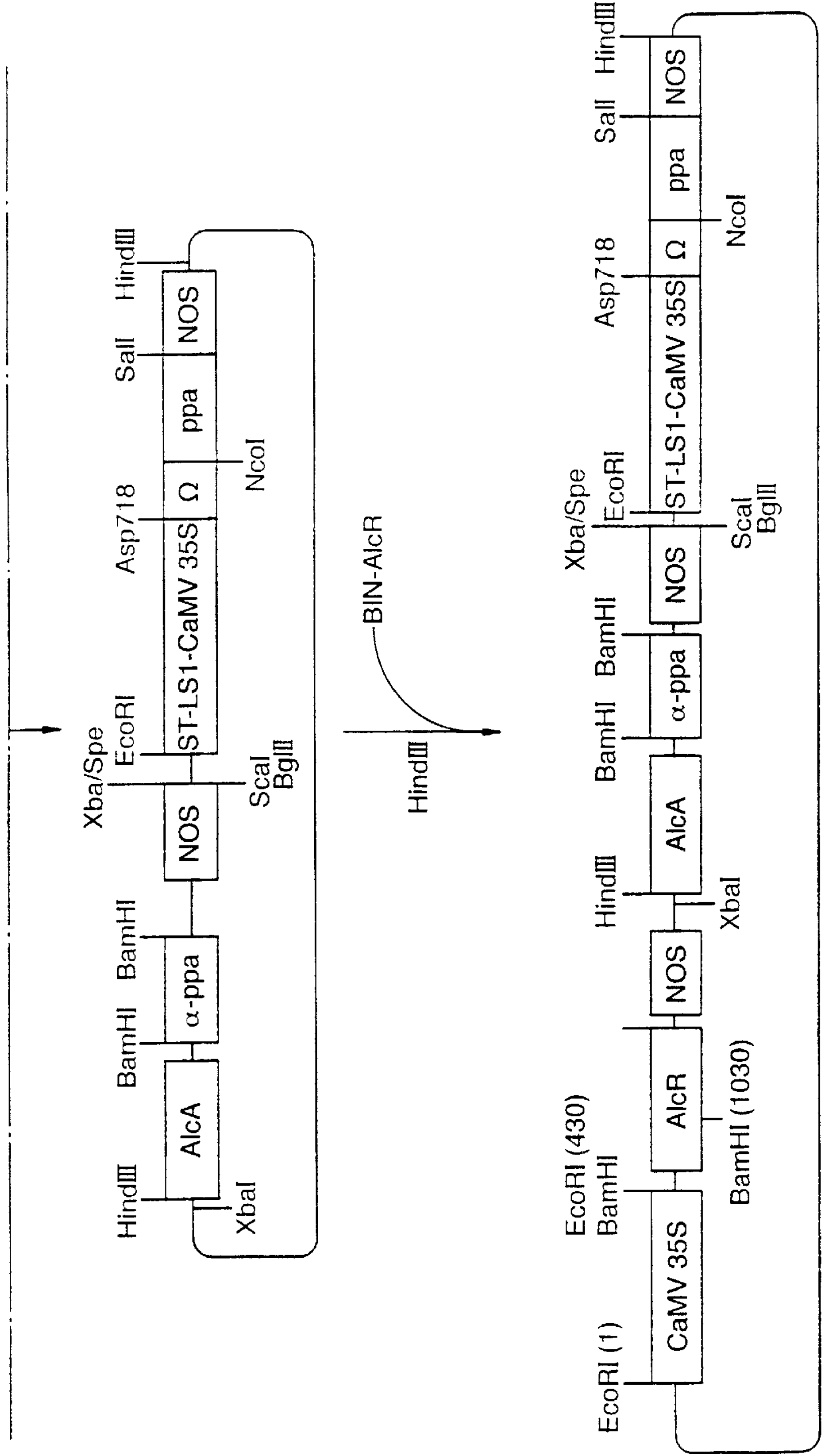

FIG. 13: shows a diagram of the construction of plasmid SQ-01.

Figure 14:
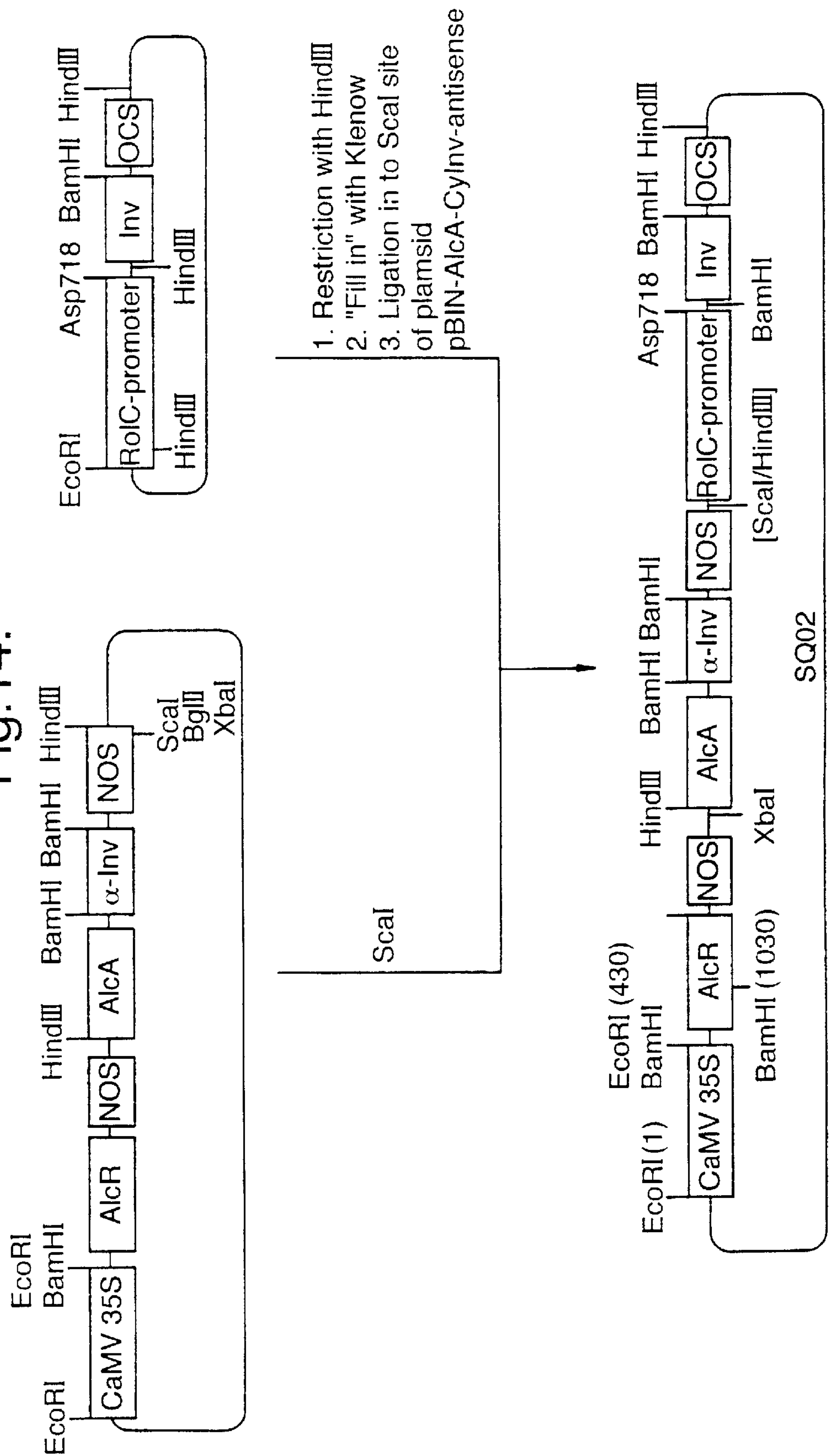

FIG. 14: shows a diagram of the construction of plasmid SQ-02.

Figure 15:
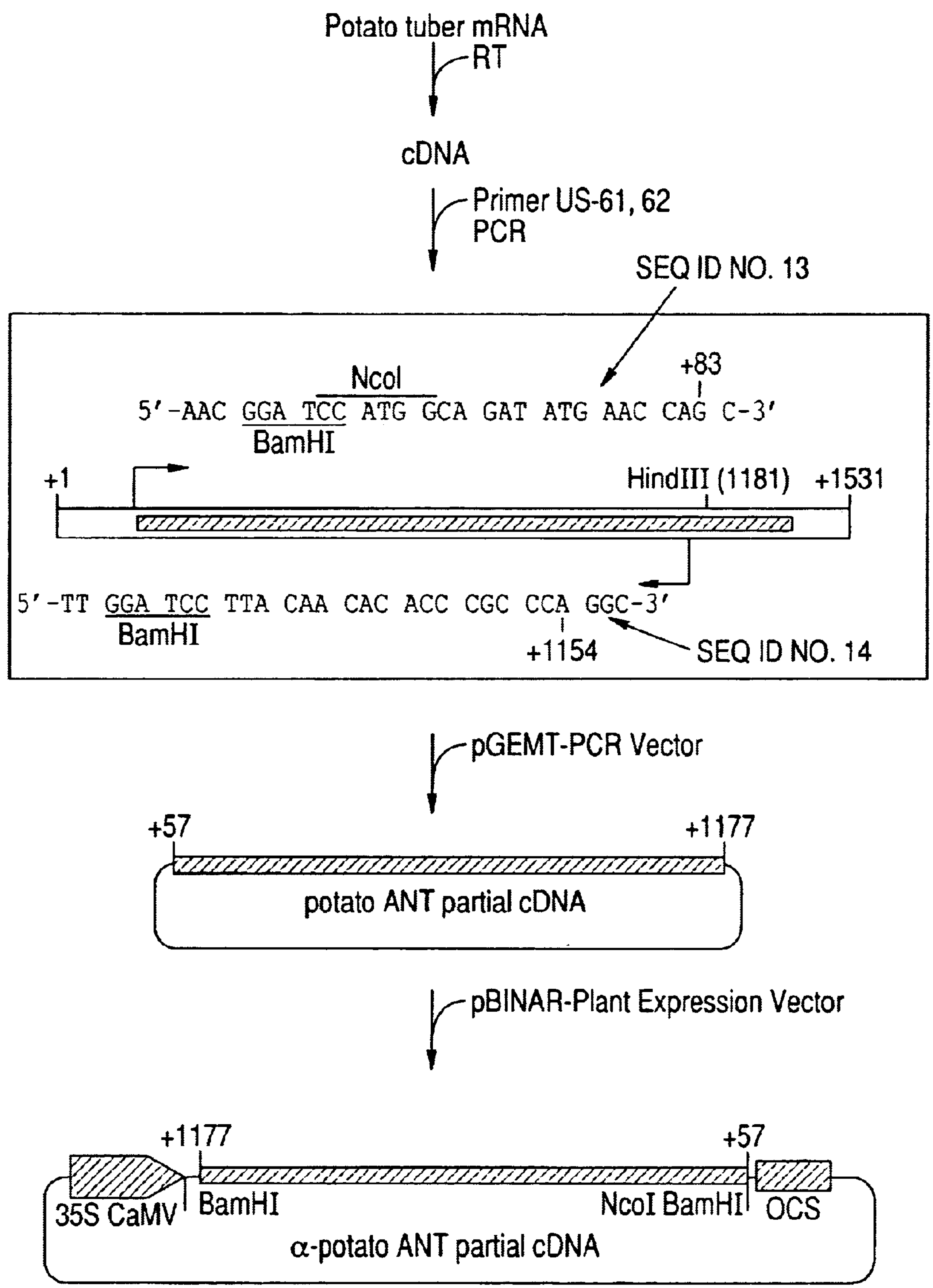

FIG. 15: (SEQ ID NOS.: 13 and 14) shows a diagram of the cloning of potato ANT.

Figure 16:
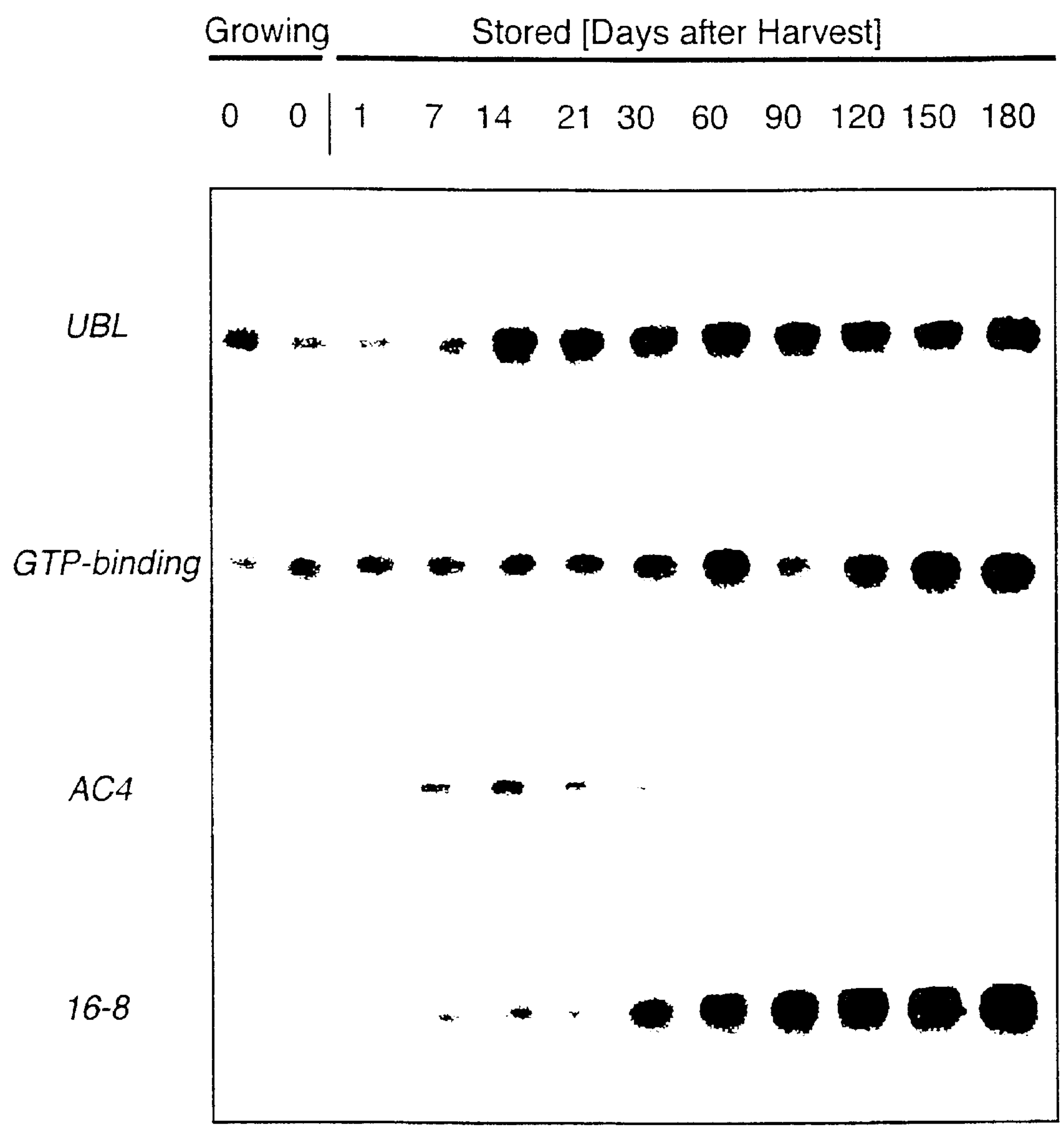

FIG. 16: shows accumulation of UBL-,GTP-binding-, AC4-, and 16-8-specific transcripts in different areas of sprouting tubers.

Figure 17:
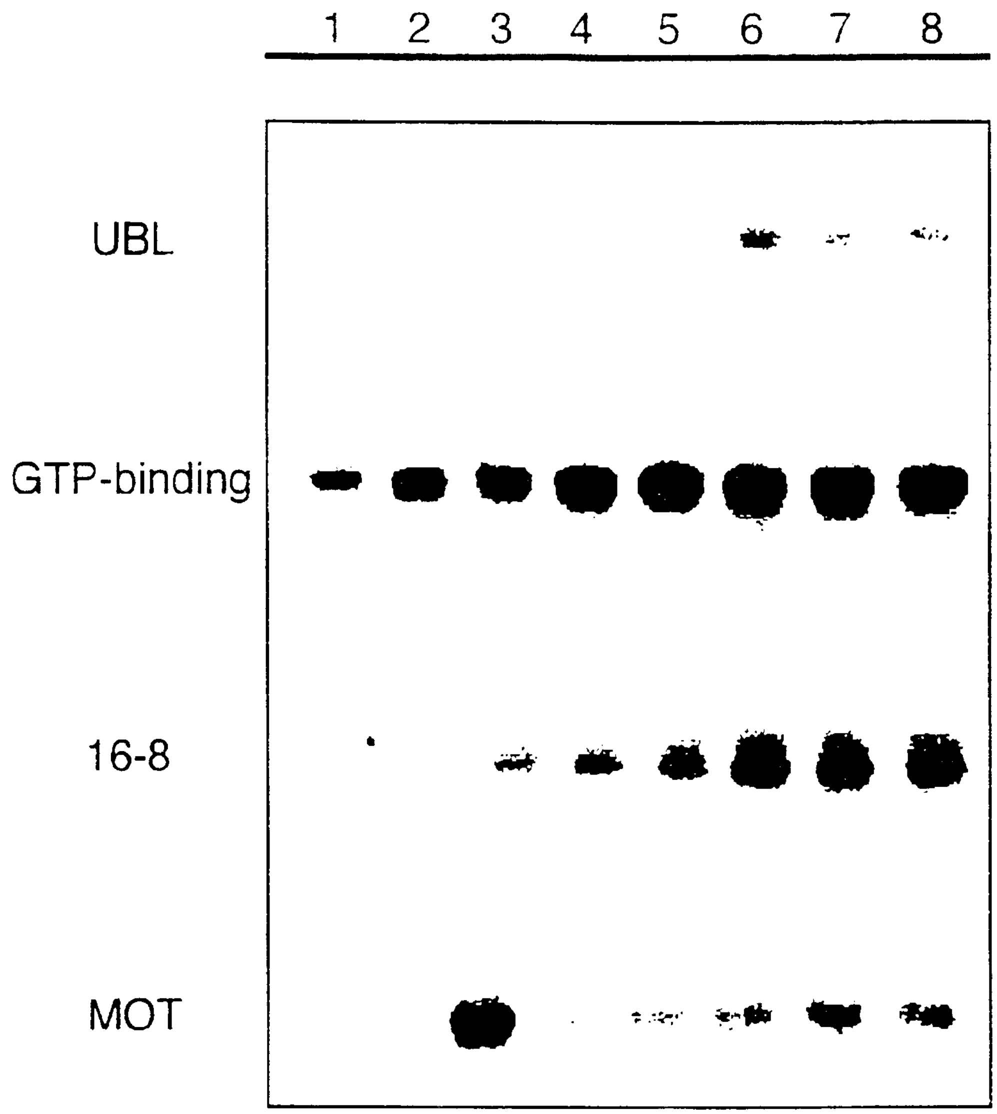

FIG. 17: shows accumulation of UBL-,GTP-binding-, 16-8-, and MOT-specific transcripts in different areas of sprouting tubers.

Figure 18:
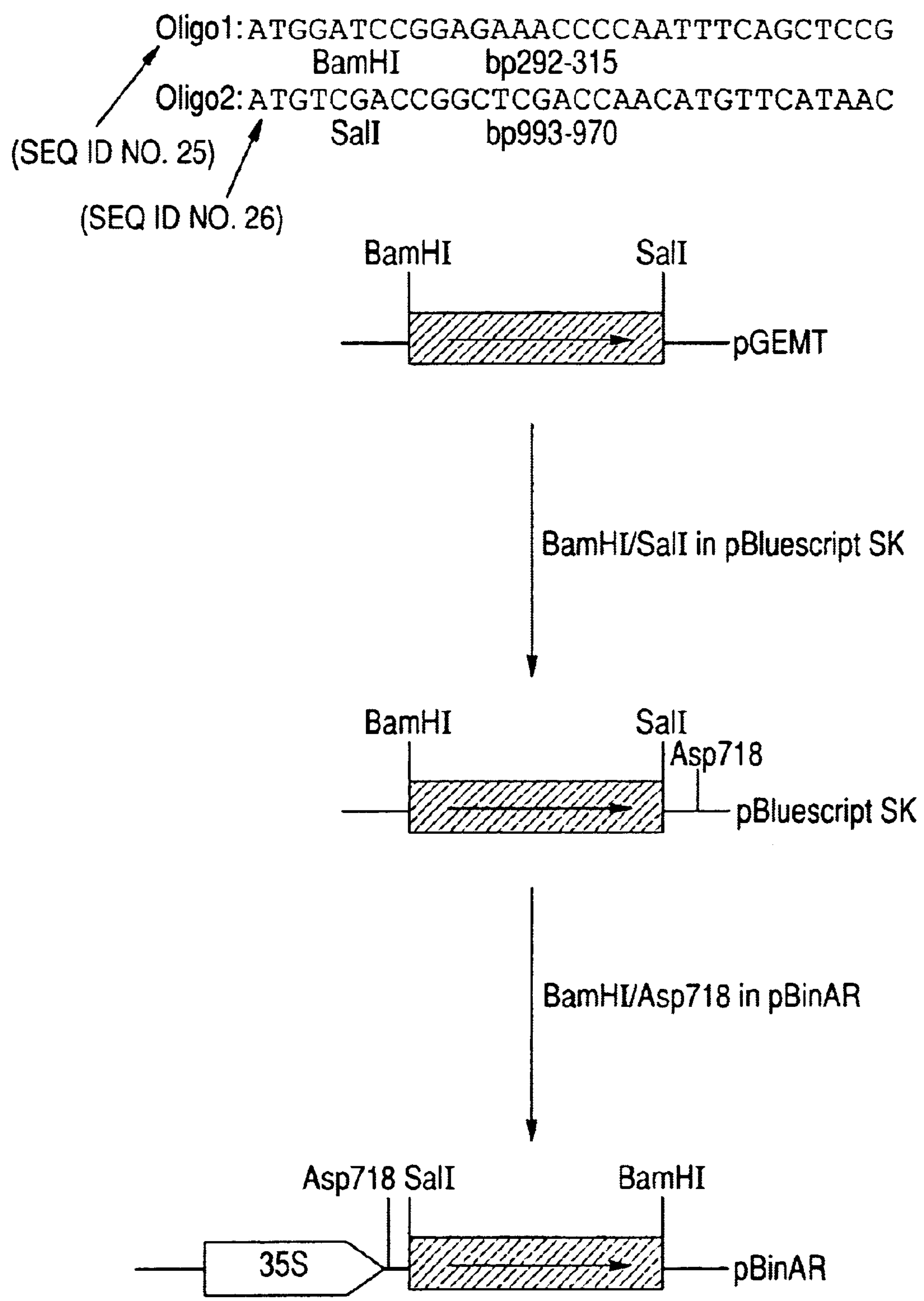

FIG. 18: (SEQ ID NOS.: 25 and 26) shows a diagram of the construction of an antisense MOT construct.

FIG. 19: (SEQ ID NOS.: 27 and 33) shows the DNA sequence encoding MOT isolated from potato.

FIG. 20: (SEQ ID NOS.: 34 and 35) shows sequence homology between the protein encoded by clone M-1-1 (MOT) and *Panicum miliaceum* mitochondrial oxoglutarate.

Figure 21:
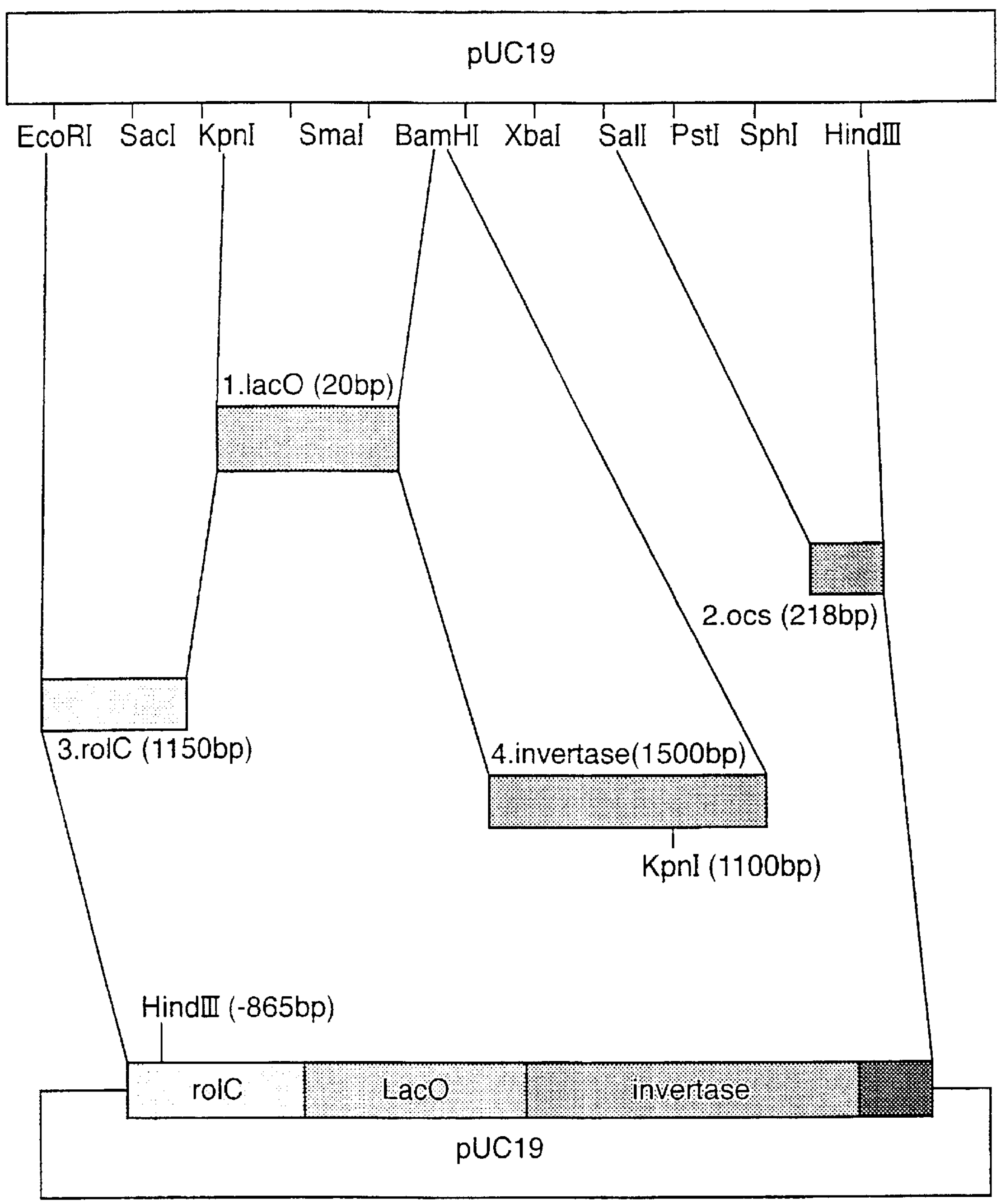

FIG. 21: shows the strategy for cloning the lac operator sequence into a RolC-invertase plasmid.

Figure 22:
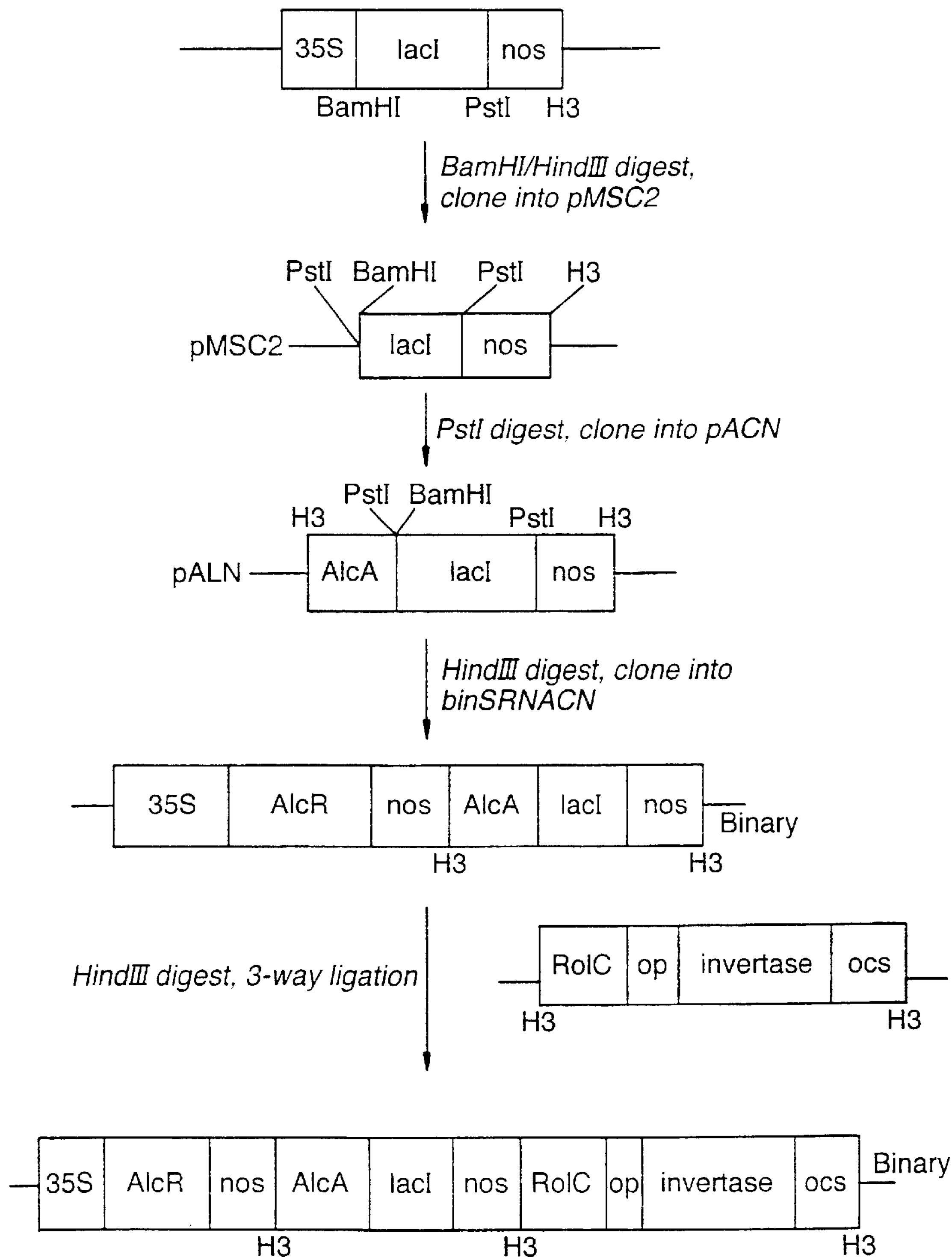

FIG. 22: shows the strategy for cloning Lac I into an Alc switch binary vector and ligation to RolCopINV.

Figure 23:
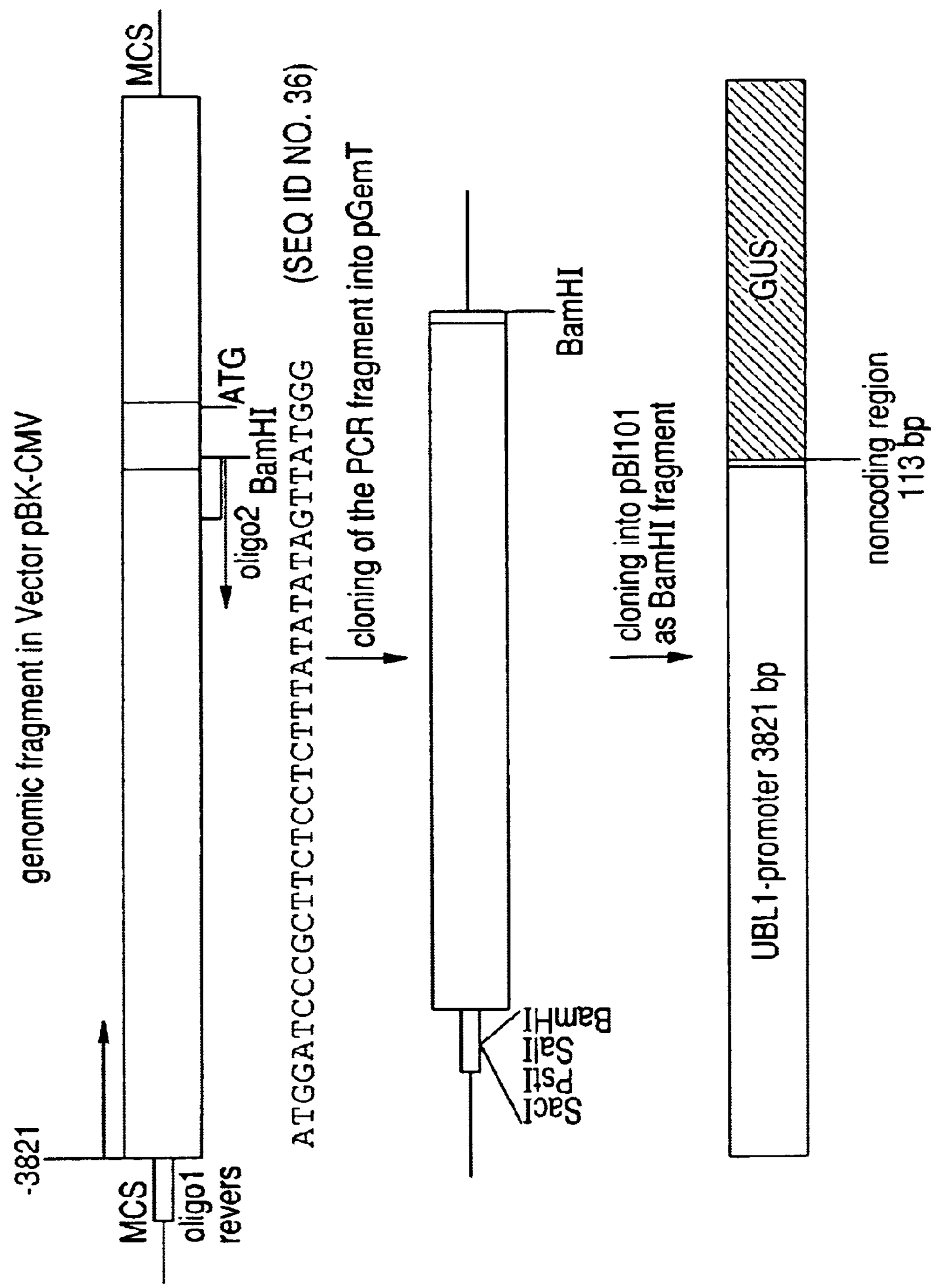

FIG. 23: (SEQ ID NO.: 36) shows the isolation of the UBL-1 promoter by PCR.

Figure 24:
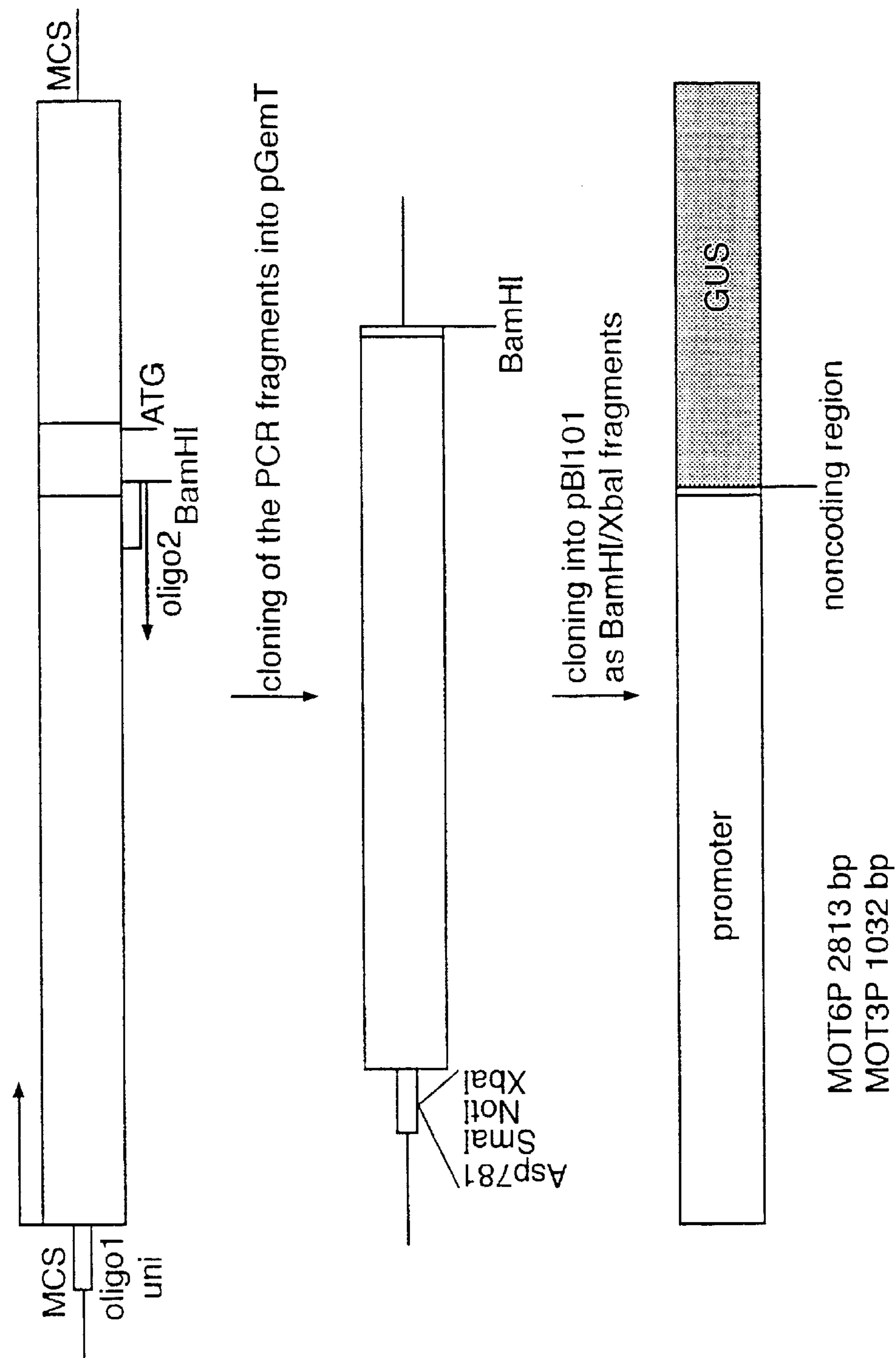

FIG. 24: shows the isolation of the MOT-promoters by PCR.

FIG. 25: (SEQ ID NO.: 37) shows the UBL-1 promoter nucleic acid sequence.

FIG. 26: (SEQ ID NO.: 38) shows the MOT3 promoter nucleic acid sequence.

FIG. 27: (SEQ ID NO.: 39) shows the MOT6 promoter nucleic acid sequence.

Figure 28:
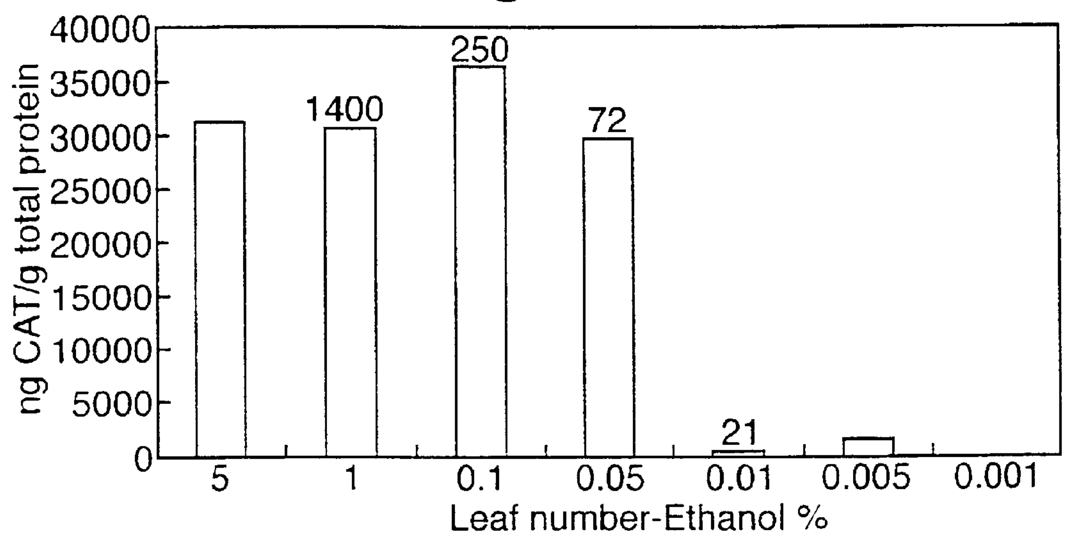

FIG. 28: shows a CAT assay of ALC-CAT tobacco leaves from plants enclosed with an ethanol source for 24 hours. The numbers above the columns represent ng ethanol/ml headspace.

Figure 29:
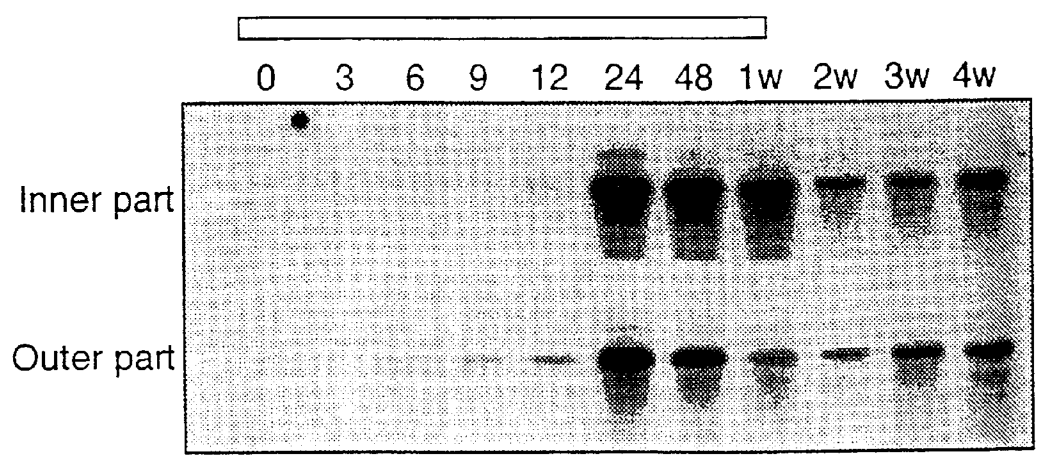

FIG. 29: shows the kinetics of CUS RNA transcript in 35S-Alc-GUS potato tubers after ethanol induction. The outer part refers to the part which is 1–3 mm beneath the skin of the potato tuber, the remaining part of the potato being referred to as the inner part. The induction was performed in 40 liters of plastic chamber tightly sealed with rubber for 1 week. The ethanol concentration was 0.02% gas phase (8 ml of 96% ethanol/401) and 20 μg of the total RNA was loaded onto each slot.

Figure 30:
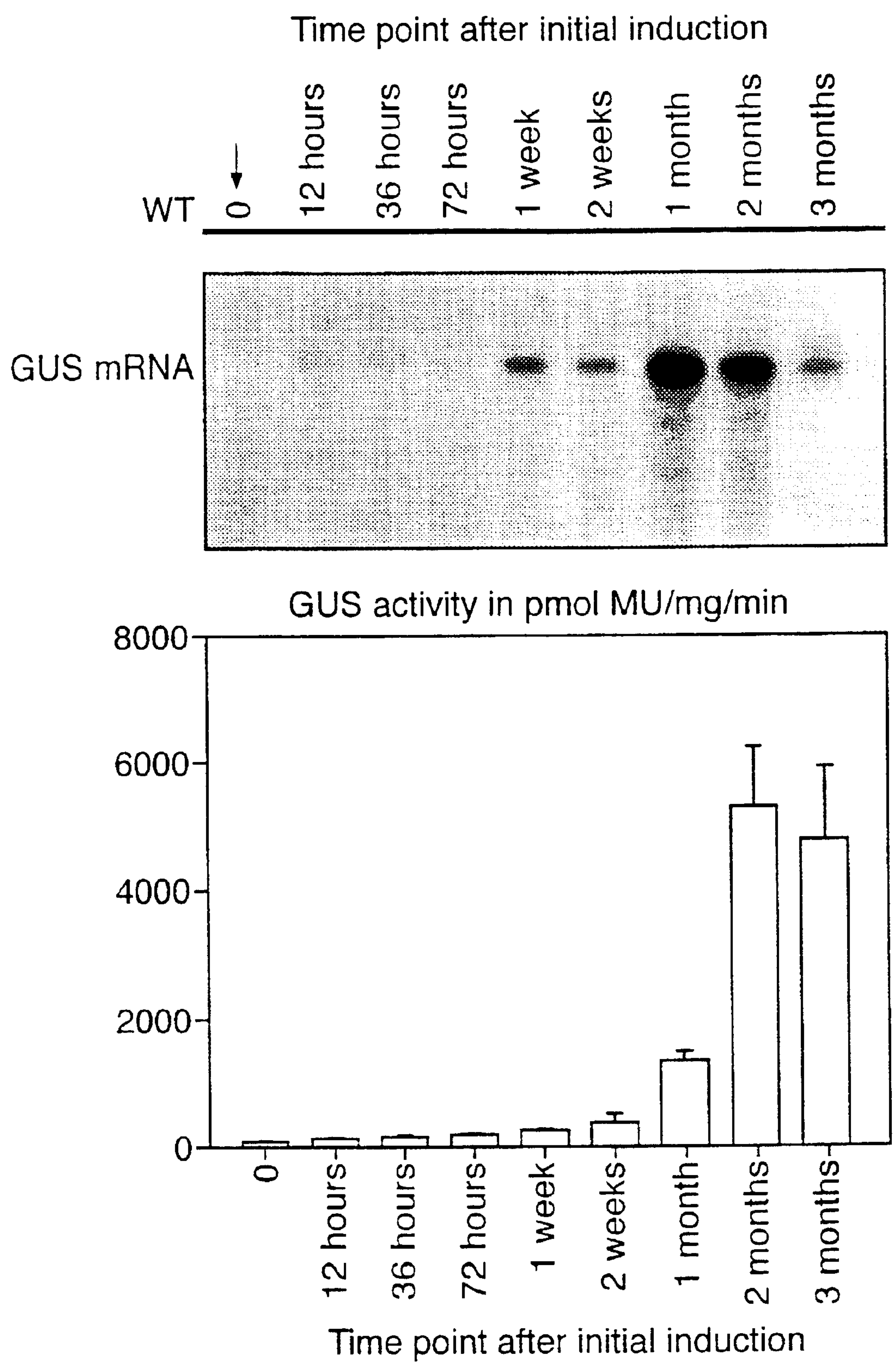

FIG. 30 shows the kinetics of GUS transcript and activity in 35S-Alc-GUS potato tubers induced by 1% ethanol.

EXAMPLES

I. Exemplification of Sprout Inhibition

1. Inhibition of Potato Tuber Sprouting via the Expression of Phloem-specific Invertase 1.1. Construction of Plasmid pBIN-RolC The rolC promoter from *Agrobacterium rhizogenes* was cloned by polymerase chain reaction (PCR) following the instructions of the manufacturer (Perkin Elmer, Ueberlingen, Germany). The temperature profile of the PCR cycle (40 cycles) was as follows: 1 min at 95° C., 1 min at 45° C. and 2 min at 72° C. Plasmid DNA containing the rolC promoter was isolated from *A. rhizogenes* bearing the plasmid pABC002 (Schmülling et al., Plant Cell 1, 665–670 (1989)) using standard procedures (Sambrook et al., A Cloning Manual Cold Spring Harbor Laboratory Press 1989). Synthetic oligonucleotides were synthesised based on the published sequence of the rolC promoter fragment (Slightom et al., J. Biol Chem 261 (1) 108–121, 1986). The sequences (SEQ ID NOS.: 7 and 8) of the primers were: 5'-rolC primer D(GGAATTCGATACGAAAAAGGCAAGTGCC AGGGCC) and 3'-rolC primer d(CCCATG GTACCCCAT-AACTCGAA GCATCC). The amplified DNA was cloned into the PCR vector pCR1000™ (Invitrogen, Norwalk, Conn.). To exclude mutations of the amplified DNA during the PCR cycles, the clone was sequenced using the dideoxy method. The 1150-bp promoter fragment was subsequently cloned into a plant expression cassette pBINAR (Höfgen and Willmitzer Plant Sci. 66, 221–230 1990) by replacement of the 35S Cauliflower mosaic virus promoter sequence (Franck et al., Cell 21 285–294 (1980)) through the rolC promoter using 5'-restriction site of EcoRI and the 3'-restriction site of Asp718 included in the PCR primers. The final construct is based on the binary vector pBin19 (Bevan, Nucl Acid Res 12, 8711–8721 (1984)). The resulting plasmid contained the rolC promoter and the octopine synthase polyadenylation signal (Gielen et al., EMBO J 3, 835–846 1984)).

1.2. Construction of Plasmid pBIN-IN8 (FIG. 1)

To obtain a truncated version of the yeast Suc 2 gene PCR using the oligonucleotides (SEQ ID NOS.: 9 and 10) 5'-Suc2 d(GAGCTGCAGATGGCAAAGCAAACTAGCGATAGA CCTTTGGTCACA) and 3'-Suc2 d(GAGACTAGTTTATAACCTCTATTTACTTCCCTTA CTTGGAA) was applied to amplify the invertase gene from plasmid PI-3-INV (von Schaewen et al. EMBO J 9 3033–3044, (1990)). The PCR product was digested with PstI/SpeI and cloned into the PstI/XbaI sites of plasmid YIP128A1 yielding plasmid 181A1-INV (Riesmeier et al., EMBO J. 11 4705–13 (1992)). To obtain BamHI sites at both ends of the invertase gene plasmid 181A1-INV was digested with PstI/BamHI and the invertase fragment was ligated into vector pBlueSK-yielding plasmid pBlue-Suc2A. Subsequently plasmid pBlue-Suc2A was digested with SpeI/EcoRV, blunt ended with DNA polymerase and cloned into the SmaI site of pBlueSK-yielding plasmid pBlue-Suc2B. Using plasmid pBlue-Suc2B the invertase gene was isolated as a BamHI fragment and cloned into the BamHI site of plasmid pBIN-RolC. The resulting plasmid (pBIN-IN8) contained the Suc2 gene (Nucleotide 849 to 2393) between the rolC promoter and the octopine synthase polyadenylation signal (Gielen et al., EMBO J. 3, 835–46, 1984).

1.3. Transformation of Construct pBIN-IN8

*Agrobacterium tumefaciens* strain C58C1 containing pGV2260 (Deblaere et al., Nuc. Acid Res. 13, 4777–4788 (1989)) was transformed by direct transformation of variety Desiree by plasmid pBIN-IN8 as described by Höfgen and Willmitzer (Nucl Acid Res. 16, 9877 (1988)). Potato transformation was achieved following the protocol of Rocha-Sosa et al. (EMBO J. 8, 23–29 (1989)). Primary screening for increased invertase activity was done in midribs of tissue-culture-grown regenerated plants. Three lines (DIN-87, 90 and 30) out of 75 independent transformants were selected for further analysis. For a detailed analysis, ten replicates of each preselected transformant were transferred into the green house for tuber production.

1.4. Invertase Activity

Invertase assay. Plant tissue, quickly frozen in liquid nitrogen, was homogenised in extraction buffer (50 mM 4-(2-hydroxyethyl)-1-piperazineethane sulfonic acid (Hepes)-KOH, pH 7.4; 5 mM $MgCl_2$; 1 mM EDTA; 1 mM ethylene glycol-bis (b-aminoethylether)-N,N,N',N'-tetraacetic acid (EGTA); 1 mM phenyl-methylsulfonyl-fluoride (PMSF); 5 mM dithiothreitol (DTT); 0.1% Triton X-100, 10% glycerol) and centrifuged (5 min, 4° C., 9000 g, Biofuge 13; Heraeus, Hanau, Germany). For assaying neutral invertase the reaction mixture contained 20 mM Hepes-KOH pH 7.5, 100 mM sucrose and 10–30 $\mu$l of the protein extract in a final volume of 100 $\mu$l. Incubation was carried out at 30° C. for 30–60 minutes and stopped at 95° C. for 3 minutes. Blanks had the same reaction mixture but were heat inactivated without incubation. The determination of glucose and fructose was as described in Stitt et al. (Methods Enzymol. 174, 518–522 (1989)). For assaying soluble acid invertase the reaction mixture contained 20 mM sodium acetate pH 4.7, 100 mM sucrose and 10–30 $\mu$l of the protein extract in a final volume of 100 $\mu$l. Incubation was carried out at 30° C. for 30–90 minutes. To neutralise the reaction mixture before stopping the reaction at 95° C. for 3 minutes 10 $\mu$l of 1 M sodium phosphate pH 7.2 was added. Blanks had the same reaction mixture but were heat inactivated without incubation.

Following harvest tubers of transformed and untransformed potato plants were stored for 5 months at 20° C. Subsequently neutral and acidic invertase activity was determined in tuber slices. The result is shown in Table 1.

TABLE 1

Invertase activity in potato tubers stored for 5 month at 20° C.

| genotype | neutral invertase | soluble acidic invertase |
|---|---|---|
| Control | 32.7 ± 4.2 | 18.0 ± 1.3 |
| DIN-87 | 115.3 ± 6.1 | 141.2 ± 8.8 |
| DIN-90 | 93.9 ± 4.7 | 126.0 ± 6.2 |
| DIN-30 | 121.5 ± 8.4 | 174.8 ± 16.5 |

Mean values are given ± standard deviation (n=4). Invertase activity is presented in nmol $gFW^{-1}$ $min^{-1}$. Control is wild type Desiree.

1.5. Impact of Invertase on Sugar Accumulation in Potato Tubers

Determination of soluble sugars. Tubers were harvested and tuber slices (60–70 mg fresh weight, 0.1 $cm^3$ average volume) were immediately frozen in liquid nitrogen. The slices were extracted with 1 ml 80% ethanol (10 mM Hepes-KOH, pH 7.4) at 80° C. for 1–2 h. The supernatant was used for the determination of glucose, fructose and sucrose as described in Stitt et al. (1989). The pellet was extracted a second time, washed in water, and dried. Determination of starch content was done using a starch determination kit (Boehringer Mannheim). The results are shown in Table 2.

TABLE 2

Carbohydrate composition of potato tubers expressing cytosolic yeast invertase under control of the RolC promoter.

| Genotype | Fructose | Glucose | Sucrose | Starch |
|---|---|---|---|---|
| Control | 0.9 ± 0.1 | 6.2 ± 0.2 | 8.7 ± 0.4 | 652 ± 15 |
| DIN-30 | 0.3 ± 0.1 | 8.7 ± 1.0 | 2.1 ± 0.2 | 604 ± 19 |
| DIN-87 | 0.8 ± 0.1 | 6.5 ± 0.4 | 3.1 ± 0.2 | 753 ± 26 |
| DIN-90 | 0.8 ± 0.01 | 3.1 ± 0.6 | 3.5 ± 0.1 | 903 ± 39 |

Mean values are given±standard error (n=12, control; n=4, transgenic). Sugar content is presented as $\mu$mol hexoses $gFW^{-1}$. Control is wild type Desiree 1.6. Yield Potato plants were grown in a greenhouse at 60% relative humidity in a 16 h light (22° C.) and 8 h dark (15° C.) cycle (irradiance 300 $\mu$mol $m^{-2}$ $s^{-1}$). To estimate the impact of phloem-specific cytosolic yeast-derived invertase on tuber fresh weight and tuber number ten plants each genotype were cultivated in 21 pots. As shown in Table 3, total fresh weight and tuber number of the transgenic plants is indistinguishable from wildtype.

TABLE 3

Tuber yield of invertase expressing potato plants

| Genotype | Tuber fresh weight | Tuber number |
|---|---|---|
| Control | 118.3 ± 1.1 | 15 ± 0.01 |
| DIN-87 | 116.5 ± 6.1 | 11 ± 1.9 |
| DIN-90 | 121.1 ± 0.2 | 12 ± 1.9 |
| DIN-30 | 106 ± 10.5 | 13.5 ± 2.8 |

Mean values are given±standard deviation (n=10). Tuber fresh weight is presented in g. Control is wild type Desiree 1.7. Sprout Inhibition of Transgenic Plants To investigate the impact of phloem-specific cytosolic invertase on tuber sprouting harvested tubers of transformed and wildtype plants were stored for a prolonged time in the dark at room temperature. Wildtype Desiree tubers started to sprout after 5 to 6 months whereas tubers of transgenic plants did not show any visible sign of sprouting. Even after one year of storage tubers of transgenic plants did not develop any vital sprout (FIG. 3). Thus, expression of phloem-specific invertase leads to a complete inhibition of potato tuber sprouting.

2. Inhibition of Tuber Sprouting Via Expression of *E. coli* Inorganic Pyrophosphatase 2.1. Construction of Plasmid PPA-2 and Potato Transformation (FIG. 2)

The 1600 bp promoter fragment of the STLS-1 gene (Eckes et al., Mol. Gen. Genet. 205, 14–22 (1986)) was isolated as a EcoRI-BamHI fragment from plasmid 1600-

CAT (Stockhaus et al., 1987). After removal of the overlapping nucleotides the fragment was cloned into the blunted EcoRI site of the chimeric ppa gene described in Sonnewald (Plant J. 2, 571–581 (1992)). The final construct containing the STLS-1 promoter/enhancer, the 35S CaMV promoter, the TMV-U1 translational enhancer, the *E. coli* ppa coding region and the octopine synthase polyadenylation signal was cloned as a EcoRI-HindIII fragment into the binary vector Bin19 (Bevan, 1984 J. loc cit). Direct transformation of *Agrobacterium tumefaciens* strain C58C.1:pGV2260 was done as described by Höfgen and Willmitzer (Nucl Acid Res. 16 9877 (1988)). Potato transformation using Agrobacterium-mediated gene transfer was performed as described by Rocha-Sosa et al. (EMBO J. 8 23–29 (1989)).

Following Agrobacterium mediated gene transfer forty independent transformed plants were analysed for the presence of the PPase protein using inmmunoblotting. Three plants (PPaII-2, 3 and 5) with the highest amount of PPase protein were selected for further analysis. To compare the promoter strength of the chimeric 35S CaMV promoter (PPaII) and the unmodified 35S CaMV promoter (PPaI) protein extracts from potato tubers were analysed by western blotting. As shown in FIG. 4, the amount of the PPase protein, detectable in protein extracts from growing PPaII tubers, is significantly higher as compared to the PPaI control. The same results were obtained in tubers stored for three and twelve months at room temperature. This analysis compared the highest expressing lines from the PPaI and PPaII populations where 70 independent transformants were selected for PPaI and 40 for PPaII. It is clear from this analysis that the STL1 promoter fragment enhances tuber expression of inorganic pyrophosphatase. The expression of the *E. coli* inorganic pyrophosphatase was paralleled by an increase in pyrophosphatase activity measured in protein extracts from PPaII tubers (Table 4). Depending on the amount of pyrophosphatase activity the pyrophosphate content decreased up to two-fold (Table 4).

TABLE 4

Elevated cytosolic inorganic pyrophosphatase leads to reduced PPi accumulation in tubers of PPaII transformants.

| Genotype | Pyrophosphatase activity [$\mu$mol g FW$^{-1}$ minute$^{-1}$] | Pyrophosphate [nmol g FW$^{-1}$] |
|---|---|---|
| Control | 3600 ± 410 | 2.4 ± 0.2 |
| PPaII-2 | 5600 ± 150 | 1.4 ± 0.2 |
| PPaII-3 | 6200 ± 220 | 1.2 ± 0.3 |
| PPaII-5 | 8500 ± 220 | 1.1 ± 0.1 |

Tubers were harvested from plants grown for 150 days in the greenhouse. The results are mean values±SD (n=3 for wildtype and n=4 for transgenic plants) of three tubers from three different wildtype plants and two to four tubers each PPaII plant.

2.2. Immunoblot Analysis

Following separation on 12.5% SDS polyacrylamide gels (Laemmli, 1970), proteins were transferred onto nitrocellulose membranes (Millipore, Bradford, Mass., USA) using a semi-dry electroblotting apparatus (Multiphore II; LKB, Bromma, Sweden). Incubation with anti-PPase polyclonal antibodies (Lerchl et al., Plant Cell 7 259–270 (1995)) in a 1:1000 dilution was for 90 minutes at room temperature. Immunodetection of the antigen was done using the biotin-streptavidin system from Amersham Buchler with rabbit biotinylated species-specific whole antibodies (from donkey) and streptavidin-biotinylated horse-radish peroxidase.

2.3. Pyrophosphatase Activity Assay

To measure pyrophosphatase (PPase) activity 100–200 mg potato tuber slices were homogenised in 0.5 ml 100 mM 4-(2-hydroxyethyl)-1-piperazineethanesulfonic acid (HEPES)-KOH (pH 7.5), 2 mM Mg2Cl, 1 mM EDTA, 1 mM EGTA, 5 mM mercaptoethanol. After centrifugation (10 minutes, 13.000 rpm at 4° C.) 20 $\mu$l of the supernatant was assayed in 160 $\mu$l 50 mM Tris-HCL (pH 8.0), 16 mM MgSO4 and 100 mM KCl for PPase activity. Following addition of 20 $\mu$l 50 mM NaPPi the reaction was carried out for 20 minutes at 30° C. The reaction was stopped by addition of 20 $\mu$l 1 M citrate and the release of inorganic phosphate was assayed as in Heinonen and Lathi (Anal Biochem 113, 313–317 (1981)). The assay was linear with time and amount of extract.

2.4. Determination of Inorganic Pyrophosphate in Tuber Tissue

To measure pyrophosphate 200–300 mg of tuber tissue was frozen in liquid nitrogen. Frozen material was subsequently homogenised to a fine powder in liquid nitrogen in a mortar standing on powdered dry ice (solid $CO_2$). A 15 ml aliquot of 16% trichloroacetic acid (TCA) in diethylether (v/v), precooled to the temperature of dry ice, was added and the sample further homogenised. After leaving the homogenate for 20 minutes on dry ice, 0.8 ml of 16% TCA in water (v/v) containing 5 mM NaF was added. The mixture was warmed to 4° C. and left for 3 hours. Subsequently the homogenate was extracted four times with diethylether and neutralised with KOH/triethanolamine as in Weiner et al. (Biochem Biophys Acta 893, 13–21 (1987)). All mortars and materials were prewashed for 12 hours in 2 N HCl, and pseudoextracts were prepared in parallel to check that the reagents and apparatus were not contaminated with pyrophosphate. efore assaying for pyrophosphate content 400 $\mu$l of extract was added to 400 $\mu$l of cation exchanger (Serva, Heidelberg, FRG; Dowex AG 50×8, 100–200 Mesh, pre-equilibrated with 2 N HCl, brought to pH 5 with water, and then dried for 12 hours at room temperature), mixed for 20 seconds, and centrifuged to remove compounds in the extract which interfere with the metabolite assay. Pyrophosphate was assayed photometrically as in Weiner et al. (1987). The reliability of the extraction and assay was checked by adding a small representative amount (two- to threefold the endogenous content) of pyrophosphate to the plant material in the killed mixture of TCA and diethylether.

2.5. Yield

Potato plants were grown in a greenhouse at 60% relative humidity in a 16 h light (22° C.) and 8 h dark (15° C.) cycle (irradiance 300 $\mu$mol m$^{-2}$ s$^{-1}$). To estimate the impact of the *E. coli* inorganic pyrophosphatase on tuber fresh weight and tuber number five plants each genotype were cultivated in 2 l pots. Total tuber fresh weight of PPaII plants was unaltered as compared to wildtype controls (Table 5).

Table 5: Influence of *E. coli* inorganic pyrophosphatase on potato tuber development. The tubers were harvested from plants which had been growing in the green house for 150 days. The results are means of five individual plants each genotype.

TABLE 5

Influence of *E. coli* inorganic pyrophosphatase on potato tuber development. The tubers were harvested from plants which had been growing in the green house for 150 days. The results are means of five individual plants each genotype.

| Genotype | Tuber fresh weight [g] | Tuber number |
|---|---|---|
| Control | 89–148 | 12 ± 0.6 |
| PPaII-3 | 99–139 | 19 ± 1.7 |
| PPaII-5 | 110–167 | 21 ± 4.0 |
| PPaII-2 | 89–192 | 19 ± 0.5 |

of expression in the PPaI transgenic plants was not sufficient to prevent sprouting. 2.6. Sprout inhibition of transgenic plants.

Tubers harvested from wildtype plants started to sprout after five to six months of storage, whereas PPaII tubers did not develop any visible sprout (FIG. 5). While sprout development of wildtype tubers continued, there was still no indication of sprouting in PPaII tubers after twelve months of storage. Even after a prolonged storage of two years, PPaII tubers did not sprout. Treatment of potato tubers with gibberellic acid, ethephon, higher- and lower temperatures or light did not induce sprouting of PPaII tubers.

II. Exemplification of Inducible Gene Expression in Potato Tubers

3. Ethanol Inducible Gene Expression 3.1. Construction of Plasmid Alc:GUS

The source of the GUS gene was the pUC based plasmid pJIT166 (FIG. 6). A fragment containing the GUS coding region and CaMV35S terminator, from pJIT166 was cloned into pACN/pUC vector using SalI and BglII. BglII cuts three times in the CaMV35S terminator. The first cut occurs 250 bases beyond the end of the GUS gene. Although this only takes a small part of the terminator the fragment contains all necessary sequences required for the termination of transcription. The SalI-BglII digest of pJIT166 yielded a 1.8 kbp fragment containing the GUS gene plus the truncated CaMV35S terminator. This fragment was cloned into pACN/pUC digested with SalI and BglII to remove the CAT gene and the nos terminator leaving a SalI overhang at the 5' end behind the alcA promoter and a BglII overhang at the 3' end of the linearised vector. The fragment containing the GUS gene and the CaMV35S terminator was ligated into the linearised pUC vector containing the alcA promoter using standard protocols. The final step in the cloning procedure was to clone the alcA-GUS-35St fragment into pSRN-ACN/BinN19, in place of the alcA-CAT-nos fragment. The resulting Bin19 vector would then contain all the components of the alc regulon but with the GUS reporter. The alcA-CAT-nos fragment was excised from pSRN-ACN/Bin19 vector with a HindIII digestion. The remaining 16.1 kbp fragment, which is the Bin19 vector still with the 35S-alcR-nos region, was extracted from the gel by electro-elution. The alcA-GUS-35St fragment was then excised with a HindIII XmnI double digest of pAGS/pUC. The restriction enzyme XmnI cuts approximately 850 bp off the pUC19 vector giving separation and allowing the removal of the alcA-GUS-35St fragment. The alcA-GUS-35St fragment was then cloned into the vacant HindIII site in pSRN/Bin19. The fragment was orientated using restriction mapping and then sequenced to confirm that they contained the correct sequences. A map of plasmid AlcR/AGUS is provided in FIG. 7.

3.2. Transformation of Construct

Direct transformation of *Agrobacterium tumefaciens* strain C58C1:pGV2260 was done as described by Höfgen and Willmitzer (1988)(J. loc cit.). Potato transformation (Solara) using Agrobacterium-mediated gene transfer was performed as described by Rocha-Sosa et al. (1989) (J. loc cit).

Following Agrobacterium mediated gene transfer 100 independent transformed plants were selected. To test inducibility of the GUS activity shoots of transgenic plants were duplicated in tissue culture. Following root formation one set of plants was transferred into the greenhouse. Two weeks after transfer into the greenhouse ethanol inducibility was assayed by adding 50 ml of a 5% ethanol solution to the root system of the potato plants. Subsequently GUS activity was visualised using the histochemical detection system. Following ethanol induction GUS activity was visible in all tissues tested (sink- and source leaves, stem, roots and stolons). As shown in FIG. 8 GUS activity was highly inducible in developing and mature tubers. There was no detectable GUS activity in any organ in uninduced potato plants.

In order to investigate the sensitivity of the Alc-switch to ethanol vapour an experimental system was used where an Alc-CAT(chloramphenical acetyl transferase) tobacco plant (CaMV35S-AlcR-nos, AlcA-CAT-nos; Caddick et al., 1998) was enclosed in a sealed container with a pot of ethanol of a particular concentration to act as a source of ethanol vapour. Headspace and leaf samples were taken after 24 hours. Absolute amounts of ethanol in the headspace samples was quantified by relating the ethanol peak area obtained after injection using a gas-tight syringe into a gas chromatography machine with a mass spectrometry detector to that with an ethanol standard solution. Total CAT expression levels in leaves were determined by CAT ELISA. CAT expression in tobacco plants enclosed with ethanol solutions of 5, 1, 0.1 and 0.05% were relatively constant but dropped dramatically with 0.01, 0.005 and 0.001% ethanol solutions (see FIG. 28). Relating the levels of CAT activity to ethanol vapour concentrations in the container, the threshold of Alc-switch activation was seen at an ethanol concentration of between 72 and 21 ng/ml air.

To further study the inducibility of GUS in stored potato tubers four GUS positive transgenic lines were selected for a detailed analysis. After multiplication in tissue culture 5 plants of each genotype were transferred to the green house for tuber production. Following harvest tubers were placed in a sealed glass container containing 3MM paper soaked with a 5% ethanol solution.

To prove that ethanol induction would be efficient throughout the whole potato tuber slices were taken at different times following ethanol induction and GUS activity was visualised using the histochemical detection method. As shown in FIG. 9 homogenous induction of GUS activity was found in intact potato tubers.

The use of ethanol vapour to activate the Alc-switch was investigated in Alc-GUS potato tubers (CaMV35S-AlcR-nos, AlcA-GUS-nos). The kinetics of GUS RNA transcript accumulation was determined by northern analysis. Potato tubers were enclosed with an ethanol source for 3, 6, 9, 12, 24, 48 hours and 1 week time points, the ethanol source removed and samples subsequently taken at 2, 3 and 4 week time-points. By varying the concentration of ethanol used for induction in the enclosed system, the timecourse of GUS transcript accumulation can be altered. Using 8 ml of absolute ethanol in a 40 liter container low levels of GUS transcript can first be detected at 6 h in the outer 1–3 mm below the tuber skin and at 12 h 3 mm or more below the skin surface (see FIG. 29). Maximal levels of transcript were detected at 24 h with transcript persisting until 4 weeks. In contrast, using a 5% ethanol solution to generate a lower ethanol vapour concentration transcript is first detected at 1 week. By keeping the a constant ethanol source GUS transcript was detected at high levels through-out the course of the experiment (last time-point 3 months) (see FIG. 30).

An extension of these ethanol vapour studies was to investigate Alc-switch induction in tomato fruit. Using a 5% ethanol solution enclosed in a 2.6 l container with Alc-GUS tomato fruit (CaMV35S-AlcR-nos, AlcA-GUS-nos), significant GUS staining was observed in the walls of the pericarp originating from the stig in fruit after 4 weeks of ethanol exposure. Tomato fruit were sliced, washed briefly in 50 mM sodium phosphate buffer, pH. 7.0 and incubated in staining buffer (50 mM sodium phosphate buffer, pH. 7.0, 50 uM potassium ferricyanide, 50 uM potassium ferrocyanide, 2% triton X100, 20% methanol and 1 mM 5-bromo-4-chloro-3-indolyl-B-D-glucoronide) as required. Staining was stopped by performing 100% and 70% ethanol washes and the fruit slices stored in 70% ethanol at 4° C.

3.3. Fluorometric Determination of GUS Activity

The fluorometric determination of GUS activity was carried out as follows: Tuber slices harvested after the indicated times following ethanol induction were frozen in liquid nitrogen. Subsequently tuber tissue was homogenised in 50 mM NaHPO4 (pH 7.0), 10 mM mercaptoethanol, 10 mM EDTA, 0.1% sodium lauryl sarcosine, 0.1% Triton X-100. The homogenate was centrifuged for 10 minutes at 13.000 rpm at 4° C., the cleared supernatant was collected and used for the determination of protein content and GUS activity. For fluorometric detection 20 $\mu$l of extract (diluted to a proper concentration) was added to 480 $\mu$l GUS assay buffer (2 mM MUG in extraction buffer) and incubated for 30 minutes at 37° C. Thereafter 50 $\mu$l of the reaction mixture was transferred to 1950 $\mu$l stop solution. The fluorimetric signal of each sample was determined with a TKO 100 mini-fluorometer (excitation at 365 nm, emission at 455 nm). From the initial slope of the curve obtained by plotting the fluorometric value against time enzyme activity was calculated. Heat inactivated extract served as controls. The activity values were normalised to the protein concentration of each extract.

3.4. Histochemical Detection of GUS Activity

For histochemical detection of GUS activity tissue samples were incubated in X-gluc buffer (25 mM sodium phosphate buffer (pH 7.2), 25 mM potassium phosphate (pH 7.2), 0.1% Triton X-100, 1 mM X-gluc). Brief vacuum infiltration (30 seconds) was used to support penetration of the substrate into the plant tissue. Subsequently the material was incubated at 37° C. for 3 to 24 hours and rinsed with water before photography. Photosynthetic tissue were bleached with ethanol. Microscopic analysis was performed using an Wild Makroskop M420 equipped with a Wild MPS46 photoautomat.

III. Safener Inducible Gene Expression in Potato Plants 4.1. Construction of GST:GUS Plasmid Standard recombinant DNA methods were adopted in the construction of plasmid vectors. A reporter gene construct containing a GST-27 3.8 kb EcoRI-Nde I 5' flanking region from pG1E7 was blunted ended and ligated into the Sma I site of the Agrobacterium Ti vector pBI101. The Nde I site, which lies at the predicted translation start codon of GST-27 was destroyed after blunting. This formed a convenient point for fusion with the *E coli* UidA gene, encoding b-glucuronidase (GUS) in pBI101. The structure of the resultant chimeric reporter gene construct pGSTTAK was verified by restriction and sequence analysis. A map of plasmid pGSTTAK is provided in FIG. 10.

4.2. Transformation of Construct and Test of Inducibility

Using plasmid pGST::GUS direct transformation of *Agrobacterium tumefaciens* strain C58C1:pGV2260 was done as described by Höfgen and Willmitzer (1988) (J. loc cit). Potato transformation (Solara) using Agrobacterium-mediated gene transfer was performed as described by Rocha-Sosa et al. (1989) (J. loc cit).

Following Agrobacterium mediated gene transfer 100 kanamycin resistant regenerated shoots were selected. Safener inducibility was tested by transferring stem cuttings of GST::GUS transformed potato plants on MS medium containing 0, 0.4, 2.0 and 10% R-25788 (final concentration). Following cultivation for 14 days fully developed leaves were harvested and GUS activity determined. As shown in FIG. 11, a 3 to 20 fold increase in GUS activity could be obtained following safener induction.

IV. Inducible Repression of the Expression of Target Genes

5. Inducible Co-suppression 5.1. Construction of Chimeric Gene for Inducible FNR Co-suppression To achieve ethanol inducible co-suppression of NADP-ferredoxine oxidoreductase (FNR) a ca. 450 base pair 3'-fragment (Seq. 1) of a tobacco FNR cDNA was fused to the alcA promoter in the sense orientation yielding plasmid SQ03. The cloning strategy is illustrated in FIG. 12.

Direct transformation of *Agrobacterium tumefaciens* strain C58C1:pGV2260 was done as described by Höfgen and Willmitzer (1988) (J. loc cit). Tobacco transformation (Samsun) using Agrobacterium—mediated gene transfer was performed as described by Rosahl et al. (EMBO J 6, 23–29, (1987)).

Following Agrobacterium mediated gene transfer 100 independent transformed plants were selected.

Seq. 1 (SEQ ID NO.: 1): Total number of bases 423

```
TTTTTTTTTT TTTTTTTTTT TTTTTTTTTT TTTTTTTTTT TTCCCAAAAA ATGAAATTAA

AATTTCAAAG GAAAAATTTA CCTATCTACA TGGATGCAGG GGGAGAGAAG CATAAAGTTG

GCTCATATTT GTACAAAGAA AAGTAAAAAT ATTTAGTAGA CTTCAACATT CCATTGCTCT

GCCTTCTTCA ATTGCTTCTT GTAGTCCGCC CAGACAATAC CATCTCTTTC AGCAAGAGCA

GACATAATTT CATCAATTCC CTGCTCCATG CCCTTGAGTC CACACATGTA GATGAAGGTG

TTGTCTTTTT GGAGCAAAGT CCATAGTTCT TCAGCATATT GAGCCATTCT GGTTTGAATG

TACATCTTTT CACCCTTTCC GTTCGTTTGC TCTCTGCTCA CAGCAAAGTC CAATCTGAAG

TTT-3'
```

V. Inducible Antisense Repression of Heterologous Genes

As described in section I expression of cytosolic invertase and inorganic pyrophosphatase can lead to a non-sprouting phenotype when suitable promoters are used to drive the expression of the respective gene. To achieve inducible reversion of the non-sprouting phenotype a strategy for the inducible antisense of the heterologous gene was applied.

6. Inducible Antisense Repression of Pyrophosphatase Expression 6.1. Construction of Plasmid SQ01

As shown in FIG. 5 high level expression of *E. coli* inorganic pyrophosphatase leads to a non-sprouting phenotype of harvested potato tubers. To chemically control the expression of *E. coli* inorganic pyrophosphatase plasmid SQ01 was designed. The plasmid contains three chimeric genes: (a) the alcR gene under control of the 35S CaMV promoter, (b) the ppa gene under control of the enhanced 35S CaMV promoter and (c) the ppa gene in the antisense orientation under control of the alcA promoter. The construction of plasmid SQ01 is shown in FIG. 13.

6.2. Plant Transformation

Direct transformation of *Agrobacterium tumefaciens* strain C58C1:pGV2260 was done as described by Höfgen and Willmitzer (1988) (J. loc cit). Potato transformation (Solara) and tobacco (Samsun) using Agrobacterium—mediated gene transfer was performed as described by Rocha-Sosa et al. (1989) (J. loc cit) and as described by Rosahl et al. (1987) (J. loc cit).

Following Agrobacterium mediated gene transfer 100 independent transformed plants were selected.

6.3. Immunological Detection of ppa

The successful transformation was tested by the immunological detection of the *E. coli* pyrophosphatase protein in leaf extracts of tissue culture grown potato plants. Based on the initial screening 15 independent transgenic plants could be identified. Following duplication in tissue culture pyrophosphates expressing transgenic potato plants were transferred into the green house for tuber formation.

7. Inducible Antisense Repression of Invertase Expression 7.1. Construction of Plasmid SQ02

As shown in FIG. 3 phloem-specific expression of cytosolic yeast-derived invertase leads to a non-sprouting phenotype of harvested potato tubers. To chemically control the expression of yeast invertase plasmid SQ02 was created. The plasmid contains three chimeric genes: (a) the alcR gene under control of the 35S CaMV promoter, (b) the truncated suc2 gene encoding the mature invertase protein under control of the rolC promoter and (c) the suc2 gene in the antisense orientation under control of the alcA promoter. The construction of plasmid SQ02 is shown in FIG. 14.

7.2. Plant Transformation

Direct transformation of *Agrobacterium tumefaciens* strain C58C1:pGV2260 was done as described by Höfgen and Willmitzer (1988) (J. loc cit). Potato transformation (Solara) and tobacco (Samsun) using Agrobacterium-mediated gene transfer was performed as described by Rocha-Sosa et al. (1989)(J. loc cit) and as described by Rosahl et al. (1987) (J. loc cit).

Following Agrobacterium mediated gene transfer 100 independent transformed plants were selected.

7.3. Invertase Activity

The successful transformation was tested by the detection of invertase activity in SDS PAA-gels as described in von Schaewen et al. (EMBO J. 9, 3033–3044 (1990)). To this end protein extracts were prepared from midribs of tissue culture grown potato plants. Following separation of the protein extracts in 12.5% SDS PAA gels the gel was washed in 100 mM Na-Acetate buffer pH 5.0 for 30 minutes. Subsequently the gel was incubated in 100 mM Na-Acetate buffer containing 100 mM Sucrose at 37° C. for 1 hour. After a brief wash with distilled water invertase activity was visualised via the detection of liberated reducing sugars (glucose and fructose). Hexoses were detected by boiling the gel in 0.1% 2,3,5-Triphenyltetrazoliumchlorid in 0.5N NaOH for 2–5 minutes. Invertase activity became visible due to the formation of an intense red colour. Based on the initial screening 18 independent transgenic plants could be identified. Following duplication in tissue culture invertase expressing transgenic potato plants were transferred into the green house for tuber formation.

V1. Use of Operator/Repressor System to Repress Heterologous Genes

8. Use of Lac Operator/Repressor System with the rolC Promoter, the Yeast-derived Invertase Gene and the Alc Switch 8.1. Cloning of lacI into ALC Switch Binary Vector As can be seen from FIG. 22, the lacI-nos region was excised from a 35S-LacI-nos plasmid with BamH1/HindIII and cloned into a BamH1/HindIII digested pMSC2 vector.

This vector has a Pst1 site a few bases 5' to the BamH1 site, so a Pst1 digest removed the lacI coding region. This was then cloned into a pst1 digested pACN vector (AlcA-cat-nos), replacing the AlcA gene with the lacI gene, to give a pALN vector (AlcA-lacI-nos). The ALN region was removed from this with a HindIII digest and cloned into a HindIII digested binary SRNACN (35S-AlcR-Nos-AlcA-Cat-Nos) vector, replacing the ACN with the ALN cassette.

8.2. Cloning the lacI Operator into RolC-invertase

Two oligonucleotides (SEQ ID NOS.: 11 and 12) were synthesized with BamHI and Asp718 restriction sites SC24: TTGGTACCAATTGTGAGCGCTCACAATTGGATCCTT SC25: AAGGATCCAATTGTGAGCGCTCACAATTGGTACCAA. 10 uM of both oligonucleotides were annealed by boiling in a water bath in the presence of 20 mM Tris.Cl (pH8.4) 50 mM KCl and 1.5 mM $MgCl_2$ for 5 minutes before cooling down to 30° C. over approximately one hour, followed by 5 minutes on ice. The annealed oligonucleotides were digested with BamH1 and Asp718, and the restriction enzymes inactivated by phenol extraction and ethanol precipitation. The fragments were ligated into BamH1 and Asp718 cut pUC19 to give pUC-lacO. The plasmid was confirmed by sequencing. The OCS terminator was removed from the BINAR plasmid and cloned into the SalI and HindIII restriction sites of plasmid pUC-lacO creating the plasmid pUC-lacO-ocs. The RolC promoter was inserted with EcoRI and Asp718 (KpnI) to give the plasmid pUC-RolC-lacO-ocs. The yeast derived invertase was inserted into the BamHI site of pUC-RolC-lacO-ocs resulting in the plasmid pUC-RolC-lacO-INV-ocs. FIG. 21 shows the cloning strategy for this plasmid.

8.3. Ligation of Above Two Components to Give the Final Binary Vector

The RolCopINVocs cassette is on a HindIII fragment (using the 865bp RolC promoter) and was ligated to a HindIII digested binary SRNAlacI in a three-way ligation, to give the final construct of 35S-AlcR-nos-AlcA-lacI-nos-RolC-op-invertase-ocs.

VII. Additional Targets

Based on known biochemical steps involved in potato tuber sprouting we have identified several additional targets which may be used to create genetically engineered non-sprouting potato tubers. Besides others, respiratory enzymes or membrane proteins involved in the mitochondrial export of metabolites are promising. One of these candidates is the mitochondrial ATP/ADP translocator and a second malate oxoglutarate translocator.

9. Genes Involved in Mitochondrial Function 9.1. Cloning of ATP/ADP Translocator (ANT) and Construction of a Chimeric Antisense Gene Based on a published sequence of potato ADP/ATP translocator (Emmermann et al. (1991) Curr. Genet. 20, 405–410) oligonucleotides were designed to allow PCR-amplification of an internal ANT-fragment (see FIG. 15). The following PCR-primers (SEQ ID NOS: 13 and 14) were used: 5'-ANT primer: 5'-AACGGATCCATGGCAGATATGAACCAGC-3'; 3'-ANT primer: 5'-TTGGATCCTTACAACACACCCGCCCAGGC-3'. To optimise subsequent cloning of the ANT-fragment into plant expression vectors BamHI sites were included in both PCR primers. As template reverse transcript mRNA isolated from growing potato tubers was used. RNA isolation was done according to Logemann et al. (1987; Anal. Biochem., 163, 16–20). Single strand cDNA was synthesised using M-MLV superscript reverse transcriptase according to the instructions of the manufacturer (Gibco, BRL). The temperature profile of the PCR cycle (40 cycles) was as follows: 1 min at 95° C., 1 min at 45° C., and 2 min at 72° C. The amplified DNA was cloned into the PCR vector pCR1000™ (Invitrogen, Norwalk, Conn.). To exclude mutations of the amplified DNA during the PCR cycles, the clone was sequenced using the dideoxy method. The 1120-bp ANT fragment was subsequently cloned into a plant expression cassette pBINAR (Höfgen and Willmitzer Plant Sci. 66 221–230 (1990)) in the antisense orientation (FIG. 15).

9.2 Cloning of Mitochondrial Oxoglutarate Translocator (MOT)

A cDNA fragment encoding MOT was isolated using the methods described in Section 9.1. Northern analysis on FIG. 17 shows the MOT mRNA expression is highest when RNA is extracted immediately below the tuber sprout. This region corresponds to high metabolic activity. An antisense down-regulation construct was prepared by amplifying the MOT fragment essentially as described above in section 8.1 for ANT but using the primers shown in FIG. 18. The BamHI/SalI PCR fragment was cloned into Bam/Sal cut pBluescript SK. To exclude mutations of the amplified DNA during the PCR cycles, the clone was sequenced using the dideoxy method. An Asp718/BamHI fragment was excised from the pBluescript vector described and cloned into BamHI/Asp718 cut pBinAR. This yielded a plant transformation cassette containing the 35S CaMV promoter driving MOT in an antisense orientation.

9.3. Transformation

Direct transformation of *Agrobacterium tumefaciens* strain C58C1:pGV2260 was done as described by Höfgen and Willmitzer (1988) (J. loc cit.). Potato transformation using Agrobacterium—mediated gene transfer was performed as described by Rocha-Sosa et al. (1989)(J. loc cit).

Following Agrobacterium mediated gene transfer 70 independent transformed plants were selected.

10. Genes Induced During Potato Tuber Storage 10.1. Isolation of Genes Induced During Tuber Storage 10.1.1. Differential Display To gain insight into molecular changes occurring during the transition of growing to sprouting tubers the differential display technique was used. To this end total RNA was isolated from growing and stored potato tubers (Desiree). Following DNaseI digestion 5 $\mu$g of total RNA was reverse transcript using M-MLV superscript reverse transcriptase (Gibco, BRL) yielding single strand cDNA templates. Subsequently, PCR amplification of the prepared cDNA templates was carried out in the presence of ($\alpha$-$^{35}$S)dATP using oligo-d(T)11-XN and 100 different RAPD primers. The use of the following RAPD-primers led to the isolation of source tuber-specific cDNA fragments (SEQ ID NOS.: 15 and 17): 5'-AAGCGACCTG-3'; 5'-GTTGGTGGCT-3'; 5'-ACGGGACCTG-3'.

The temperature profile of the PCR cycle (40 cycles) was as follows: 30 seconds at 94° C., 1 min at 42° C., and 30 seconds at 72° C. The amplified DNA was denatured for 5 minutes in formamide buffer at 94° C. and loaded onto a PAA-gel (6% acrylamide, 0.3% bisacrylamide, 7 M urea in TBE buffer). Separation of the cDNA fragments was done at 1.75 KV, 130 mA for 3 hours. Following separation the gel was dried at 80° C. and radioactive labelled cDNA fragments were visualised via autoradiography using Kodak X-OMAT X-ray films. Exposure time ranged from 2 to 5 days. Comparison between cDNA fragments amplified from growing or sprouting tuber templates allowed the detection of cDNA fragments being exclusively present in sprouting potato tubers. Sprouting tuber-specific cDNA fragments were subsequently eluted from the PAAG and reamplified using the respective PCR primers. The reamplified cDNA fragments were subsequently cloned into the PGEMT vector (Promega). The size of the amplified cDNA fragments varied between 200 and 450 base pairs.

10.1.2. Northern Blot Analysis of Genes Induced During Tuber Storage

To verify that the isolated cDNA fragments are induced in stored potato tubers total RNA of growing and 1, 7, 14, 21, 30, 60, 90, 120, 150 and 180 days stored potato tubers was isolated, separated in 1.5% formaldehyde (15% v/v) containing agarose gels and probed for the presence of the respective transcripts following transfer of the RNA onto nylon membranes. As shown in FIG. 16 the transcripts of 4 isolated clones (16-3, 10-1, AC4 and 16-8) accumulate during potato tuber storage.

10.1.4. Construction of cDNA Library

To obtain full size cDNA clones encoding M-1-1, 16-3, 10-1, AC4 and 16-8 a stored tuber-specific cDNA library was constructed. To this end polyA RNA was isolated from potato tubers stored for 5 months at room temperature. cDNA synthesis was carried out using a cDNA synthesis kit from Pharmacia. Following adaptor ligation (EcoRI/NotI-adaptors) the cDNA was ligated into lambda ZAP II vectors following the instructions of the manufacturer (Stratagene). In vitro packaging was carried out using the Gigapack$^2$II Gold packaging extract from Stratagene.

10.1.5. Isolation of cDNA Clones Encoding Stored Tuber-specific cDNA Clones

Following amplification of the primary cDNA library $2\times10^5$ Pfu (plaque forming units) were screened for the presence of phages hybridising to M-1-1, 16-3, 10-1, AC4 and 16-8 PCR-fragments. In all cases several independent phages hybridising to the respective PCR probes were isolated and restriction analysis following in vivo excision of the isolated clones was carried out. In four cases (M1-1, 16-3, 10-1 and 16-8) full size cDNA clones could be obtained. After determination of the complete nucleotide sequences (Seq. 2 to 6) and FIG. 19 a homology search was carried out. Based on homologies clone 16-3 corresponds to ubiquitin carboxyl-terminal hydrolase from human, Drosophila and yeast, clone 10-1 was found to be identical to the ADP-ribosylation factor 1 from potato (belonging to the family of GTP-binding proteins) and clone 16-8 has homologies to a auxin repressed protein of unknown function from strawberries. No homology was found for clone AC4. Differentially expressed clone M-1-1 encodes a protein which we have designated as MOT and which was found to have homology with bovine and human mitochondrial 2-oxoglutarate carrier protein. The sequence comparison is provided in FIG. 20.

10.1.6. Nucleotide Sequence of Induced Clones

Seq. 2 (SEQ ID NO.: 2): 16-3 (homology to ubiquitin carboxyl-terminal hydrolase from human, Drosophila and yeast)

```
GGGCTGCAGGAATTCGAGGCCGCTAGAGAGAGTTAAAATAGAGGAAAGGAATCCATGGCGGAAAGCACAGGCTC

TAAGAAGAGATGGCTTCCTCTTGAAGCTAACCCCGATGTCATGAATCAGTTTCTTTGGGGTCTTGGTGTTCCAC

CGAATGAGGCCGAGTGCTGTGATGTTTATGGGTTAGATGAAGAACTTCTGGAGATGGTGCCAAAGCCAGTGCTT

GCTGTTTTATTTCTCTATCCTCTCACATCTCAGAGTGAAGAAGAGAGAATAAAGCAAGACAGCGAAACAAAGGT

GCAGGATCCCAGTAGTACAGTTTACTACATGAAACAAACAGTGGGAAATGCATGCGGAACAATTGGCCTTCTTC

ATGCTATTGGGAATATCACCTCTCAGATAAAACTTACCGAGGGTTCATTCTTGGACAAGTTCTTTAAATCAACC

TCAAGCATGGACCCAATGCAGCGTGCTTTGTTCCTTGAAAATGATAGGGAAATGGAAGTTGCTCATTCAGTGGC

AGCCACTGCTGGTGATACTGAGGCTACCGACGATGTGAACGCTCATTTCATCTGCTTCACCTGTGTTGATGGAC

AACTCTATGAACTTGATGGAAGGAGGGCTGGACCTATTACACATGGCGCATCCTCTCCAAACAGCTTATTAAAG

GATGCAGCCAGAGTTATCAAAAAGATAATCGAGAAAAATCCAGACTCAATCAACTTCAACGTTATTGCTATTTC

CCAAAACGTTTAGGCCAATCTAGAGGCTTTTATCGATGAGATGGTTTAAACCAATTTTAGCTTTTCATGTTTCT

GCCGTTTCCAGTACTATGTTTCTTCTTGTTTGCAATAAGTTACTTTTGAGAAAAAA
```

Seq. 3 (SEQ ID NO.: 3): 16-8 (homology to auxin-repressed protein from strawberry)

TGTTCTATCCCAGCGGACGCAGAATTTCCTTTTTTATTCTTCTCTTCTTCTCCCCTAAAACGTGAGCCGATTGG

CTAACCTGCACCATGAGCTTACTTGACAAGCTCTGGGACGACACCGTTGCCGGTCCCCTGCCAGATAGTGGCCT

CGGGAAACTCCGGAAGTATTCTACTTTTAGTCCGCGTTCAAATTCCGGCAAGGAATCAGAAGTTTCCACACCGA

GATCCTTCACCGAGGAAGCAAGTGAGGACGTGGTGAAGGTGACGAGAAGTATCATGATAGTAAAGCCTTCCGGG

AGTCAGAATAGAGATTCACCTCCAGTTTCTCCGGCCGGTACTACTCCTCCGGTATCTCCTTTTGCCCCTTCCGC

TGGAAGAGAAGCATTTCGGTTCCGGCGGCGATCAGCGTCATTTGCATACGAGAATGCCAGTGGGGTTGGACCCA

GAAGCCCTCGTCCTCCTTACGACCTGTGAGATATAGTCGGGTTCTCTTTTTTTGTTATCCCTCTTGAGGCGGTT

GAATGTAGTATAGCTAGTCGACATACTCAACATGTTCCTGGTTGAGAGTGTTGTTTTGTGTGGTGTTTAATTTG

TTTGCTTAATTTTGTAAATAGTGCAAGTGGTTCTTCATCTTGCGGATGTTGTGACGAAGGTTTAGCACAAGATG

TAAGCGTCCAAGTTGGTCATGTATTCTGCTTTGTATTAAAAAAAAA

Seq. 4 (SEQ ID NO.: 4): 10-1 (ADP-RIBOSYLATION FACTOR 1 from potato belonging to the family of GTP-binding proteins)

TGGACAATAGAGATCTACTGATTTCATCCTCTCTCATCGGCCGATCTTCGATTAACGGAGATGGGGCTGTCTTT

CACTAAACTCTTTAGTTCGCCTCTTTGCAAGAAAGAAATGCGAATTCTTATGGTTGGTCTCGATGCTGCTGGTA

AAACCACAATTCTGTACAAGCTCAAGTTGGGAGAAATTGTTACCACTATCCCAACCATTGGTTTCAATGTGGAG

ACTGTTGAATACAAAAACATCAGCTTTACTGTGTGGGATGTTGGTGGTCAGGACAAGATTAGACCTCTATGGAG

GCACTATTTCCAGAACACACAGGGCCTCATCTTTGTGGTTGATAGCAATGACAGAGACCGTGTAGTTGAGGCAA

GGGATGAGCTTCACAGGATGTTAAATGAGGATGAATTAAGAGAAGCTGTGTTGCTTGTTTTTGCGAACAAACAA

GATCTTCCAAATGCAATGAATGCNNCTGAAATCACCGACAAGCTTGGCCTTCATTCTCTCAGACAACGACACTG

GTATATCCAGAGTACATGTGCTACTTCTGGAGAAGGGCTATATGAGGGACTGGATTGGCTTTCAAACAACATCG

CCAGCAAGGCCTAATGCAATGGTACTATGCTTCTTGTGTTGCTATATCCGGAGAAATAAACATCATTGTCTCGA

GATTTTAAATATCTGTTCAGCTCACAATTCTGGGGAAGGCCTTACCCTTCTTCACTCTCTATGGTTTATGTCAA

AGACCATGACATAGTTTACACATTGCTGGATGCACATTGGCAATGTAATGATATTTTAGTATAATATCTGGTTT

TGAAACTTGGCGCAGCCGTGTGCACCATTTTGTTGTCCTGTGTGTCTGATGTTGCAATGGGTGTACAAAATGTA

ATACAGATCAATAGTAAGTATCGGA

Seq. 5 (SEQ ID NO.: 5): AC4: (no homology)

ACGGGACCTGGTCAATACTAATGTATCAGTCAACCAGCTCGAAAATCCACAAAATATAGAAGGGGAGGGAGGAT

CACCAAGGATAAACCATCTGAACCCAGACGACAACCTCCTTCTTCTTCTTCGATCCCTTAGGGAAGAGATACCC

CGATCACCTGGATTAGGAAATAAGAGGAGCAAAATAACTTCAGAAACAGGAGGAATAAAGAGATCTAGTAAGGA

GAGGGGAAGCACAAACTCTGAACCTTGGAAATGTGAAGCAGAGTAATGGTCTAACAGAGTTCACCATCGACTAG

TGGAAGCACAAGCATAAGAACATCCAAAGGAGAAGGAGCTTAAGTCGGTGGTTCCAGCGACATG

Seq. 6 (SEQ ID NO.: 6): MOT Variant

GAATTCGCGGCCGCAAGAGAAAGAGAGCTGAGAAAGAATGGGTGAGAAGCCAGTATCTGGAGGTGTTTGGCCTA

CTGTTAAGCCATTTATTAATGGAGGTGTTTCTGGTATGCTTGCTACCTGTGTTATTCAGCCTATTGATATGATA

AAGGTGAGGATACAATTGGGACAGGGATCAGCAGCTGATGTTACCAAAACCATGCTTAAAAATGAAGGCTTTGG

-continued

```
TGCCTTTTACAAGGGTCTGTCAGCTGGGCTTCTTAGGCAGGCAACCTACACAACTGCCCGACTTGGGTCATTCA

GAATTTTGACGAACAAGGCCATTGAGGCTAATGAAGGGAAGCCCTTACCTCTGTACCAAAAGGCTTTGTGTGGT

CTAACTGCTGGAGCAATTGGTGCAACTGTTGGCAGTCCAGCAGATTTGGCCCTCATTCGTATGCAAGCTGATGC

TACCTTGCCTTTAGCACAGAGACGCAATTACACAAATGCATTCCATGCACTCTCCCGTATTGCGGTTGATGAGG

GAGTTCTAGCCCTCTGGAAAGGTGCTGGCCCAACAGTAGTAAGGGCAATGGCATTGAACATGGGTATGCTTGCC

TCTTATGATCAGAGTGTGGAGTTCTTCAGGGACAACCTTGGCATGGGCGAGGCTGCTACAGTAGTAGGGGCCAG

CAGTGTCTCTGGGTTCTTTGCTGCTGCTTGCAGTTTACCATTTGATTACGTCAAGACCCAGATTCAGAAAATGC

AGCCAGATGCTGAAGGAAAATTGCCCTACACTGGTTCTTTCGATTGTGCCATGAAGACTTTGAAGGCAGGAGGA

CCCTTCAAATTTTACACTGGATTTCCAGTATATTGTATTAGGATTGCCCCTCATGTTATGATGACTTGGATTTT

CCTTAACCAAATTCAGAAGGTGGAGAAGAAAATCGGATTGTGATTGTTGCAAAAAAAGATACATCCTCTCAA

GTTGAGCTTTATTAGAAATAACATCTTCGCCTTGTTGTATTAGTACTGTTTTCGCTCTTTCTTTATCCTCACGC

CTTCAAAGGCTTTAAGATTTTTGTGGTGATACATTGACTCGCGGAAATTTAGGGTTAGACATTTGGTCTTTTCA

ATATTCCTACCAATATAGTTTTGGGAAGATTACTTTATCCAAACTGATGGGAAGATTCTTTTAGCTGAATAATC

TATGTACTTCAAAAACCGTCTTGAAGTAGGTAGTATGGAGTTCACCAATTTTGGTGTCATCTTGAACTTGATCT

TGTTGCCTATTTTTGGATATACACTCATTTGTTAGCATCCTTCCTGGTATGAGCTATTGAGTATTATTGGAGTA

AAAATGCATCCTAATGTTCTTGCTCCATTTGGATATATAGTTTTTCATGCACCGCGGCCGCGAATTC
```

VIII. Identification of Promoter Regions

11. Isolation of Genomic Clones 11.1 A genomic library of *Solanum tuberosum* var. Solara in Zap-Express Vectors (Stratagene) (750 000 Plaques were screened) was screened. cDNA fragments from the differential display were used as probes.

11.1.1. UBL (FIG. 23)

Three phage were isolated in the third screen, the in vivo preparation revealed that two of them were identical and the third did not contain 5, region of the UBL gene. One of the two identical phage was used for a PCR-approach. The clone was sequenced with an oligonucleotide (SEQ ID NO.: 18) (GCT TTC CGC CCA TGG ATT CC) reading into the promoter. From this sequence, an additional oligonucleotide was deduced (a BamHI-site added) and used to make a PCR with the reverse-primer (Stratagene). The fragment was cloned into pGemT (Promega) and sequenced. The cloning into the pBI101 (Jefferson et al. 1987 EMBO 6) was made as BamHI fragment. Transgenic potato lines were generated containing the UBL promoter GUS construct as described previously. No detectable GUS activity was observed in a variety of tissue including stem and leaf. Tubers were harvested and a number of transgenic lines were found to exhibit GUS expression.

11.1.2. MOT (FIG. 24)

Six clones were isolated from the library. Two of them were to be sequenced with a gene-specific primer (SEQ ID NO.: 19) (CCA GGA GAT GGG AAT GGA GAC CG), oligonucleotides were deduced for both clones. MOT6 and MOT3 fragments were isolated in combination with a universal Primer (Stratagene) and cloned into pGemT. MOT3 was cloned as BamHI fragment in pBI 101, MOT6 as BamHI/XbaI fragment.

12. Construction of Antisense/Sense Constructs 12.1.1. UBL-antisense Construct A BamHI (internal restriction-site bp 301)/Asp718 (at 3-Prime end of the cDNA in the vector pBluescript) fragment was cloned into pBinAR. pBinAR is a derivative of pBin19, containing a 35S-Promoter (Hoefgen und Willmitzer 1990, Plant Sci., 66,221–230).

12.1.2. MOT-antisense/sense Constructs

Oligonucleotides with restriction sites 5 prime BamHI base pairs 292–315 of cDNA and 3 prime SalI base pairs 993–969 were used for PCR. Th following fragments were cloned into pGemT:—BamHI/SalI-fragment in pBinAR (sense) and pBluescript (stratagene) and BamHI/Asp718 fragment from pBluescript in pBinAR (antisense).

12.1.3.16-8 sense/antisense Constructs

Oligonucleotides with a restriction site 5 prime BamHI bp 6–29 cDNA and 3 prime XbaI (sense) or Asp718 (antisense) bp 682–662 cDNA were used. Fragments were cloned into pGemT, and from there into pBinAR.

12.1.4. UBL-1, MOT6 and MOT6 Promoter Sequences

The sequences of these promoters are given in FIGS. 25, 26 and 27.

Other modifications of the present invention will be apparent to those skilled in the art without departing from the scope of the present invention.

What is claimed is:

1. A method for the selective induction or suppression of sprouting in a vegetative storage organ of a plant comprising incorporating into the genome of said plant by transformation a DNA construct comprising a first polynucleotide sequence comprising at least one DNA sequence encoding an invertase or an inorganic pyrophosphatase operably linked to a tissue or organ selective promoter region and optionally to a transcription terminator region and a second polynucleotide sequence comprising at least one DNA sequence operably linked to and controlled by a controllable promoter region and optionally to a transcription terminator region whereby the DNA sequence(s) in said first polynucleotide sequence is expressed during dormancy of the vegetative organ derived from said transgenic plant resulting in effective suppression of sprouting and the said suppression is neutralised by inducing expression of the DNA sequence (s) in said second polynucleotide sequence from said controllable promoter region by external application of an inducing substance thus making restoration of sprouting of said vegetative storage organ dependent on the application of the inducer, so that sprouting is selectively induced or suppressed.

2. A method according to claim 1 for the selective induction or suppression of sprouting in potatoes comprising forming a transgenic potato by incorporating into the genome of a potato by transformation a DNA construct comprising a first polynucleotide sequence comprising at least one DNA sequence encoding an invertase or an inorganic pyrophosphatase operably linked to a tissue or organ selective promoter region and optionally to a transcription terminator region and a second polynucleotide sequence comprising at least one DNA sequence operably linked to and controlled by a controllable promoter region and optionally to a transcription terminator region whereby the DNA sequence(s) in said first polynucleotide sequence is expressed during dormancy of the tuber derived from said transgenic potato resulting in effective suppression of sprouting and the said suppression is neutralised by inducing expression of the DNA sequence(s) in said second polynucleotide sequence from said controllable promoter region by external application of an inducing substance thus making restoration of sprouting of said tuber dependent on the application of the inducer, so that sprouting in said transgenic potato is selectively induced or suppressed.

3. A method according to claim 1 wherein the DNA sequence(s) in said first polynucleotide sequence comprises a DNA sequence coding for an inorganic pyrophosphatase derived from plant, bacterial or fugal sources, or an invertase derived from plant, bacterial or fungal sources.

4. A method according to claim 1 wherein the DNA sequence(s) in said second polynucleotide sequence comprises a DNA sequence which is selected from the group consisting of: a sense sequence with respect to said first DNA sequence, an anti-sense sequence with respect to said first DNA sequence a partial sense sequence with respect to said first DNA sequence and a DNA sequence which is capable of causing suppression of said first DNA sequence.

5. A method according to claim 1 wherein the tissue or organ selective promoter is the rolC promoter or a tuber promoter.

6. A method according to claim 1 wherein the DNA sequence(s) in the second polynucleotide sequence of the construct is under the control of a controllable promoter region which may be induced chemically by the application of an external chemical stimulus.

7. A method according to claim 6 wherein the controllable promoter region is the alcA/alcR or GST or ecdysone switch promoter.

8. A method according to any one of claim 1 wherein said first polynucleotide sequence comprises a further DNA sequence coding for an operator sequence operably linked to the first DNA sequence and the second polynucleotide sequence comprises a DNA sequence coding for a repressor protein capable of binding to said operator sequence.

9. A method according to claim 8 wherein said operator and repressor sequences comprise the lactose, tetracycline or lambda 434 operator/repressor sequences and mutants thereof.

* * * * *

SEQUENCE LISTING

<160> NUMBER OF SEQ ID NOS: 39

<210> SEQ ID NO 1
<211> LENGTH: 423
<212> TYPE: DNA
<213> ORGANISM: Tobacco FNR cDNA

<400> SEQUENCE: 1

```
tttttttttt tttttttttt tttttttttt tttttttttt ttcccaaaaa atgaaattaa     60
aatttcaaag gaaaaattta cctatctaca tggatgcagg gggagagaag cataaagttg    120
gctcatattt gtacaaagaa aagtaaaaat atttagtaga cttcaacatt ccattgctct    180
gccttcttca attgcttctt gtagtccgcc cagacaatac catctctttc agcaagagca    240
gacataattt catcaattcc ctgctccatg cccttgagtc cacacatgta gatgaaggtg    300
ttgtcttttt ggagcaaagt ccatagttct tcagcatatt gagccattct ggtttgaatg    360
tacatctttt caccctttcc gttcgtttgc tctctgctca cagcaaagtc caatctgaag    420
ttt                                                                  423
```

<210> SEQ ID NO 2
<211> LENGTH: 870
<212> TYPE: DNA
<213> ORGANISM: Artificial Sequence
<220> FEATURE:
<223> OTHER INFORMATION: Homology to ubiquitin carboxyl-terminal hydrolase from human, Drosophila and yeast

<400> SEQUENCE: 2

```
gggctgcagg aattcgaggc cgctagagag agttaaaata gaggaaagga atccatggcg     60
gaaagcacag gctctaagaa gagatggctt cctcttgaag ctaaccccga tgtcatgaat    120
cagtttcttt ggggtcttgg tgttccaccg aatgaggccg agtgctgtga tgtttatggg    180
ttagatgaag aacttctgga gatggtgcca aagccagtgc ttgctgtttt atttctctat    240
cctctcacat ctcagagtga agaagagaga ataaagcaag acagcgaaac aaaggtgcag    300
gatcccagta gtacagttta ctacatgaaa caaacagtgg gaaatgcatg cggaacaatt    360
ggccttcttc atgctattgg gaatatcacc tctcagataa aacttaccga gggttcattc    420
ttggacaagt tctttaaatc aacctcaagc atggacccaa tgcagcgtgc tttgttcctt    480
gaaaatgata gggaaatgga agttgctcat tcagtggcag ccactgctgg tgatactgag    540
gctaccgacg atgtgaacgc tcatttcatc tgcttcacct gtgttgatgg acaactctat    600
gaacttgatg gaaggagggc tggacctatt acacatggcg catcctctcc aaacagctta    660
ttaaaggatg cagccagagt tatcaaaaag ataatcgaga aaaatccaga ctcaatcaac    720
ttcaacgtta ttgctatttc ccaaaacgtt taggccaatc tagaggcttt tatcgatgag    780
atggtttaaa ccaattttag cttttcatgt ttctgccgtt tccagtacta tgtttcttct    840
tgtttgcaat aagttacttt tgagaaaaaa                                     870
```

<210> SEQ ID NO 3
<211> LENGTH: 712
<212> TYPE: DNA
<213> ORGANISM: Artificial Sequence
<220> FEATURE:
<223> OTHER INFORMATION: Homology to auxin-repressed protein from strawberry

<400> SEQUENCE: 3
tgttctatcc cagcggacgc agaatttcct tttttattct tctcttcttc tcccctaaaa 60
cgtgagccga ttggctaacc tgcaccatga gcttacttga caagctctgg gacgacaccg 120
ttgccggtcc cctgccagat agtggcctcg ggaaactccg gaagtattct acttttagtc 180
cgcgttcaaa ttccggcaag gaatcagaag tttccacacc gagatccttc accgaggaag 240
caagtgagga cgtggtgaag gtgacgagaa gtatcatgat agtaaagcct tccgggagtc 300
agaatagaga ttcacctcca gtttctccgg ccggtactac tcctccggta tctccttttg 360
ccggttccgc tggaagagaa gcatttcggt tccggcggcg atcagcgtca tttgcatacg 420
agaatgccag tggggttgga cccagaagcc ctcgtcctcc ttacgacctg tgagatatag 480
tcgggttctc ttttttgtt atccctcttg aggcggttga atgtagtata gctagtcgac 540
atactcaaca tgttcctggt tgagagtgtt gttttgtgtg gtgtttaatt tgtttgctta 600
attttgtaaa tagtgcaagt ggttcttcat cttgcggatg ttgtgacgaa ggtttagcac 660
aagatgtaag cgtccaagtt ggtcatgtat tctgctttgt attaaaaaaa aa 712

<210> SEQ ID NO 4
<211> LENGTH: 913
<212> TYPE: DNA
<213> ORGANISM: Artificial Sequence
<220> FEATURE:
<223> OTHER INFORMATION: ADP-RIBOSYLATION FACTOR 1 from potato belonging to the family of GTP-binding proteins
<221> NAME/KEY: misc_feature
<222> LOCATION: (468)..(469)
<223> OTHER INFORMATION: Nucleotides 468 and 469 are "n" wherein "n" = any nucleotide.

<400> SEQUENCE: 4
tggacaatag agatctactg atttcatcct ctctcatcgg ccgatcttcg attaacggag 60
atggggctgt ctttcactaa actctttagt tcgcctcttt gcaagaaaga aatgcgaatt 120
cttatggttg gtctcgatgc tgctggtaaa accacaattc tgtacaagct caagttggga 180
gaaattgtta ccactatccc aaccattggt ttcaatgtgg agactgttga atacaaaaac 240
atcagcttta ctgtgtggga tgttggtggt caggacaaga ttagacctct atggaggcac 300
tatttccaga acacacaggg cctcatcttt gtggttgata gcaatgacag agaccgtgta 360
gttgaggcaa gggatgagct tcacaggatg ttaaatgagg atgaattaag agaagctgtg 420
ttgcttgttt ttgcgaacaa acaagatctt ccaaatgcaa tgaatgcnnc tgaaatcacc 480
gacaagcttg gccttcattc tctcagacaa cgacactggt atatccagag tacatgtgct 540
acttctggag aagggctata tgagggactg gattggcttt caaacaacat cgccagcaag 600
gcctaatgca atggtactat gcttcttgtg ttgctatatc cggagaaata aacatcattg 660
tctcgagatt ttaaatatct gttcagctca caattctggg gaaggcctta cccttcttca 720
ctctctatgg tttatgtcaa agaccatgac atagtttaca cattgctgga tgcacattgg 780
caatgtaatg atattttagt ataatatctg gttttgaaac ttggcgcagc cgtgtgcacc 840
attttgttgt cctgtgtgtc tgatgttgca atgggtgtac aaaatgtaat acagatcaat 900
agtaagtatc gga 913

<210> SEQ ID NO 5
<211> LENGTH: 360
<212> TYPE: DNA
<213> ORGANISM: Artificial Sequence -continued
<220> FEATURE:
<223> OTHER INFORMATION: AC4, no homology.

<400> SEQUENCE: 5

```
acgggacctg gtcaatacta atgtatcagt caaccagctc gaaaatccac aaaatataga     60
aggggaggga ggatcaccaa ggataaacca tctgaaccca gacgacaacc tccttcttct    120
tcttcgatcc cttagggaag agataccccg atcacctgga ttaggaaata agaggagcaa    180
aataacttca gaaacaggag gaataaagag atctagtaag gagaggggaa gcacaaactc    240
tgaaccttgg aaatgtgaag cagagtaatg gtctaacaga gttcaccatc gactagtgga    300
agcacaagca taagaacatc caaaggagaa ggagcttaag tcggtggttc cagcgacatg    360
```

<210> SEQ ID NO 6
<211> LENGTH: 1398
<212> TYPE: DNA
<213> ORGANISM: Artificial Sequence
<220> FEATURE:
<223> OTHER INFORMATION: MOT Variant.

<400> SEQUENCE: 6

```
gaattcgcgg ccgcaagaga aagagagctg agaaagaatg ggtgagaagc cagtatctgg     60
aggtgtttgg cctactgtta agccatttat taatggaggt gtttctggta tgcttgctac    120
ctgtgttatt cagcctattg atatgataaa ggtgaggata caattgggac agggatcagc    180
agctgatgtt accaaaacca tgcttaaaaa tgaaggcttt ggtgcctttt acaagggtct    240
gtcagctggg cttcttaggc aggcaaccta cacaactgcc cgacttgggt cattcagaat    300
tttgacgaac aaggccattg aggctaatga agggaagccc ttacctctgt accaaaaggc    360
tttgtgtggt ctaactgctg gagcaattgg tgcaactgtt ggcagtccag cagatttggc    420
cctcattcgt atgcaagctg atgctacctt gcctttagca cagagacgca attacacaaa    480
tgcattccat gcactctccc gtattgcggt tgatgaggga gttctagccc tctggaaagg    540
tgctggccca acagtagtaa gggcaatggc attgaacatg ggtatgcttg cctcttatga    600
tcagagtgtg gagttcttca gggacaacct tggcatgggc gaggctgcta cagtagtagg    660
ggccagcagt gtctctgggt tctttgctgc tgcttgcagt ttaccatttg attacgtcaa    720
gacccagatt cagaaaatgc agccagatgc tgaaggaaaa ttgccctaca ctggttcttt    780
cgattgtgcc atgaagactt tgaaggcagg aggacccttc aaattttaca ctggatttcc    840
agtatattgt attaggattg cccctcatgt tatgatgact tggattttcc ttaaccaaat    900
tcagaaggtg gagaagaaaa tcggattgtg attgttgcaa aaaaagatac atcctctcaa    960
gttgagcttt attagaaata acatcttcgc cttgttgtat tagtactgtt ttcgctcttt   1020
ctttatcctc acgccttcaa aggctttaag atttttgtgg tgatacattg actcgcggaa   1080
atttagggtt agacatttgg tcttttcaat attcctacca atatagtttt gggaagatta   1140
ctttatccaa actgatggga agattctttt agctgaataa tctatgtact tcaaaaaccg   1200
tcttgaagta ggtagtatgg agttcaccaa ttttggtgtc atcttgaact tgatcttgtt   1260
gcctattttt ggatatacac tcatttgtta gcatccttcc tggtatgagc tattgagtat   1320
tattggagta aaaatgcatc ctaatgttct tgctccattt ggatatatag ttttttcatg   1380
caccgcggcc gcgaattc                                                 1398
```

<210> SEQ ID NO 7
<211> LENGTH: 34
<212> TYPE: DNA

```
<213> ORGANISM: Artificial Sequence
<220> FEATURE:
<223> OTHER INFORMATION: 5'-rolC primer.

<400> SEQUENCE: 7

ggaattcgat acgaaaaagg caagtgccag ggcc                                  34


<210> SEQ ID NO 8
<211> LENGTH: 29
<212> TYPE: DNA
<213> ORGANISM: Artificial Sequence
<220> FEATURE:
<223> OTHER INFORMATION: 3'-rolC primer.

<400> SEQUENCE: 8

cccatggtac cccataactc gaagcatcc                                        29


<210> SEQ ID NO 9
<211> LENGTH: 45
<212> TYPE: DNA
<213> ORGANISM: Artificial Sequence
<220> FEATURE:
<223> OTHER INFORMATION: 5'-Suc2 d oligonucleotides.

<400> SEQUENCE: 9

gagctgcaga tggcaaacga aactagcgat agacctttgg tcaca                      45


<210> SEQ ID NO 10
<211> LENGTH: 42
<212> TYPE: DNA
<213> ORGANISM: Artificial Sequence
<220> FEATURE:
<223> OTHER INFORMATION: 3'-Suc2 d oligonucleotides.

<400> SEQUENCE: 10

gagactagtt tataacctct attttacttc ccttacttgg aa                         42


<210> SEQ ID NO 11
<211> LENGTH: 36
<212> TYPE: DNA
<213> ORGANISM: Artificial Sequence
<220> FEATURE:
<223> OTHER INFORMATION: Oligonucleotide synthesized with BamHI and
      Asp718 restriction sites.

<400> SEQUENCE: 11

ttggtaccaa ttgtgagcgc tcacaattgg atcctt                                36


<210> SEQ ID NO 12
<211> LENGTH: 36
<212> TYPE: DNA
<213> ORGANISM: Artificial Sequence
<220> FEATURE:
<223> OTHER INFORMATION: Oligonucleotide synthesized with BamHI and
      Asp718 restriction sites.

<400> SEQUENCE: 12

aaggatccaa ttgtgagcgc tcacaattgg taccaa                                36


<210> SEQ ID NO 13
<211> LENGTH: 28
<212> TYPE: DNA
<213> ORGANISM: Artificial Sequence
<220> FEATURE:
<223> OTHER INFORMATION: 5'-ANT primer.
```

<400> SEQUENCE: 13
aacggatcca tggcagatat gaaccagc 28

<210> SEQ ID NO 14
<211> LENGTH: 29
<212> TYPE: DNA
<213> ORGANISM: Artificial Sequence
<220> FEATURE:
<223> OTHER INFORMATION: 3'-ANT primer.

<400> SEQUENCE: 14
ttggatcctt acaacacacc cgcccaggc 29

<210> SEQ ID NO 15
<211> LENGTH: 10
<212> TYPE: DNA
<213> ORGANISM: Artificial Sequence
<220> FEATURE:
<223> OTHER INFORMATION: Tuber-specific cDNA fragments.

<400> SEQUENCE: 15
aagcgacctg 10

<210> SEQ ID NO 16
<211> LENGTH: 10
<212> TYPE: DNA
<213> ORGANISM: Artificial Sequence
<220> FEATURE:
<223> OTHER INFORMATION: Tuber-specific cDNA fragments.

<400> SEQUENCE: 16
gttggtggct 10

<210> SEQ ID NO 17
<211> LENGTH: 10
<212> TYPE: DNA
<213> ORGANISM: Artificial Sequence
<220> FEATURE:
<223> OTHER INFORMATION: Tuber-specific cDNA fragments.

<400> SEQUENCE: 17
acgggacctg 10

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide.

<400> SEQUENCE: 18
gctttccgcc catggattcc 20

<210> SEQ ID NO 19
<211> LENGTH: 23
<212> TYPE: DNA
<213> ORGANISM: Artificial Sequence
<220> FEATURE:
<223> OTHER INFORMATION: Gene specific primer.

<400> SEQUENCE: 19
ccaggagatg ggaatggaga ccg 23

<210> SEQ ID NO 20
<211> LENGTH: 42

-continued

```
<212> TYPE: DNA
<213> ORGANISM: Artificial Sequence
<220> FEATURE:
<223> OTHER INFORMATION: Plasmid pBIN-IN8.

<400> SEQUENCE: 20

aaggttcatt cccttcattt tatccttaat atttgatcag ag                          42


<210> SEQ ID NO 21
<211> LENGTH: 30
<212> TYPE: DNA
<213> ORGANISM: Artificial Sequence
<220> FEATURE:
<223> OTHER INFORMATION: BamHI.

<400> SEQUENCE: 21

ggatccccca tcgaattcct gcagatggca                                        30


<210> SEQ ID NO 22
<211> LENGTH: 24
<212> TYPE: DNA
<213> ORGANISM: Artificial Sequence
<220> FEATURE:
<223> OTHER INFORMATION: BamHI.

<400> SEQUENCE: 22

tagaggttat aaactagagg atcc                                              24


<210> SEQ ID NO 23
<211> LENGTH: 20
<212> TYPE: DNA
<213> ORGANISM: Artificial Sequence
<220> FEATURE:
<223> OTHER INFORMATION: Oligonucleotide.

<400> SEQUENCE: 23

caggaaacag ctatgaccat                                                   20


<210> SEQ ID NO 24
<211> LENGTH: 30
<212> TYPE: DNA
<213> ORGANISM: Artificial Sequence
<220> FEATURE:
<223> OTHER INFORMATION: Oligonucleotide.

<400> SEQUENCE: 24

tctagaaagc ttgtaaaacg acggccagtg                                        30


<210> SEQ ID NO 25
<211> LENGTH: 32
<212> TYPE: DNA
<213> ORGANISM: Artificial Sequence
<220> FEATURE:
<223> OTHER INFORMATION: BamHI oligonucleotide.

<400> SEQUENCE: 25

atggatccgg agaaacccca atttcagctc cg                                     32


<210> SEQ ID NO 26
<211> LENGTH: 32
<212> TYPE: DNA
<213> ORGANISM: Artificial Sequence
<220> FEATURE:
<223> OTHER INFORMATION: SaII oligonucleotide.

<400> SEQUENCE: 26
```

-continued

```
atgtcgaccg gctcgaccaa catgttcata ac                                32

<210> SEQ ID NO 27
<211> LENGTH: 1351
<212> TYPE: DNA
<213> ORGANISM: Artificial Sequence
<220> FEATURE:
<223> OTHER INFORMATION: DNA sequence encoding MOT isolated from potato.
<221> NAME/KEY: CDS
<222> LOCATION: (1)..(1350)

<400> SEQUENCE: 27

cgg cgt ccc aca ctt cgc atc tat agc ttt cgg tct cca ttc cca tct      48
Arg Arg Pro Thr Leu Arg Ile Tyr Ser Phe Arg Ser Pro Phe Pro Ser
1               5                   10                  15

cct ggt ttc cag tga gat gaa ctc taa ttc caa ttg ggc tta aac ctt      96
Pro Gly Phe Gln     Asp Glu Leu     Phe Gln Leu Gly Leu Asn Leu
            20                      25                  30

tga ttc att cta ttt ttt ttt ttc tat ttt ttc cat tac cta att cat     144
    Phe Ile Leu Phe Phe Phe Phe Tyr Phe Phe His Tyr Leu Ile His
                    35                  40                  45

att cat tct ttt ttt aaa aaa agc ttt cgt ctc gat tca ttt ggt ata     192
Ile His Ser Phe Phe Lys Lys Ser Phe Arg Leu Asp Ser Phe Gly Ile
                50                  55                  60

atg ggt gtt aag gga ttt gtt gaa gga ggt att gct tcg att att gct     240
Met Gly Val Lys Gly Phe Val Glu Gly Gly Ile Ala Ser Ile Ile Ala
            65                  70                  75

ggt tgt agt act cac cca ctt gat tta atc aaa gtc cgt atg cag ctt     288
Gly Cys Ser Thr His Pro Leu Asp Leu Ile Lys Val Arg Met Gln Leu
        80                  85                  90

cag gga gaa acc cca att tca gct ccg gcg act gtt cac aat ctc cgt     336
Gln Gly Glu Thr Pro Ile Ser Ala Pro Ala Thr Val His Asn Leu Arg
    95                  100                 105

cca gca ctt gct ttt cac act ggt gct gct aat cat act ttt tcc att     384
Pro Ala Leu Ala Phe His Thr Gly Ala Ala Asn His Thr Phe Ser Ile
110                 115                 120                 125

ccg gcg ccg tcg gtg gtt gct cca ccg cgt gta gga ccg gtt tct gta     432
Pro Ala Pro Ser Val Val Ala Pro Pro Arg Val Gly Pro Val Ser Val
                130                 135                 140

ggt gtt aag att att caa caa gaa gga gtt gct gct ttg ttc tcc ggt     480
Gly Val Lys Ile Ile Gln Gln Glu Gly Val Ala Ala Leu Phe Ser Gly
            145                 150                 155

gta tca gct act gtt ctc cgg aca gac act tta ctc tac aac cag aat     528
Val Ser Ala Thr Val Leu Arg Thr Asp Thr Leu Leu Tyr Asn Gln Asn
        160                 165                 170

ggg ttt ata cga tat gct gaa gca aaa atg gac cga tcc aga tac tac     576
Gly Phe Ile Arg Tyr Ala Glu Ala Lys Met Asp Arg Ser Arg Tyr Tyr
    175                 180                 185

atc atg cct ttg tcg aag aag atc gtt gcc gga tta atc gcc ggc ggg     624
Ile Met Pro Leu Ser Lys Lys Ile Val Ala Gly Leu Ile Ala Gly Gly
190                 195                 200                 205

atc gga gct gcc gtc ggt aat ccc gcc gat gta gcg atg gtc cgc atg     672
Ile Gly Ala Ala Val Gly Asn Pro Ala Asp Val Ala Met Val Arg Met
                210                 215                 220

caa gct gac ggc cgg ctt ccg atc tct caa cgc cgc aac tac aaa agc     720
Gln Ala Asp Gly Arg Leu Pro Ile Ser Gln Arg Arg Asn Tyr Lys Ser
            225                 230                 235

gtg atc gat gca att tct cag atg agt aaa agc gaa ggg gta act agc     768
Val Ile Asp Ala Ile Ser Gln Met Ser Lys Ser Glu Gly Val Thr Ser
        240                 245                 250

ctg tgg cgc ggt tca tct ctt act gtg aac cgc gcc atg cta gtt acc     816
```

-continued

```
Leu Trp Arg Gly Ser Ser Leu Thr Val Asn Arg Ala Met Leu Val Thr
    255                 260                 265

gca tcg cag cta gca tcg tac gat cag ttc aaa gag act atc ctc gag      864
Ala Ser Gln Leu Ala Ser Tyr Asp Gln Phe Lys Glu Thr Ile Leu Glu
270                 275                 280                 285

aag ggg tta atg aag gat ggg ctt ggg aca cat gtg act tcg agt ttt      912
Lys Gly Leu Met Lys Asp Gly Leu Gly Thr His Val Thr Ser Ser Phe
                290                 295                 300

gct gct ggg ttt gtg gcg gcg gtg gca tcg aat cca gtg gat gtg att      960
Ala Ala Gly Phe Val Ala Ala Val Ala Ser Asn Pro Val Asp Val Ile
            305                 310                 315

aag aca cgt gtt atg aac atg aag gtc gag ccg gaa atg gcc cca ccg     1008
Lys Thr Arg Val Met Asn Met Lys Val Glu Pro Glu Met Ala Pro Pro
        320                 325                 330

tat aat ggg gcc att gat tgt gca atg aaa act atc aaa gct gag ggg     1056
Tyr Asn Gly Ala Ile Asp Cys Ala Met Lys Thr Ile Lys Ala Glu Gly
    335                 340                 345

cca atg gca ttg tat aag gga ttt att cct aca atc tca agg caa ggt     1104
Pro Met Ala Leu Tyr Lys Gly Phe Ile Pro Thr Ile Ser Arg Gln Gly
350                 355                 360                 365

cca ttt act gtg gtg ctc ttt gtc aca ctg gaa caa gtc agg aaa atg     1152
Pro Phe Thr Val Val Leu Phe Val Thr Leu Glu Gln Val Arg Lys Met
                370                 375                 380

ctc aag gat ttt taa tga tga tga cga aga aaa aaa aaa tta atg gga     1200
Leu Lys Asp Phe                 Arg Arg Lys Lys Lys Leu Met Gly
            385                                 390

ttt tag tat taa gaa ttt aaa aaa aag tta agt tta att tat gtt ttt     1248
Phe     Tyr     Glu Phe Lys Lys Lys Leu Ser Leu Ile Tyr Val Phe
        395                     400                 405

aag ttt tta agt ttg gga aaa gtg ata cta tgt tgt gtt cta ata tta     1296
Lys Phe Leu Ser Leu Gly Lys Val Ile Leu Cys Cys Val Leu Ile Leu
        410                 415                 420

tta tta ttg tta ctt cta tat gaa aaa tga gtt ctt gtt tgg tgg aaa     1344
Leu Leu Leu Leu Leu Leu Tyr Glu Lys     Val Leu Val Trp Trp Lys
    425                 430                             435

aaa aaa a                                                           1351
Lys Lys
    440


<210> SEQ ID NO 28
<211> LENGTH: 20
<212> TYPE: PRT
<213> ORGANISM: Artificial Sequence
<220> FEATURE:
<223> OTHER INFORMATION: Amino acid sequence encoding MOT isolated from
      potato.

<400> SEQUENCE: 28

Arg Arg Pro Thr Leu Arg Ile Tyr Ser Phe Arg Ser Pro Phe Pro Ser
1               5                   10                  15

Pro Gly Phe Gln
            20


<210> SEQ ID NO 29
<211> LENGTH: 7
<212> TYPE: PRT
<213> ORGANISM: Artificial Sequence
<220> FEATURE:
<223> OTHER INFORMATION: Amino acid sequence encoding MOT isolated from
      potato.

<400> SEQUENCE: 29
```

-continued

```
Phe Gln Leu Gly Leu Asn Leu
1               5


<210> SEQ ID NO 30
<211> LENGTH: 355
<212> TYPE: PRT
<213> ORGANISM: Artificial Sequence
<220> FEATURE:
<223> OTHER INFORMATION: Amino acid sequence encoding MOT isolated from
      potato.

<400> SEQUENCE: 30

Phe Ile Leu Phe Phe Phe Phe Tyr Phe Phe His Tyr Leu Ile His Ile
1               5                   10                  15

His Ser Phe Phe Lys Lys Ser Phe Arg Leu Asp Ser Phe Gly Ile Met
            20                  25                  30

Gly Val Lys Gly Phe Val Glu Gly Gly Ile Ala Ser Ile Ile Ala Gly
        35                  40                  45

Cys Ser Thr His Pro Leu Asp Leu Ile Lys Val Arg Met Gln Leu Gln
    50                  55                  60

Gly Glu Thr Pro Ile Ser Ala Pro Ala Thr Val His Asn Leu Arg Pro
65                  70                  75                  80

Ala Leu Ala Phe His Thr Gly Ala Ala Asn His Thr Phe Ser Ile Pro
                85                  90                  95

Ala Pro Ser Val Val Ala Pro Pro Arg Val Gly Pro Val Ser Val Gly
            100                 105                 110

Val Lys Ile Ile Gln Gln Glu Gly Val Ala Ala Leu Phe Ser Gly Val
        115                 120                 125

Ser Ala Thr Val Leu Arg Thr Asp Thr Leu Leu Tyr Asn Gln Asn Gly
    130                 135                 140

Phe Ile Arg Tyr Ala Glu Ala Lys Met Asp Arg Ser Arg Tyr Tyr Ile
145                 150                 155                 160

Met Pro Leu Ser Lys Lys Ile Val Ala Gly Leu Ile Ala Gly Gly Ile
                165                 170                 175

Gly Ala Ala Val Gly Asn Pro Ala Asp Val Ala Met Val Arg Met Gln
            180                 185                 190

Ala Asp Gly Arg Leu Pro Ile Ser Gln Arg Arg Asn Tyr Lys Ser Val
        195                 200                 205

Ile Asp Ala Ile Ser Gln Met Ser Lys Ser Glu Gly Val Thr Ser Leu
    210                 215                 220

Trp Arg Gly Ser Ser Leu Thr Val Asn Arg Ala Met Leu Val Thr Ala
225                 230                 235                 240

Ser Gln Leu Ala Ser Tyr Asp Gln Phe Lys Glu Thr Ile Leu Glu Lys
                245                 250                 255

Gly Leu Met Lys Asp Gly Leu Gly Thr His Val Thr Ser Ser Phe Ala
            260                 265                 270

Ala Gly Phe Val Ala Ala Val Ala Ser Asn Pro Val Asp Val Ile Lys
        275                 280                 285

Thr Arg Val Met Asn Met Lys Val Glu Pro Glu Met Ala Pro Pro Tyr
    290                 295                 300

Asn Gly Ala Ile Asp Cys Ala Met Lys Thr Ile Lys Ala Glu Gly Pro
305                 310                 315                 320

Met Ala Leu Tyr Lys Gly Phe Ile Pro Thr Ile Ser Arg Gln Gly Pro
                325                 330                 335

Phe Thr Val Val Leu Phe Val Thr Leu Glu Gln Val Arg Lys Met Leu
            340                 345                 350
```

```
Lys Asp Phe
        355


<210> SEQ ID NO 31
<211> LENGTH: 9
<212> TYPE: PRT
<213> ORGANISM: Artificial Sequence
<220> FEATURE:
<223> OTHER INFORMATION: Amino acid sequence encoding MOT isolated from
      potato.

<400> SEQUENCE: 31

      Arg Arg Lys Lys Lys Leu Met Gly Phe
      1               5


<210> SEQ ID NO 32
<211> LENGTH: 37
<212> TYPE: PRT
<213> ORGANISM: Artificial Sequence
<220> FEATURE:
<223> OTHER INFORMATION: Amino acid sequence encoding MOT isolated from
      potato.

<400> SEQUENCE: 32

Glu Phe Lys Lys Lys Leu Ser Leu Ile Tyr Val Phe Lys Phe Leu Ser
1               5                   10                  15

Leu Gly Lys Val Ile Leu Cys Cys Val Leu Ile Leu Leu Leu Leu Leu
            20                  25                  30

Leu Leu Tyr Glu Lys
        35


<210> SEQ ID NO 33
<211> LENGTH: 8
<212> TYPE: PRT
<213> ORGANISM: Artificial Sequence
<220> FEATURE:
<223> OTHER INFORMATION: Amino acid sequence encoding MOT isolated from
      potato.

<400> SEQUENCE: 33

Val Leu Val Trp Trp Lys Lys Lys
1               5


<210> SEQ ID NO 34
<211> LENGTH: 300
<212> TYPE: PRT
<213> ORGANISM: Artificial Sequence
<220> FEATURE:
<223> OTHER INFORMATION: MOT potato protein.
<221> NAME/KEY: PEPTIDE
<222> LOCATION: (240)..(240)
<223> OTHER INFORMATION: Amino acid 240 is "Xaa" wherein "Xaa" = any
      amino acid.

<400> SEQUENCE: 34

Leu Ile Lys Val Arg Met Gln Leu Gln Gly Glu Thr Pro Ile Ser Ala
1               5                   10                  15

Pro Ala Thr Val His Asn Leu Arg Pro Ala Leu Ala Phe His Thr Gly
            20                  25                  30

Ala Ala Asn His Thr Phe Ser Ile Pro Ala Pro Ser Val Val Ala Pro
        35                  40                  45

Pro Arg Val Gly Pro Val Ser Val Gly Val Lys Ile Ile Gln Gln Glu
    50                  55                  60

Gly Val Ala Ala Leu Phe Ser Gly Val Ser Ala Thr Val Leu Arg Thr
```

-continued

```
65                  70                  75                  80

Asp Thr Leu Leu Tyr Asn Gln Asn Gly Phe Ile Arg Tyr Ala Glu Ala
                85                  90                  95

Lys Met Asp Arg Ser Arg Tyr Tyr Ile Met Pro Leu Ser Lys Lys Ile
            100                 105                 110

Val Ala Gly Leu Ile Ala Gly Gly Ile Gly Ala Ala Val Gly Asn Pro
        115                 120                 125

Ala Asp Val Ala Met Val Arg Met Gln Ala Asp Gly Arg Leu Pro Ile
    130                 135                 140

Ser Gln Arg Arg Asn Tyr Lys Ser Val Ile Asp Ala Ile Ser Gln Met
145                 150                 155                 160

Ser Lys Ser Glu Gly Val Thr Ser Leu Trp Arg Gly Ser Ser Leu Thr
                165                 170                 175

Val Asn Arg Ala Met Leu Val Thr Ala Ser Gln Leu Ala Ser Tyr Asp
            180                 185                 190

Gln Phe Lys Glu Thr Ile Leu Glu Lys Gly Leu Met Lys Asp Gly Leu
        195                 200                 205

Gly Thr His Val Thr Ser Ser Phe Ala Ala Gly Phe Val Ala Ala Val
    210                 215                 220

Ala Ser Asn Pro Val Asp Val Ile Lys Thr Arg Val Met Asn Met Xaa
225                 230                 235                 240

Val Glu Pro Glu Met Ala Pro Pro Tyr Asn Gly Ala Ile Asp Cys Ala
                245                 250                 255

Met Lys Thr Ile Lys Ala Glu Gly Pro Met Ala Leu Tyr Lys Gly Phe
            260                 265                 270

Ile Pro Thr Ile Ser Arg Gln Gly Pro Phe Thr Val Val Leu Phe Val
        275                 280                 285

Thr Leu Glu Gln Val Arg Lys Met Leu Lys Asp Phe
    290                 295                 300


<210> SEQ ID NO 35
<211> LENGTH: 299
<212> TYPE: PRT
<213> ORGANISM: Panicum miliaceum

<400> SEQUENCE: 35

Met Ala Asp Ala Lys Gln Gln Gln Ala Val Ala Pro Ser Ala Ala Trp
1               5                   10                  15

Met Met Val Lys Pro Phe Val Asn Gly Gly Ala Ser Gly Met Leu Ala
            20                  25                  30

Thr Cys Val Ile Gln Pro Ile Asp Met Val Lys Val Lys Ile Gln Leu
        35                  40                  45

Gly Glu Gly Ser Ala Ala Thr Val Thr Lys Lys Met Leu Ala Asn Glu
    50                  55                  60

Gly Ile Gly Ser Phe Tyr Lys Gly Leu Ser Ala Gly Leu Leu Arg Ala
65                  70                  75                  80

Thr Tyr Thr Thr Ala Arg Leu Gly Ser Phe Arg Val Leu Thr Asn Lys
                85                  90                  95

Ala Val Glu Ala Asn Glu Gly Lys Pro Leu Pro Leu Leu Gln Lys Ala
            100                 105                 110

Val Ile Gly Leu Thr Ala Gly Ala Ile Gly Ala Ser Val Gly Ser Pro
        115                 120                 125

Ala Asp Leu Ala Leu Ile Arg Met Gln Ala Asp Ser Thr Leu Pro Ala
    130                 135                 140
```

-continued

```
Ala Gln Arg Arg Asn Tyr Lys Asn Ala Phe His Ala Leu Tyr Arg Ile
145                 150                 155                 160

Val Ala Asp Glu Gly Val Leu Ala Leu Trp Lys Gly Ala Gly Pro Thr
                165                 170                 175

Val Val Arg Ala Met Ser Leu Asn Met Gly Met Leu Ala Ser Tyr Asp
            180                 185                 190

Gln Ser Val Glu Leu Phe Arg Asp Lys Leu Gly Ala Gly Glu Leu Ser
        195                 200                 205

Thr Met Leu Gly Ala Ser Ala Val Ser Gly Phe Cys Ala Ser Ala Cys
    210                 215                 220

Ser Leu Pro Phe Asp Tyr Val Lys Thr Gln Ile Gln Lys Met Gln Pro
225                 230                 235                 240

Asp Ala Asn Gly Lys Tyr Pro Tyr Thr Gly Ser Leu Asp Cys Val Met
                245                 250                 255

Lys Thr Leu Lys Ser Gly Gly Pro Phe Lys Phe Tyr Thr Gly Phe Pro
            260                 265                 270

Val Tyr Cys Val Arg Ile Gly Pro His Val Met Leu Thr Trp Ile Phe
        275                 280                 285

Leu Asn Gln Ile Gln Lys Phe Glu Lys Asp Met
    290                 295
```

<210> SEQ ID NO 36
<211> LENGTH: 37
<212> TYPE: DNA
<213> ORGANISM: Artificial Sequence
<220> FEATURE:
<223> OTHER INFORMATION: PCR fragment.

<400> SEQUENCE: 36

```
atggatcccg cttctcctct ttatatatag ttatggg                           37
```

<210> SEQ ID NO 37
<211> LENGTH: 3933
<212> TYPE: DNA
<213> ORGANISM: Artificial Sequence
<220> FEATURE:
<223> OTHER INFORMATION: UBL-1 promoter nucleic acid sequence.

<400> SEQUENCE: 37

```
ggatcctttc acctcctaat acaaaagttt ccattttttt aagcaggcaa tgatagtttt     60

tgttaatgct aatctttgtt accatatatg gtctttatca gagcctccag acatccggaa    120

ctggttctct agctatgttt atgaatctcc aaaagtggat actattcaag attccatact    180

tccagatcat gagaaagaat tagatgacaa agtgtgtacg aatggataca gtggcggtga    240

ggaacctcag aattttagga attcattagg aactcctttt atccatgatg acaagtatga    300

gcatcaaact gcctcaaagg taaacttaga accttcagct gcatcaaact cctttcatac    360

atcctcttga tctacatcaa ttctttgtga actcatgctt tagatgttga tttattgaat    420

gtacactcaa agtaaacgta gaaccttaag ctgtagatca acaaacagat ggattttatc    480

tttctgcgat tgtacgaacc tttttggctg gagggatcag tacctagaat atacaataag    540

attacattga gttacagtgt tggatcacat agttgaacat atgtacaaaa caaagacaga    600

aagaaacatt aaaagatcta ttctgtcttt agttagttag aaacttaggt attttcagtt    660

ggctggtagc tatgcatata aaccatctca tctccgattc tgttagttat acaattgttt    720

ctaccatgca aagaagataa ctgacacttc agctacataa ttgaggtcta ccttaccata    780

ttgtcataag ttcccttgat gatttccttt gtgtttgtat gcttcgaagg atcaggaggc    840
```

-continued

```
tgatgggaca aagaacgcaa gaatatccaa tgaaatgtct catgagagaa tttctcaaca    900
gacactaaat cacaagacaa cggagaacac caattgtggt tcaccaagat acattgacat    960
ggtcttcaaa gagagtgatg gagaacactt ggagaccatt tttcctcaag aagttaactg   1020
caaagtatcc tgcaccatca atcattctag ctgtgaaggt gaaaaattat acagacatcc   1080
aattcacagg aaggattctg cagagaacag ttcgaaatct aaagatagtg ttgaacctgc   1140
tgatgatgtg caatctaaaa ataggatgga gatgagtgtg ttaagtcaga agttatccaa   1200
acggaaagca gcagaaatca tcgacaaaga aaatcacata aatgactttg gagagaatgg   1260
ttttatatca accagaaaga gtagaaatag tcaagtgcag aacaaaagtc ctttgccaac   1320
gccagctgca gttcagtctc ctttaagtgg agtcactgtt gcatcaaact gccacaagca   1380
gggtttgact agaaaggtac tcacagaaac aaccaacttg catcctagtg ctttggaaaa   1440
aacaggaaaa tggcggtgcc cccaaaggac taagccaaat attggtcctc ctctaaagca   1500
gcttcgacta gagcaatggg ttcgtcgagc ttaagtctaa tacattctta tgaagagaaa   1560
atggatatca agaatggtag aattcaaaag aggtttgtgc atgttagcta gtgaaagatg   1620
tgagaacaag acttggcaca atgctagagt tactatatcg tggttgtcaa tttacaatgc   1680
aaatgagatc tattaaattg acaaccacga tatttagatt ttttttaata ggtttggcct   1740
tgagtctaat tttgttggac attcacatga tcaaatagat tgaagtattt tttaattagg   1800
agcgtttcaa ctcacttatt aggtctattc gacacaagtt tagattgatt atcttcactt   1860
gtttcggaca ccaagttatt aaactgaaaa atataaaggc gaaatggtct ggtggaccct   1920
catacttgta tgtgtttgtt ttgtgaatcc ttctacttgt ttctttgtca tctgaaccct   1980
tgaactcatc aaaacacaat attttaaaca cgtttttttac tactcaaatg tgtgtgtatt   2040
acaaatgcct gacacgtaat tttaaaaata attataaaat gacacgtata attataaaat   2100
gacacatgta tatatgatca ctccatgtca tttttccttt tattatattt gattaatata   2160
cctacacttt ctctttccaa tttttatttc tctttgtcat agccatctgc atctgcattt   2220
ccattcccac aatctctttt caactttttc ttatcttcct taccctttc ctttttccaa    2280
tctcttctac tctttccatt caagtaaaaa atgttggtac gatttctgat tgttcacaat   2340
ctcgtcgaag ttcggagttg attttgggtt ctgttggatt gggattttgg tggtgaccgg   2400
tggcgctaag gaaaagtggg ggtctattgg gtggtctgat tgtttctagt tgttcacaac   2460
tagcggcgtt gtgaaagtcg agacttattg gcagagttag tttggtgttt ttgtcttagt   2520
tgttgttgtt gttggttctc atttatagtt gttggttgaa gcttgtcgga gatggtgaga   2580
acgaaggcaa tttggtcgga gaaggtgagg aggacgagaa gaaggcaata agtttgagtt   2640
tggtttggaa ctgaaacaag gggtcaatgt caaatatatt tgagtttttt tgtttgattt   2700
tcaacttatc taggtaggtt ttccaattta ttttcgaatt tatttgttgt ttagtttgga   2760
tttgatctct atttgtgtct ttgtttgatt ttggggtttt agtcgattac attgattttg   2820
ttgatttttt ttggggattt tgtatttttg tgtctaatgt tagtgtaaga tattttggta   2880
gtagtgttat gccttccatg gcatttttca taaaaaaaaa agaagagttg tataataaca   2940
agaaacgata gagaagaaat ttggggggaa aagatcaaaa aagaggccaa gaaaagctca   3000
aattttgtcc aacaatggtg ttagatgcaa ataggaagat gatggcttta caaagcccta   3060
atgtcactgt taaacccttt tccaagggtc tcacgctcct aataggtgtg tgtcacacac   3120
tctttgatat tcactgccac ataggatgtc aagtcaaaaa tagtgtttaa aatattgtgt   3180
```

-continued

```
tttgataagt tcaggggttc agatgacaaa tgggcaagta gaagggttca caatacaaac   3240
atatacaagt ataagagtcc accagaccat ttcsccaaat ataaatagat gggaagtgta   3300
gatctcctca aaattctttt agtaacagta aacactcata tacaaaaata tgtaatatga   3360
agttatgtgc aaccaaataa aattttaaaa attgaaactt tcttttttg tttcccaccc   3420
tatatatcag ggaccacatt ggagtctgga ttaaatttga atcgtgtatt gtagggatca   3480
ttttccaata gaattttctc catactccgg aaaagttgaa aacttgctct tttgataaaa   3540
atgttgttta aaagggaaat atatttgaaa caatcaaatg tgttcctgga aaagtatctc   3600
gtgttaataa cttgctaaat atttagcatt ctaatatacc tttgaattta aattcttcat   3660
cttgtggttt ttttcaactt taaatattca aaatactggt aaattgattt agtgatctat   3720
tacaatttta gttttaggtc caatcaaatc tctccaacat tttattttt attcttaaaa   3780
tatttctttt ataaaattat attttattta aattgtaaaa acaaacaaac aaaaaatgat   3840
aaagaaaaat aagaagacga gggtgctaga aaatgataaa aacccccca ccataaagcc   3900
cttcccataa ctatatataa agaggagaag gcg                                3933
```

<210> SEQ ID NO 38
<211> LENGTH: 1031
<212> TYPE: DNA
<213> ORGANISM: Artificial Sequence
<220> FEATURE:
<223> OTHER INFORMATION: MOT3 promoter nucleic acid sequence.

<400> SEQUENCE: 38

```
ggatccatta gttacacatt gtagactttt aacttttcaa tggcataatt cctcacgtaa     60
tcaaataaat aattttttct cttttctatc taacattttc tcttgaaaaa tataaagtag    120
tggtaactat tgtccaattg taattcaaat atgaggcatc ttttcattat acaatcgact    180
tgaagtagaa tatttataag attttatgcc ttattgagaa tctaattgtt ataaatagtt    240
tataaaagtc aatttctttt aaatttatta ttcgtatcag ttaaaaaaat tatatcccaa    300
cattgttatt cgtattgtta gtaaaaatta actgcatgtc tggcttttct tgaacatagt    360
tgatgatcta ttgatgcgcg atcttcattc atttgttgat ctaattatgc gtataaatta    420
taatcaaata aaacgacatg tttaagtggt taatttgtct acgtaacaaa aaattgagta    480
ttcatacaaa aacttaacaa aaattgaatc aaaattatct aatataaaca tttatatatt    540
caatcagaac ataccatact tcaaatatct aaatagctaa aaaataataa tacaaatgaa    600
gtgaccggat caagattttt gagttatatt acacttttca tttatggctg agtcaaaatt    660
ttcactaaaa aattcaaaat taacacgcaa taaaacaaaa caaaattcaa cacctaaaaa    720
gagtcaaatg aatgaaaaat cccctcgatc ctacttaact ccgcccccaa cttccaactt    780
cattattaca accaaaaaat atttccattg accaaaggct cctactttcc ttccgccgca    840
gagaaaagta tactgaaaga acccgcgttg tatacaaaac ctaatttccc tttcctttcc    900
tttccctttc cctttttcc cttataaatt cgtttcttcc tcttccttct caactcacaa    960
ttttatgtct cacagactca acgttccaca cttcgcatct atagctttcg gtctccattc   1020
ccatctcctg g                                                        1031
```

<210> SEQ ID NO 39
<211> LENGTH: 2813
<212> TYPE: DNA
<213> ORGANISM: Artificial Sequence
<220> FEATURE:
<223> OTHER INFORMATION: MOT6 promoter nucleic acid sequence.

<400> SEQUENCE: 39

```
ggatctcatt ttctaaacat gcttgaaatt tatggtctaa aataagtcac agatgattat     60
gcggctatat aacaatattt gcttgaactc cattttcgaa cttatcatcc ggagttaggt    120
gagtctaatt tgttacttcg gatctttgat agatatgaac tatcctatta ggcgtggcac    180
aagtccatgt ttggtttggg taccgctatg ttggacttga ttgaattttg atcgttggat    240
atcgcttgat gatatattcc aatgtttaaa ttgaattttg attcatatga atttttaaaa    300
tcatcaaaca atacatgaca aagaacaagt tcatatgcta catagatgtg tttgggctta    360
attgacatag attaaagaat aaatttataa tgcattgagt tcaatgagct tagtaataaa    420
tgtatgcaca aagccaattg tataaaaatg tgcaaattac tcaaccaaat ctaaaaataa    480
gacgacttta gactaatttt ataacatctt aattgaccaa gtcgacatga ttttatttca    540
aaccacatat atatgctctc tttttttttag aaagaaaaaa taaacaaatt tacaccccaa    600
agttttactt gtgggataaa gtagctttgg actttcaaaa ttgttgttat aaccagataa    660
atgctgattt tcgtttttca attttgtctt tataaagaaa tgaatttgga ttctaactca    720
atcataaaaa ttagttaaga gatgggaata ttgtctaaac catattaaag agatccccac    780
ccccacccac cgactcgaaa gcaagaggca agagcgcaac aactacatga aagccttatg    840
agtaaggtta atcgaagtca gaaaaagttt attggcaaga gggaatcaaa tattttaaaa    900
tatttgggtc ctccactcat caaaatttat atgatatttt ttccttttra gttcgtttta    960
aaaagaacag aatcttctat atttagtaac aacttaactt taactrcaca tattttaggt   1020
aagtaaattt catattttta ccattaataa gatgatttat agccgcatag atatctatga   1080
cttattttaa gctataaatt ttaaaaatct ttcttttatt cttaaacttc atgccgaagc   1140
gaacacctaa agaataatag tattttattt aatcacaaag aacaagtaac accatgttac   1200
gttaatatag gaacaatatt atatcatgcc cacctccaaa ggacaacaaa aaaagaaaga   1260
aaaaaaaaag tcaaaatggc ttcttagcca ccaaaaaaaa gttttattta attaaaagct   1320
ctttttaat ttcacacgtt taagggagaa taattctaag tagagtactt tgacctaaga   1380
aattttgaaa aagtcatagt caaaactata aaagtcaaaa agaattgaat ccattttcac   1440
ataattttca atatcacatt tagtaatgat tgataaattc agtactaaaa taaatcaaaa   1500
attcataaat ttaagtttga ctttgcttct ctttaataaa ataatttaaa tggtatgaaa   1560
tcatattaat cagatcgata aatttagaat agtaaataca taaacaaaag gttttattta   1620
tgggatcata agttgttgcc tagtaggtaa aggagcgtgt gctaggcaca tgcataaggg   1680
tcctacaact tctactacta gtgagcccat ataagtgaaa ctcgaagatt gttctcattt   1740
aataatatct tattcttcgt ttatattatt atttgtattt tttttcttcg attatcgtat   1800
tatatatatt gctcactatg ttcagcataa ctgcttcatt gttgtatttc ccttttcata   1860
cttgatttta ttattcttta agccgagagt ctattgtcca attgtaattt aaatatgagg   1920
cctcttttga ttatacaatt gacattttaa gtagaatatg ttttgagaat ctaattgtta   1980
taaatagcgt ataaaagtca atttctttta agttcattat ttgtgtcagt aaaaaaaaaa   2040
aactatattt caaaattgtt attcgtactg ttgttagtaa aaaataactg catgtctggc   2100
ttttcttgaa cggtctattg atgcgcgatc ttcatccatt tgctgatcta attatgcgta   2160
taaattataa taaaaataaa acgacatatt ttaagtggtt aatttgtcta cgtaacaagc   2220
aattgagtat tcatacaaaa acttaacaaa atttgaatta aaattatcta atataagcat   2280
```

-continued

```
ttatatcata tatttaagta ttcaatcaga gcataccata tttcaaatat ctaaatagct   2340

aaaaaaaaat acaaatgaag tgactgggtc aagatttttg tgttatatta cattttccat   2400

gtgtggacgt ctgagtcaaa attttcacta aacaatcaca aaacacaaaa caaaattcaa   2460

cacctaaaaa gagtcaaata aatgaaaaat cccctcgatc cgacttaact ccccccgac    2520

ttctaacttc attattacaa ccaaaaaata tttccattga ccaaaggccc ccactttcct   2580

tccgccgcag agaaaagtat actgaaagaa cccgcgttgt atacaaaacc taatttccct   2640

ttcctttcct ttcccttccc tttttccctt ataaattcgc ttcttcctct tccttctcaa   2700

ctcacaattt atatgtctca cagactcaac gttccacact tcgcatctat agctttcggt   2760

ctccattccc atctcctggt ttccagtgag atgaactcta attccaattg ggc          2813
```